United States Patent
Hirsch et al.

(10) Patent No.: US 10,212,943 B2
(45) Date of Patent: Feb. 26, 2019

(54) PLANT GROWTH-PROMOTING MICROORGANISMS AND METHODS OF USE THEREOF

(71) Applicants: The Regents of the University of California, Oakland, CA (US); B.G. Negev Technologies and Applications Ltd., Beer-Sheva (IL)

(72) Inventors: Ann M. Hirsch, Santa Monica, CA (US); Drora Kaplan, Beer-Sheva (IL)

(73) Assignees: The Regents of the University of California, Oakland, CA (US); B.G. Negev Technologies and Applications Ltd, Beer-Sheva (IL)

( * ) Notice: Subject to any disclaimer, the term of this patent is extended or adjusted under 35 U.S.C. 154(b) by 0 days.

(21) Appl. No.: 14/897,414

(22) PCT Filed: Jun. 10, 2014

(86) PCT No.: PCT/US2014/041779
§ 371 (c)(1),
(2) Date: Dec. 10, 2015

(87) PCT Pub. No.: WO2014/201044
PCT Pub. Date: Dec. 18, 2014

(65) Prior Publication Data
US 2016/0143295 A1    May 26, 2016

Related U.S. Application Data

(60) Provisional application No. 61/833,374, filed on Jun. 10, 2013.

(51) Int. Cl.
| A01N 63/02 | (2006.01) |
| C12N 1/20 | (2006.01) |
| A01N 63/00 | (2006.01) |
| C12R 1/07 | (2006.01) |
| C12R 1/125 | (2006.01) |

(52) U.S. Cl.
CPC ............. *A01N 63/02* (2013.01); *A01N 63/00* (2013.01); *C12N 1/20* (2013.01); *C12R 1/07* (2013.01); *C12R 1/125* (2013.01)

(58) Field of Classification Search
None
See application file for complete search history.

(56) References Cited

U.S. PATENT DOCUMENTS

| 6,194,193 B1 | 2/2001 | Drahos et al. ............. 435/252.4 |
| 2007/0148754 A1* | 6/2007 | Marrelli ................... A01H 3/00 435/252.3 |
| 2012/0003197 A1* | 1/2012 | Jacobsen ................ A01N 63/02 424/93.46 |

FOREIGN PATENT DOCUMENTS

CN    102643766 A    8/2012

OTHER PUBLICATIONS

Rathnayake, Development of Whole-Cell Microbial Biosensors to Assess the Heavy Metal Bioavailability in the Soil Environment, University of South Australia (2010), pp. 1-218.*
Kaplan et al., American Journal of Botany (2013), vol. 100, No. 9, pp. 1713-1725.*
Schwartz et al. Agronomy (2013), vol. 3, pp. 595-620.*
Angus et al., PLOS ONE (Jan. 8, 2014), vol. 9, No. 1, pp. 1-12.*
International Search Report and Written Opinion for PCT/US2014/041779, dated Dec. 29, 2014.
Roberts et al., "Biocontrol agents applied individually and in combination for suppression of soilborne diseases of cucumber", *Crop Protection* 24(2):141-155, 2005.
Tak et al., "Advances in the Application of Plant Growth-Promoting Rhizobacteria in Phytoremediation of Heavy Metals", *Reviews of Environmental Contamination and Toxicology* 223:33-52, 2012.

* cited by examiner

*Primary Examiner* — Sue X Liu
*Assistant Examiner* — Frank Choi
(74) *Attorney, Agent, or Firm* — Norton Rose Fulbright US LLP

(57) ABSTRACT

The present disclosure relates to the field of plant-microorganism interactions. In particular, the present disclosure relates to methods and compositions for increasing plant growth characteristics by growing the plant in the presence of plant growth-promoting microbial strains.

15 Claims, 25 Drawing Sheets
Specification includes a Sequence Listing.

Change in pea root architecture for either uninoculated plants A) plants or B) plants inoculated with B. simplex 30N-5 after 2 weeks. Bar, 1 cm. 164x219mm (300 x 300 DPI)

PLANT GROWTH-PROMOTING MICROORGANISMS AND METHODS OF USE THEREOF

CROSS REFERENCES TO RELATED APPLICATIONS

This application is a national phase application under 35 U.S.C. § 371 of International Application No. PCT/US2014/041779, filed Jun. 10, 2014, which claims the benefit of U.S. Provisional Application No. 61/833,374, filed Jun. 10, 2013. The entire contents of each of the above-referenced disclosures are specifically incorporated herein by reference without disclaimer.

STATEMENT REGARDING FEDERALLY SPONSORED RESEARCH OR DEVELOPMENT

This invention was made with Government support under Grant Nos. 0747516 and 1137471, awarded by the National Science Foundation; and Grant No. GM055052, awarded by the National Institutes of Health. The Government has certain rights in the invention.

The instant application contains a Sequence Listing which has been filed electronically in ASCII format and is hereby incorporated by reference in its entirety. Said ASCII copy, created on Aug. 21, 2018, is named UCLA_P0016US_SL.txt and is 869 bytes in size.

FIELD

The present disclosure relates to the field of plant-microorganism interactions. In particular, the present disclosure relates to methods and compositions for increasing plant growth characteristics by growing the plant in the presence of plant growth-promoting microbial isolates.

BACKGROUND

Plant roots generally account for over 50% of a plant's biomass. Part of that biomass includes the root microbiome, which is the assemblage of bacteria and fungi living in the rhizosphere (typically the 1-3 mm region adjacent to the external surface of the root). Soil bacteria that associate with plant roots and have a positive effect on plant growth are generally known as plant growth-promoting bacteria (PGPBs). PGPBs can fix nitrogen, secrete plant hormones or antibiotics, solubilize phosphate, inhibit pathogenic microorganisms, and/or modify insoluble $Fe^{3+}$ to utilizable forms of iron (Lugtenberg & Kamilova, 2009; and Ortíz-Castro et al., 2009). In addition, soil bacteria can also stimulate phytoremediation and by attaching to roots, and improve plant health by increasing the numbers of biodegradative bacteria (Glick, 2010).

Many PGPB studies have focused on Gram-negative bacteria such as the pseudomonads, which are simple to culture and suitable for genetic manipulation. However, a large number of additional microorganisms also exhibit plant growth-promoting (PGP) activity. For example, several *Bacillus* species have been shown to have PGP activity (Zhang J. et al., 1996; Zhang H. et al., 2008; Zhang H. et al., 2010; Idris et al., 2007; Benhamou et al., 1996; Probanza et al., 2001; Bai et al., 2003; Handelsman et al., 1990; and López-Bucio et al., 2007). Combinations of several *Bacillus* species have also been shown to enhance plant growth. For example, Francis et al. (2010) describe the interactions of *Bacillus* species as well as other Gram-positive bacteria with plants. It has also been shown that co-inoculating legumes with rhizobia and various *Bacillus* species, including *B. subtilis*, resulted in altered root architecture and enhanced nodulation for bean (Petersen et al., 1996; and Srinivasan et al., 1997), peanut (Turner & Backman, 1991), pigeon pea (Rajendran et al., 2008), and soybean (Halverson & Handelsman, 1991; and Bai et al., 2003). Accordingly, even within a well-studied genus like *Bacillus*, a need exits for identifying and isolating additional new microorganisms with PGP activity.

It has also been shown that microorganism diversity and complexity on the surfaces of plant roots are highly correlated with edaphic factors such as moisture, pH, climate, parent rock material, temperature, and nutrient and organic matter content (Lau and Lennon, 2011; and Brockett et al., 2012). However, the plants themselves also have a significant influence on the composition of their microbiomes, especially in the rhizosphere. Plants that live in harsh environments (e.g., arid and nutrient-poor environments), such as deserts, have been called "resource" (Halvorson et al., 1994) or "fertility" islands (Schlesinger et al., 1996) because they support a diversity of organisms within and below their root system in spite of the challenging conditions of desiccation and low nutrient availability. Plants adapted to harsh environments and their association with microorganisms within these habitats makes both partners highly competitive and adaptive (Basil et al., 2004).

The majority of studies on microbial communities have been limited to those from mesic environments (e.g., forests, grasslands, and agricultural fields), whereas very few studies have been performed on desert or other arid environment root microbiomes (Barns et al., 1999). However, those few studies of microbial communities within various desert environments have revealed both antifungal (Basil et al., 2004) and antibiotic (Hozzein et al., 2008) properties, indicating that desert habitats may be a source of plant growth-promoting microorganisms. With increasing demands for food as the world's human population expands, more and more desert land is being utilized for either food or biofuel crop production. Thus, there also exists a need for identifying and isolating additional microorganisms from harsh environments, such as deserts, that promote plant growth of crop plants cultivated in such harsh environments.

BRIEF SUMMARY

In order to meet these needs, the present disclosure provides novel microbial isolates, combinations of such isolates, compositions containing such isolates, and methods of using such isolates for increasing plant growth characteristics in plants. Moreover, the present disclosure is based, at least in part, on the surprising discovery of novel plant growth-promoting microorganisms (PGPM) identified and isolated from plant tissue, roots, plant-associated soil, and/or surrounding soil samples from a *Podocarpus nagi* tree, and the native desert plants *Zygophyllum dumosum* Boiss. (Zygophyllaceae) and *Atriplex halimus* (Amaranthaceae). Without wishing to be bound by theory, it is believed that the microorganisms isolated from the desert plants have plant growth-promoting activity, because the extreme conditions of desert environments necessitate robust, adaptive responses to maintain viability.

Accordingly, certain aspects of the present disclosure relate to a method of increasing one or more plant growth characteristics in a plant, by: growing the plant in the presence of one or more plant growth-promoting microbial isolates selected from *Arthrobacter pascens, Arthrobacter* ramosus, Arthrobacter oryzae, Arthrobacter humicola, Arthrobacter oxydans, Arthrobacter globiformis, Citricoccus alkalitolerans, Arthrobacter aurescens, Arthrobacter agilis, Arthrobacter tumbae, Arthrobacter arilaitensis, Arthrobacter crystallopoeietes, Kocuria rosea, Arthrobacter citreus, Georgenia ruanii, Microbacterium paludicola, Microbacterium aerolatum, Microbacterium testaceum, Microbacterium paraoxydans, Microbacterium phyllosphaerae, Microbacterium oxydans, Streptomyces griseus, Streptomyces olivoviridis, Streptomyces cirratus, Streptomyces candidus, Streptomyces chryseus, Streptomyces peucetius, Streptomyces flaveus, Streptomyces griseoruber, Streptomyces bottropensis, Streptomyces phaeochromogenes, Streptomyces fradeiae, Streptomyces durmitorensis, Streptomyces coeruleofuscus, Streptomyces marokkonensis, Streptomyces althioticus, Streptomyces pseudogriseolus, Streptomyces azureus, Williamensia muralis, Mycobacterium sacrum, Rhodococcus jostii, Nocardiopsis quinghaiensis, Terribacillus halophilus, Bacillus cibi, Bacillus idriensis, Bacillus licheniformis, Bacillus herbersteinensis, Bacillus simplex, Staphylococcus succinus, Bacillus benzoevorans, Bacillus niacin, Virgibacillus halodenitrificans, Oceanobacillus picturae, Bacillus psychordurans, Planomicrobium okeanokoites, Planococcus maritimus, Planococcus psychrotoleratus, Olivibacter soli, Bartonella elizabethae, Stenotrophomonas rhizophila, Halomonas aquamarina, Pseudomonas stutzeri, Pseudomonas fluorescens, Pseudomonas brassicacearum, Pseudomonas frederiksbergensis, Aspergillus fumigatiaffinis, Ochroconis sp., Micrococcus luteus, Citricoccus nitrophenolicus, Promicromonospora kroppenstedtii, Curtobacterium flaccumfaciens, Streptomyces halstedii, Paenibacillus tundrae, Exiguobacterium aurantiacum, Bacillus aquimaris, Planomicrobium koreense, Sinorhizobium medicae, Sinorhizobium meliloti, Mesorhizobium loti, Altererythrobacter luteolus, Massilia timonae, Stenotrophomonas maltophilia, Pseudomonas fulva, Pseudomonas syringae, Algoriphagus ratkowskyi, Phoma betae, Fusarium oxysporum, Cladosporium sphaerospermum, Alternaria thalictrigena, Fusarium equiseti, Penicillium chrysogenum, Penicillium commune, Pseudomonas putida, Pseudomonas plecoglossicida, Pseudomonas mosselii, Pseudomonas gessardii, Pseudomonas libanensis, Pseudomonas geniculata, Bacillus simplex 30N-5, Bacillus simplex 11, Bacillus simplex 237, and Bacillus subtilis 30VD-1.

In certain embodiments, the plant is grown in the presence of two or more, three or more, four or more, five or more, six or more, seven or more, eight or more, nine or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, or 90 or more of the plant growth-promoting microbial isolates. In certain embodiments, the plant is grown in the presence of one or more plant growth-promoting microbial isolates selected from *Arthrobacter tumbae, Kocuria rosea, Micrococcus luteus, Planococcus maritimus, Paenibacillus tundra, Bacillus simplex, Pseudomonas stutzeri*, and *Pseudomonas brassicacearum*. In certain embodiments, the plant is grown in the presence of *Arthrobacter pascens, Arthrobacter ramosus, Arthrobacter oryzae, Arthrobacter humicola, Arthrobacter oxydans, Arthrobacter globiformis, Citricoccus alkalitolerans, Arthrobacter aurescens, Arthrobacter agilis, Arthrobacter tumbae, Arthrobacter arilaitensis, Arthrobacter crystallopoeietes, Kocuria rosea, Arthrobacter citreus, Georgenia ruanii, Microbacterium paludicola, Microbacterium aerolatum, Microbacterium testaceum, Microbacterium paraoxydans, Microbacterium phyllosphaerae, Microbacterium oxydans, Streptomyces griseus, Streptomyces olivoviridis, Streptomyces cirratus, Streptomyces candidus, Streptomyces chryseus, Streptomyces peucetius, Streptomyces flaveus, Streptomyces griseoruber, Streptomyces bottropensis, Streptomyces phaeochromogenes, Streptomyces fradeiae, Streptomyces durmitorensis, Streptomyces coeruleofuscus, Streptomyces marokkonensis, Streptomyces althioticus, Streptomyces pseudogriseolus, Streptomyces azureus, Williamensia muralis, Mycobacterium sacrum, Rhodococcus jostii, Nocardiopsis quinghaiensis, Terribacillus halophilus, Bacillus cibi, Bacillus idriensis, Bacillus licheniformis, Bacillus herbersteinensis, Bacillus simplex, Staphylococcus succinus, Bacillus benzoevorans, Bacillus niacini, Virgibacillus halodenitrificans, Oceanobacillus picturae, Bacillus psychordurans, Planomicrobium okeanokoites, Planococcus maritimus, Planococcus psychrotoleratus, Olivibacter soli, Bartonella elizabethae, Stenotrophomonas rhizophila, Halomonas aquamarina, Pseudomonas stutzeri, Pseudomonas fluorescens, Pseudomonas brassicacearum, Pseudomonas frederiksbergensis, Aspergillus fumigatiaffinis, Ochroconis* sp., *Micrococcus luteus, Citricoccus nitrophenolicus, Promicromonospora kroppenstedtii, Curtobacterium flaccumfaciens, Streptomyces halstedii, Paenibacillus tundrae, Exiguobacterium aurantiacum, Bacillus aquimaris, Planomicrobium koreense, Sinorhizobium medicae, Sinorhizobium meliloti, Mesorhizobium loti, Altererythrobacter luteolus, Massilia timonae, Stenotrophomonas maltophilia, Pseudomonas fulva, Pseudomonas syringae, Algoriphagus ratkowskyi, Phoma betae, Fusarium oxysporum, Cladosporium sphaerospermum, Alternaria thalictrigena, Fusarium equiseti, Penicillium chrysogenum, Penicillium commune, Pseudomonas putida, Pseudomonas plecoglossicida, Pseudomonas mosselii, Pseudomonas gessardii, Pseudomonas libanensis*, and *Pseudomonas geniculate*. In certain embodiments, the plant is grown in the presence of *Bacillus subtilis* 30VD-1, *Bacillus simplex* 11, *Bacillus simplex* 237, and/or *Bacillus simplex* 30N-5. In certain embodiments that may be combined with any of the preceding embodiments, the one or more plant growth characteristics are selected from plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions. In certain embodiments that may be combined with any of the preceding embodiments, the one or more plant growth characteristics are growth under arid conditions, growth under low pH conditions, or both. In certain embodiments that may be combined with any of the preceding embodiments, the one or more plant growth characteristics are resistance to one or more pathogens, resistance to fungal growth, or both. In certain embodiments that may be combined with any of the preceding embodiments, further including growing the plant in the presence of one or more rhizobial bacterial strains. In certain embodiments that may be combined with any of the preceding embodiments, growing the plant in the presence of one or more plant growth-promoting microbial isolates includes contacting seed of the plant with the one or more plant growth-promoting microbial isolates. In certain embodiments that may be combined with any of the preceding embodiments, growing the plant in the presence of one or more plant growth-promoting microbial isolates includes contacting the plant or part thereof with the one or more plant growth-promoting microbial isolates. In certain embodiments that may be combined with any of the preceding embodiments, growing the plant in the presence of one or more plant growth-promoting microbial isolates includes contacting the plant roots with the one or more plant growth-promoting microbial isolates. In certain embodiments that may be combined with any of the preceding embodiments, growing the plant in the presence of one or more plant growth-promoting microbial isolates includes contacting the plant rhizosphere with the one or more plant growth-promoting microbial isolates. In certain embodiments that may be combined with any of the preceding embodiments, the rhizosphere includes one or more of roots, root nodules, root caps, root exudate, rhizosphere-associated microorganisms, and rhizosphere-associated soil. In certain embodiments that may be combined with any of the preceding embodiments, the plant is a dicotyledon. In certain embodiments that may be combined with any of the preceding embodiments, the plant is selected from a desert plant, a desert perennial, a crop plant, and a legume.

Other aspects of the present disclosure relate to a plant growth-promoting composition containing one or more plant growth-promoting microbial isolates selected from *Arthrobacter pascens, Arthrobacter ramosus, Arthrobacter oryzae, Arthrobacter humicola, Arthrobacter oxydans, Arthrobacter globiformis, Citricoccus alkalitolerans, Arthrobacter aurescens, Arthrobacter agilis, Arthrobacter tumbae, Arthrobacter arilaitensis, Arthrobacter crystallopoeietes, Kocuria rosea, Arthrobacter citreus, Georgenia ruanii, Microbacterium paludicola, Microbacterium aerolatum, Microbacterium testaceum, Microbacterium paraoxydans, Microbacterium phyllosphaerae, Microbacterium oxydans, Streptomyces griseus, Streptomyces olivoviridis, Streptomyces cirratus, Streptomyces candidus, Streptomyces chryseus, Streptomyces peucetius, Streptomyces flaveus, Streptomyces griseoruber, Streptomyces bottropensis, Streptomyces phaeochromogenes, Streptomyces fradeiae, Streptomyces durmitorensis, Streptomyces coeruleofuscus, Streptomyces marokkonensis, Streptomyces althioticus, Streptomyces pseudogriseolus, Streptomyces azureus, Williamensia muralis, Mycobacterium sacrum, Rhodococcus jostii, Nocardiopsis quinghaiensis, Terribacillus halophilus, Bacillus cibi, Bacillus idriensis, Bacillus licheniformis, Bacillus herbersteinensis, Bacillus simplex, Staphylococcus succinus, Bacillus benzoevorans, Bacillus niacini, Virgibacillus halodenitrificans, Oceanobacillus picturae, Bacillus psychordurans, Planomicrobium okeanokoites, Planococcus maritimus, Planococcus psychrotoleratus, Olivibacter soli, Bartonella elizabethae, Stenotrophomonas rhizophila, Halomonas aquamarina, Pseudomonas stutzeri, Pseudomonas fluorescens, Pseudomonas brassicacearum, Pseudomonas frederiksbergensis, Aspergillus fumigatiaffinis, Ochroconis sp., Micrococcus luteus, Citricoccus nitrophenolicus, Promicromonospora kroppenstedtii, Curtobacterium flaccumfaciens, Streptomyces halstedii, Paenibacillus tundrae, Exiguobacterium aurantiacum, Bacillus aquimaris, Planomicrobium koreense, Sinorhizobium medicae, Sinorhizobium meliloti, Mesorhizobium loti, Altererythrobacter luteolus, Massilia timonae, Stenotrophomonas maltophilia, Pseudomonas fulva, Pseudomonas syringae, Algoriphagus ratkowskyi, Phoma betae, Fusarium oxysporum, Cladosporium sphaerospermum, Alternaria thalictrigena, Fusarium equiseti, Penicillium chrysogenum, Penicillium commune, Pseudomonas putida, Pseudomonas plecoglossicida, Pseudomonas mosselii, Pseudomonas gessardii, Pseudomonas libanensis, Pseudomonas geniculata, Bacillus simplex* 30N-5, *Bacillus simplex* 11, *Bacillus simplex* 237, and *Bacillus subtilis* 30VD-1. In certain embodiments, the composition contains two or more, three or more, four or more, five or more, six or more, seven or more, eight or more, nine or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, or 90 or more of the plant growth-promoting microbial isolates. In certain embodiments, the plant growth-promoting microbial isolates include one or more characteristics selected from nitrogen fixation, siderophore production, iron chelation, phosphate solubilization, chitinase production, and cellulase production.

Other aspects of the present disclosure relate to an isolated *Bacillus subtilis* 30VD-1 strain having all the identifying characteristics of a *Bacillus subtilis* 30VD-1 strain deposited with NRRL as Accession No. B-50966. Other aspects of the present disclosure relate to an isolated *Bacillus simplex* 11 strain having all the identifying characteristics of a *Bacillus simplex* 11 strain deposited with NRRL as Accession No. B-50967. Other aspects of the present disclosure relate to an isolated *Bacillus simplex* 237 strain having all the identifying characteristics of a *Bacillus simplex* 237 strain deposited with NRRL as Accession No. B-50969.

Other aspects of the present disclosure relate to a method of increasing resistance to fungal growth in a plant, by growing the plant in the presence of a strain having all the identifying characteristics of a *Bacillus subtilis* 30VD-1 strain deposited with NRRL as Accession No. B-50966. Other aspects of the present disclosure relate to a method of increasing resistance to fungal growth in a plant, by growing the plant in the presence of a strain having all the identifying characteristics of a *Bacillus simplex* 30N-5 strain deposited with NRRL as Accession No. B-50968. Other aspects of the present disclosure relate to a method of increasing resistance to fungal growth in a plant, by growing the plant in the presence of a strain having all the identifying characteristics of a *Bacillus simplex* 11 strain deposited with NRRL as Accession No. B-50967. Other aspects of the present disclosure relate to a method of increasing resistance to fungal growth in a plant, by growing the plant in the presence of a strain having all the identifying characteristics of a *Bacillus simplex* 237 strain deposited with NRRL as Accession No. B-50969.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 2A depicts *B. simplex* grown on LB with Chrome Azurol S overlay. FIG. 2B depicts *B. simplex* grown on TY with Chrome Azurol S overlay. The black arrows indicate *B. simplex* 30N-5. The white arrows indicate *B. subtilis* BAL218. The halos indicate siderophore production. FIG. 2C depicts CAS assay for *B. subtilis*

30VD-1. FIG. 2D depicts the ability of *B. subtilis* 30VD-1 to degrade rock phosphate. The arrow indicates the edge of the phosphate-solubilization zone.

FIG. 4A depicts the pea root architecture of an uninoculated pea plant. FIG. 4B depicts the pea root architecture of a pea plant 2 weeks after inoculation. Scale bar indicates 1 cm.

FIG. 5 depicts changes in pea plant characteristics after inoculation with *Bacillus simplex* 30N-5 alone (*B. simplex*), *R. leguminosarum* bv. *viciae* alone (Rlv), or the combination of both in a 1:1 ratio (Rlv+*B. simplex*), all compared to uninoculated plants (Control).

FIG. 7A depicts an uninoculated control. Gus staining is mostly localized to the youngest root tips. FIG. 7B depicts pea roots inoculated with *R. leguminosarum* bv. *viciae*. The blue color is detected in the nodules (arrows) and in young root tips. FIG. 7C depicts pea roots co-inoculated with *B. simplex* and *R. leguminosarum* bv. *viciae*. In these roots, the nodules (white arrowhead) are larger and clustered at the crown of the root. Scale bar indicates 1 cm.

FIG. 8A depicts nodule primordium (black arrow) 10 days after inoculation. The white arrow points to vascular bundle. FIG. 8B depicts emergent nodule with GUS staining in the nodule meristem (m) and young vascular bundles. FIG. 8C depicts staining in the meristem (m) and most recently developed vascular bundles (arrow). FIG. 8D depicts the nodule meristem exhibiting reduced GUS activity.

FIG. 9A depicts a cluster of nodules of different ages showing GUS staining in the young vascular bundles. The red color is due to the presence of leghemoglobin. FIG. 9B depicts a very young nodule showing localization of GUS activity in the nodule meristem (m) and young vascular bundles (vb). FIG. 9C depicts loss of GUS staining in the nodule meristem (m). FIG. 9D depicts retention of some GUS staining in the meristem (m). FIG. 9E depicts branching of the vascular bundles in a more mature nodule. FIG. 9F depicts an older nodule with extensive vascular development. FIG. 9G depicts near-median plastic section of a co-inoculated nodule 26 days after inoculation originally stained for GUS, which is localized towards the apical end near the vascular bundles (arrow). The section was stained with Safranin O. Scale bar indicates 200 µm.

FIG. 11 depicts the effect of *Bacillus simplex* 30N-5 (red) and *Bacillus subtilis* 30VD-1 (green) on fungal growth.

FIG. 13A depicts the effects of water control, *Bacillus subtilis* 30VD-1, and *Bacillus simplex* 30N-5 on growth of *Fusarium oxysporum* f. sp. *conglutinans* 808 (FOC). FIG. 13B depicts the effects of water control, *Bacillus subtilis* 30VD-1, and *Bacillus simplex* 30N-5 on growth of *Fusarium oxysporum* f. sp. *matthioli* 726 (FOM). FIG. 13C depicts the effects of water control, *Bacillus subtilis* 30VD-1, and *Bacillus simplex* 30N-5 on growth of *Nectria haematococca* 77-13-4 (Nh). White arrow highlights an increase in fungal transparency adjacent to *Bacillus simplex* 30N-5, compared to a uniform fungal appearance for the uninoculated control.

FIG. 14A depicts the collection site in April. The perennial *Z. dumosum* plants dominate the desert landscape in a landscape otherwise comprised of many annual plants, which proliferate after the spring. FIG. 14B depicts a young *Z. dumosum* plant (approx. 1 year old). FIG. 14C depicts the collection site in August. FIG. 14D depicts a mature *Z. dumosum* plant after losing its leaflets in summer. The soil of the collection site is rocky.

FIG. 16 depicts a diagram of the soil sampling procedure.

FIG. 17 depicts meteorological data for the collection sites.

FIG. 19 depicts the diversity of cultivatable, isolated strains. A wide range of bacterial species were identified based on >97% similarity of 16S rRNA sequence. The bold-faced species were used for testing for various physiological traits.

FIG. 21 depicts a community-level physiological profile of the *Z. dumosum* rhizospheric soil.

DETAILED DESCRIPTION

Figure 1:
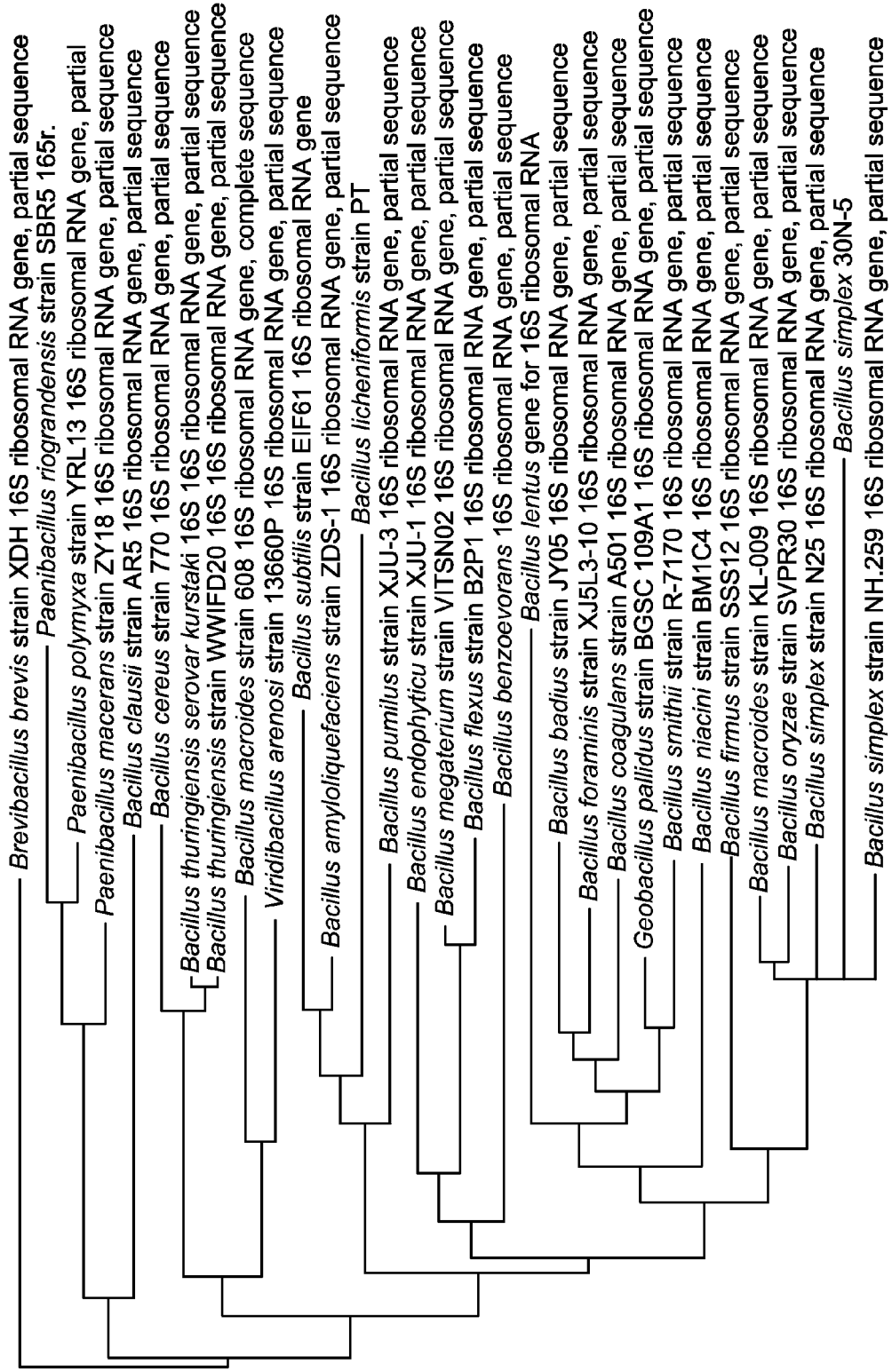
FIG. 1 depicts a phylogenetic analysis of closely related members of the genus *Bacillus* and the position of *Bacillus simplex* based on 16S RNA analysis.

The following description is presented to enable a person of ordinary skill in the art to make and use the various embodiments. Descriptions of specific compositions, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure provides methods and compositions for use in increasing one or more plant growth characteristics by growing the plant in the presence of one or more plant growth-promoting microbial isolates of the present disclosure. As used herein, "plant growth-promoting microbial isolate(s)," "PGPM isolate(s)," and "plant growth-promoting microorganism(s)" refer to isolated microbial strains, such as prokaryotes (e.g., bacteria), fungi, yeast, and the like, that are beneficial to plants. For example, such "PGPM isolate(s)" may exhibit characteristics including, without limitation, nitrogen fixation, siderophore production, iron chelation, phosphate solubilization, chitinase production, and cellulase production, that promote plant growth by increasing one or more plant growth characteristics. As used herein "plant growth characteristic(s)" refers to any plant trait associated, for example, with plant growth, development, hardiness, and yield.

The present disclosure also provides isolated plant growth-promoting microbial isolates. In certain embodiments, there is provided an isolated *Bacillus subtilis* 30VD-1 strain having all the identifying characteristics of a *Bacillus subtilis* 30VD-1 strain deposited with NRRL as Accession No. B-50966. In certain embodiments, there is provided an isolated *Bacillus simplex* 11 strain having all the identifying characteristics of a *Bacillus simplex* 11 strain deposited with NRRL as Accession No. B-50967. In certain embodiments, there is provided an isolated *Bacillus simplex* 237 strain having all the identifying characteristics of a *Bacillus simplex* 237 strain deposited with NRRL as Accession No. B-50969. The present disclosure further provides methods of increasing resistance to fungal growth in a plant, by growing the plant in the presence of a strain having all the identifying characteristics of a *Bacillus subtilis* 30VD-1 strain deposited with NRRL as Accession B-50966. The present disclosure further provides methods of increasing resistance to fungal growth in a plant, by growing the plant in the presence of a strain having all the identifying characteristics of a *Bacillus suimplex* 30N-5 strain deposited with NRRL as Accession B-50968. The present disclosure further provides methods of increasing resistance to fungal growth in a plant, by growing the plant in the presence of a strain having all the identifying characteristics of a *Bacillus suimplex* 11 strain deposited with NRRL as Accession B-50967. The present disclosure further provides methods of increasing resistance to fungal growth in a plant, by growing the plant in the presence of a strain having all the identifying characteristics of a *Bacillus suimplex* 237 strain deposited with NRRL as Accession B-50969.

Plant Growth-Promoting Microbial Isolates

Certain aspects of the present disclosure are related to compositions including one or more isolated plant growth-promoting microorganisms (e.g., microbial isolates) and methods of using such compositions for increasing one or more plant growth characteristics in plants. Any growth-promoting microorganisms may be used to increase plant growth characteristics in plants. Advantageously, microbial isolates of the present disclosure have one or more plant growth-promoting (PGP) activities that allow plants to grow in harsh environments, such as deserts. For example, microbial isolates of the present disclosure may exhibit characteristics including, without limitation, nitrogen fixation, siderophore production, iron chelation, phosphate solubilization, chitinase production, and cellulase production, that promote plant growth in plants grown under harsh environments, such as deserts. PGPM isolates of the present disclosure include, without limitation, bacteria, such as actinomycetes, firmicutes, and proteobacteria; archaea; fungi; and yeast.

Suitable plant growth-promoting microbial (PGPM) isolates of the present disclosure include, without limitation, any PGPMs isolated from the plant tissue, seeds, roots, rhizosphere, plant-associated soil samples, and/or surrounding soil samples from indigenous plants that grow in harsh environmental conditions, such as deserts, arid environments, nitrogen-poor environments, nutrient-poor environments, low pH environments, high pH environments, low temperature environments, and high temperature environments. Accordingly, in some embodiments, PGPM isolates of the present disclosure, exhibit one or more characteristics that include, without limitation, nitrogen fixation, siderophore production, iron chelation, phosphate solubilization, chitinase production, and cellulase production.

In certain embodiments, plant growth-promoting microbial (PGPM) isolates of the present disclosure include, without limitation, any PGPM isolated from the plant tissue, seeds, roots, rhizosphere, plant-associated soil samples, and/or surrounding soil samples from indigenous plants that grown in the Negev desert in Israel. In other embodiments, PGPM isolates of the present disclosure include, without limitation, any PGPM isolated from the plant tissue, seeds, roots, rhizosphere, plant-associated soil samples, and/or surrounding soil samples from the indigenous desert plants *Zygophyllum dumosum* Boiss. (Zygophyllaceae) and *Atriplex halimus* (Amaranthaceae).

Plant growth-promoting microbial isolates of the present disclosure also include, without limitation, any PGPM isolated from the plant tissue, seeds, roots, rhizosphere, plant-associated soil samples, and/or surrounding soil samples from *Podocarpus nagi* trees.

Examples of suitable PGPM isolates of the present disclosure include, without limitation, those listed in Table 1.

TABLE 1

Microbial isolates

| Microbial isolate | NRRL Accession No. |
| --- | --- |
| Bacillus subtilis 30VD-1 | B-50966 |
| Bacillus simplex 30N-5 | B-50968 |
| Bacillus simplex 11 | B-50967 |
| Bacillus simplex 237 | B-50969 |
| Arthrobacter pascens | X2 |
| Arthrobacter ramosus | X3 |
| Arthrobacter oryzae | X4 |
| Arthrobacter humicola | X5 |
| Arthrobacter oxydans | X6 |
| Arthrobacter globiformis | X7 |
| Citricoccus alkalitolerans | X8 |
| Arthrobacter aurescens | X9 |
| Arthrobacter agilis | X10 |
| Arthrobacter tumbae | X11 |
| Arthrobacter arilaitensis | X12 |
| Arthrobacter crystallopoeietes | X13 |
| Kocuria rosea | X14 |
| Arthrobacter citreus | X15 |
| Georgenia ruanii | X16 |
| Microbacterium paludicola | X17 |
| Microbacterium aerolatum | X18 |
| Microbacterium testaceum | X19 |
| Microbacterium paraoxydans | X20 |
| Microbacterium phyllosphaerae | X21 |
| Microbacterium oxydans | X22 |
| Streptomyces griseus | X23 |
| Streptomyces olivoviridis | X24 |
| Streptomyces cirratus | X25 |
| Streptomyces candidus | X26 |
| Streptomyces chryseus | X27 |
| Streptomyces peucetius | X28 |
| Streptomyces flaveus | X29 |
| Streptomyces griseoruber | X30 |
| Streptomyces bottropensis | X31 |
| Streptomyces phaeochromogenes | X32 |
| Streptomyces fradeiae | X33 |
| Streptomyces durmitorensis | X34 |
| Streptomyces coeruleofuscus | X35 |
| Streptomyces marokkonensis | X36 |
| Streptomyces althioticus | X37 |
| Streptomyces pseudogriseolus | X38 |
| Streptomyces azureus | X39 |
| Williamensia muralis | X40 |
| Mycobacterium sacrum | X41 |
| Rhodococcus jostii | X42 |
| Nocardiopsis quinghaiensis | X43 |
| Terribacillus halophilus | X44 |
| Bacillus cibi | X45 |
| Bacillus idriensis | X46 |
| Bacillus licheniformis | X47 |
| Bacillus herbersteinensis | X48 |
| Bacillus simplex | X49 |
| Staphylococcus succinus | X50 |
| Bacillus benzoevorans | X51 |
| Bacillus niacin | X52 |
| Virgibacillus halodenitrificans | X53 |
| Oceanobacillus picturae | X54 |
| Bacillus psychordurans | X55 |
| Planomicrobium okeanokoites | X56 |
| Planococcus maritimus | X57 |
| Planococcus psychrotoleratus | X58 |
| Olivibacter soli | X59 |
| Bartonella elizabethae | X60 |
| Stenotrophomonas rhizophila | X61 |
| Halomonas aquamarina | X62 |
| Pseudomonas stutzeri | X63 |
| Pseudomonas fluorescens | X64 |
| Pseudomonas brassicacearum | X65 |
| Pseudomonas frederiksbergensis | X66 |
| Aspergillus fumigatiaffinis | X67 |
| Ochroconis sp. | X68 |
| Micrococcus luteus | X69 |
| Citricoccus nitrophenolicus | X70 |
| Promicromonospora kroppenstedtii | X71 |
| Curtobacterium flaccumfaciens | X72 |
| Streptomyces halstedii | X73 |
| Paenibacillus tundrae | X74 |
| Exiguobacterium aurantiacum | X75 |
| Bacillus aquimaris | X76 |
| Planomicrobium koreense | X77 |
| Sinorhizobium medicae | X78 |
| Sinorhizobium meliloti | X79 |
| Mesorhizobium loti | X80 |
| Altererythrobacter luteolus | X81 |

TABLE 1-continued

Microbial isolates

| Microbial isolate | NRRL Accession No. |
| --- | --- |
| Massilia timonae | X82 |
| Stenotrophomonas maltophilia | X83 |
| Pseudomonas fulva | X84 |
| Pseudomonas syringae | X85 |
| Algoriphagus ratkowskyi | X86 |
| Phoma betae | X87 |
| Fusarium oxysporum | X88 |
| Cladosporium sphaerospermum | X89 |
| Alternaria thalictrigena | X90 |
| Fusarium equiseti | X91 |
| Penicillium chrysogenum | X92 |
| Penicillium commune | X93 |
| Pseudomonas putida | X94 |
| Pseudomonas plecoglossicida | X95 |
| Pseudomonas mosselii | X96 |
| Pseudomonas gessardii | X97 |
| Pseudomonas libanensis | X98 |
| Pseudomonas geniculata | X99 |

Accordingly, in certain embodiments, the PGPM isolate is an isolated *Bacillus subtilis* 30VD-1 strain having all the identifying characteristics of a *Bacillus subtilis* 30VD-1 strain deposited with NRRL as Accession No. B-50966. In other embodiments, the PGPM isolate is an isolated *Bacillus simplex* 30N-5 strain having all the identifying characteristics of a *Bacillus simplex* 30N-5 strain deposited with NRRL as Accession No. B-50968. In other embodiments, the PGPM isolate is an isolated *Bacillus simplex* 11 strain having all the identifying characteristics of a *Bacillus simplex* 11 strain deposited with NRRL as Accession No. B-50967. In other embodiments, the PGPM isolate is an isolated *Bacillus simplex* 237 strain having all the identifying characteristics of a *Bacillus simplex* 237 strain deposited with NRRL as Accession No. B-50969. In other embodiments, the PGPM isolate is an isolated plant growth-promoting microbial strain selected from the group consisting of a microbial strain having all the identifying characteristics of an *Arthrobacter pascens* strain deposited with NRRL as Accession No. X2, a microbial strain having all the identifying characteristics of an *Arthrobacter ramosus* strain deposited with NRRL as Accession No. X3, a microbial strain having all the identifying characteristics of an *Arthrobacter oryzae* strain deposited with NRRL as Accession No. X4, a microbial strain having all the identifying characteristics of an *Arthrobacter humicola* strain deposited with NRRL as Accession No. X5, a microbial strain having all the identifying characteristics of an *Arthrobacter oxydans* strain deposited with NRRL as Accession No. X6, a microbial strain having all the identifying characteristics of an *Arthrobacter globiformis* strain deposited with NRRL as Accession No. X7, a microbial strain having all the identifying characteristics of a *Citricoccus alkalitolerans* strain deposited with NRRL as Accession No. X8, a microbial strain having all the identifying characteristics of an *Arthrobacter aurescens* strain deposited with NRRL as Accession No. X9, a microbial strain having all the identifying characteristics of an *Arthrobacter agilis* strain deposited with NRRL as Accession No. X10, a microbial strain having all the identifying characteristics of an *Arthrobacter tumbae* strain deposited with NRRL as Accession No. X11, a microbial strain having all the identifying characteristics of an *Arthrobacter arilaitensis* strain deposited with NRRL as Accession No. X12, a microbial strain having all the identifying characteristics of an *Arthrobacter crystallopoeietes* strain deposited with NRRL as Accession No. X13, a microbial strain having all the identifying characteristics of a *Kocuria rosea* strain deposited with NRRL as Accession No. X14, a microbial strain having all the identifying characteristics of an *Arthrobacter citreus* strain deposited with NRRL as Accession No. X15, a microbial strain having all the identifying characteristics of a *Georgenia ruanii* strain deposited with NRRL as Accession No. X16, a microbial strain having all the identifying characteristics of a *Microbacterium paludicola* strain deposited with NRRL as Accession No. X17, a microbial strain having all the identifying characteristics of a *Microbacterium aerolatum* strain deposited with NRRL as Accession No. X18, a microbial strain having all the identifying characteristics of a *Microbacterium testaceum* strain deposited with NRRL as Accession No. X19, a microbial strain having all the identifying characteristics of a *Microbacterium paraoxydans* strain deposited with NRRL as Accession No. X20, a microbial strain having all the identifying characteristics of a *Microbacterium phyllosphaerae* strain deposited with NRRL as Accession No. X21, a microbial strain having all the identifying characteristics of a *Microbacterium oxydans* strain deposited with NRRL as Accession No. X22, a microbial strain having all the identifying characteristics of a *Streptomyces griseus* strain deposited with NRRL as Accession No. X23, a microbial strain having all the identifying characteristics of a *Streptomyces olivoviridis* strain deposited with NRRL as Accession No. X24, a microbial strain having all the identifying characteristics of a *Streptomyces cirratus* strain deposited with NRRL as Accession No. X25, a microbial strain having all the identifying characteristics of a *Streptomyces candidus* strain deposited with NRRL as Accession No. X26, a microbial strain having all the identifying characteristics of a *Streptomyces chryseus* strain deposited with NRRL as Accession No. X27, a microbial strain having all the identifying characteristics of a *Streptomyces peucetius* strain deposited with NRRL as Accession No. X28, a microbial strain having all the identifying characteristics of a *Streptomyces flaveus* strain deposited with NRRL as Accession No. X29, a microbial strain having all the identifying characteristics of a *Streptomyces griseoruber* strain deposited with NRRL as Accession No. X30, a microbial strain having all the identifying characteristics of a *Streptomyces bottropensis* strain deposited with NRRL as Accession No. X31, a microbial strain having all the identifying characteristics of a *Streptomyces phaeochromogenes* strain deposited with NRRL as Accession No. X32, a microbial strain having all the identifying characteristics of a *Streptomyces fradeiae* strain deposited with NRRL as Accession No. X33, a microbial strain having all the identifying characteristics of a *Streptomyces durmitorensis* strain deposited with NRRL as Accession No. X34, a microbial strain having all the identifying characteristics of a *Streptomyces coeruleofuscus* strain deposited with NRRL as Accession No. X35, a microbial strain having all the identifying characteristics of a *Streptomyces marokkonensis* strain deposited with NRRL as Accession No. X36, a microbial strain having all the identifying characteristics of a *Streptomyces althioticus* strain deposited with NRRL as Accession No. X37, a microbial strain having all the identifying characteristics of a *Streptomyces pseudogriseolus* strain deposited with NRRL as Accession No. X38, a microbial strain having all the identifying characteristics of a *Streptomyces azureus* strain deposited with NRRL as Accession No. X39, a microbial strain having all the identifying characteristics of a *Williamensia muralis* strain deposited with NRRL as Accession No. X40, a microbial strain having all the identifying characteristics of a *Mycobacterium sacrum* strain deposited with NRRL as Accession No. X41, a microbial strain having all the identifying characteristics of a *Rhodococcus jostii* strain deposited with NRRL as Accession No. X42, a microbial strain having all the identifying characteristics of a *Nocardiopsis quinghaiensis* strain deposited with NRRL as Accession No. X43, a microbial strain having all the identifying characteristics of a *Terribacillus halophilus* strain deposited with NRRL as Accession No. X44, a microbial strain having all the identifying characteristics of a *Bacillus cibi* strain deposited with NRRL as Accession No. X45, a microbial strain having all the identifying characteristics of a *Bacillus idriensis* strain deposited with NRRL as Accession No. X46, a microbial strain having all the identifying characteristics of a *Bacillus licheniformis* strain deposited with NRRL as Accession No. X47, a microbial strain having all the identifying characteristics of a *Bacillus herbersteinensis* strain deposited with NRRL as Accession No. X48, a microbial strain having all the identifying characteristics of a *Bacillus subtilis* 30VD-1 strain deposited with NRRL as Accession No. X49, a microbial strain having all the identifying characteristics of a *Staphylococcus succinus* strain deposited with NRRL as Accession No. X50, a microbial strain having all the identifying characteristics of a *Bacillus benzoevorans* strain deposited with NRRL as Accession No. X51, a microbial strain having all the identifying characteristics of a *Bacillus niacini* strain deposited with NRRL as Accession No. X52, a microbial strain having all the identifying characteristics of a *Virgibacillus halodenitrificans* strain deposited with NRRL as Accession No. X53, a microbial strain having all the identifying characteristics of an *Oceanobacillus picturae* strain deposited with NRRL as Accession No. X54, a microbial strain having all the identifying characteristics of a *Bacillus psychordurans* strain deposited with NRRL as Accession No. X55, a microbial strain having all the identifying characteristics of a *Planomicrobium okeanokoites* strain deposited with NRRL as Accession No. X56, a microbial strain having all the identifying characteristics of a *Planococcus maritimus* strain deposited with NRRL as Accession No. X57, a microbial strain having all the identifying characteristics of a *Planococcus psychrotoleratus* strain deposited with NRRL as Accession No. X58, a microbial strain having all the identifying characteristics of an *Olivibacter soli* strain deposited with NRRL as Accession No. X59, a microbial strain having all the identifying characteristics of a *Bartonella elizabethae* strain deposited with NRRL as Accession No. X60, a microbial strain having all the identifying characteristics of a *Stenotrophomonas rhizophila* strain deposited with NRRL as Accession No. X61, a microbial strain having all the identifying characteristics of a *Halomonas aquamarina* strain deposited with NRRL as Accession No. X62, a microbial strain having all the identifying characteristics of a *Pseudomonas stutzeri* strain deposited with NRRL as Accession No. X63, a microbial strain having all the identifying characteristics of a *Pseudomonas fluorescens* strain deposited with NRRL as Accession No. X64, a microbial strain having all the identifying characteristics of a *Pseudomonas brassicacearum* strain deposited with NRRL as Accession No. X65, a microbial strain having all the identifying characteristics of a *Pseudomonas frederiksbergensis* strain deposited with NRRL as Accession No. X66, a microbial strain having all the identifying characteristics of an *Aspergillus fumigatiaffinis* strain deposited with NRRL as Accession No. X67, a microbial strain having all the identifying characteristics of an *Ochroconis* sp. strain deposited with NRRL as Accession No. X68, a microbial strain having all the identifying characteristics of a *Micrococcus luteus* strain deposited with NRRL as Accession No. X69, a microbial strain having all the identifying characteristics of a *Citricoccus nitrophenolicus* strain deposited with NRRL as Accession No. X70, a microbial strain having all the identifying characteristics of a *Promicromonospora kroppenstedtii* strain deposited with NRRL as Accession No. X71, a microbial strain having all the identifying characteristics of a *Curtobacterium flaccumfaciens* strain deposited with NRRL as Accession No. X72, a microbial strain having all the identifying characteristics of a *Streptomyces halstedii* strain deposited with NRRL as Accession No. X73, a microbial strain having all the identifying characteristics of a *Paenibacillus tundrae* strain deposited with NRRL as Accession No. X74, a microbial strain having all the identifying characteristics of an *Exiguobacterium aurantiacum* strain deposited with NRRL as Accession No. X75, a microbial strain having all the identifying characteristics of a *Bacillus aquimaris* strain deposited with NRRL as Accession No. X76, a microbial strain having all the identifying characteristics of a *Planomicrobium koreense* strain deposited with NRRL as Accession No. X77, a microbial strain having all the identifying characteristics of a *Sinorhizobium medicae* strain deposited with NRRL as Accession No. X78, a microbial strain having all the identifying characteristics of a *Sinorhizobium meliloti* strain deposited with NRRL as Accession No. X79, a microbial strain having all the identifying characteristics of a *Mesorhizobium loti* strain deposited with NRRL as Accession No. X80, a microbial strain having all the identifying characteristics of an *Altererythrobacter luteolus* strain deposited with NRRL as Accession No. X81, a microbial strain having all the identifying characteristics of a *Massilia timonae* strain deposited with NRRL as Accession No. X82, a microbial strain having all the identifying characteristics of a *Stenotrophomonas maltophilia* strain deposited with NRRL as Accession No. X83, a microbial strain having all the identifying characteristics of a *Pseudomonas fulva* strain deposited with NRRL as Accession No. X84, a microbial strain having all the identifying characteristics of a *Pseudomonas syringae* strain deposited with NRRL as Accession No. X85, a microbial strain having all the identifying characteristics of an *Algoriphagus ratkowskyi* strain deposited with NRRL as Accession No. X86, a microbial strain having all the identifying characteristics of a *Phoma betae* strain deposited with NRRL as Accession No. X87, a microbial strain having all the identifying characteristics of a *Fusarium oxysporum* strain deposited with NRRL as Accession No. X88, a microbial strain having all the identifying characteristics of a *Cladosporium sphaerospermum* strain deposited with NRRL as Accession No. X89, a microbial strain having all the identifying characteristics of an *Alternaria thalictrigena* strain deposited with NRRL as Accession No. X90, a microbial strain having all the identifying characteristics of a *Fusarium equiseti* strain deposited with NRRL as Accession No. X91, a microbial strain having all the identifying characteristics of a *Penicillium chrysogenum* strain deposited with NRRL as Accession No. X92, a microbial strain having all the identifying characteristics of a *Penicillium commune* strain deposited with NRRL as Accession No. X93, a microbial strain having all the identifying characteristics of a *Pseudomonas putida* strain deposited with NRRL as Accession No. X94, a microbial strain having all the identifying characteristics of a *Pseudomonas plecoglossicida* strain deposited with NRRL as Accession No. X95, a microbial strain having all the identifying characteristics of a *Pseudomonas mosselii* strain deposited with NRRL as Accession No. X96, a microbial strain having all the identifying characteristics of a

*Pseudomonas gessardii* strain deposited with NRRL as Accession No. X97, a microbial strain having all the identifying characteristics of a *Pseudomonas libanensis* strain deposited with NRRL as Accession No. X98, or a microbial strain having all the identifying characteristics of a *Pseudomonas geniculata* strain deposited with NRRL as Accession No. X99.

In Table 1, the *Bacillus subtilis* 30VD-1 strain was isolated from a soil sample collected adjacent to a *Brahea edulis* palm tree growing near Los Angeles, Calif., and the *Bacillus simplex* 30N-5 strain was isolated from the rhizosphere of a *Podocarpus nagi* tree growing near Los Angeles, Calif. The *Bacillus simplex* 11 strain, the *Bacillus simplex* 237 strain, and all other strains listed in Table 1 were isolated either from *Z. dumosum* plants or *Atriplex halimus* plants indigenously growing in the Negev desert in Israel. As used herein, "isolated from" a plant refers to PGPMs isolated from plant tissue, seeds, roots, rhizosphere, plant-associated soil samples, and/or surrounding soil samples the plant.

In some embodiments, PGPM isolates of the present disclosure also include homologues, variants, and mutants of the PGPM isolates listed in Table 1. Preferably, the homologues, variants, and mutants of the PGPM isolates listed in Table 1 have all the identifying characteristics of the PGPM isolates listed in Table 1.

Additional suitable PGPM strains may be identified using the 16S rRNA sequence of the microorganisms listed in Table 1. Methods of using 16S rRNA sequences to identify similar microbial strains and species are well known in the art. Moreover, additional PGPM strains may be isolated from indigenous plants growing in harsh environments, such as the Negev desert, by any suitable means known in the art and disclosed herein. For example, the cultivation-dependent and cultivation-independent methods described herein may be used.

Methods of culturing PGPM isolates of the present disclosure are well known in the art and disclosed herein.

Microbial Consortia

In some embodiments, the plant growth-promoting compositions of the present disclosure include consortia of PGPM isolates having a mixture of two or more PGPM isolates of the present disclosure. A microbial consortium of the present disclosure may be isolated from an environmental sample such as a plant, rhizosphere, or soil sample from an indigenous plant of the Negev desert, or other harsh environment. Alternatively, a microbial consortium of the present disclosure may be rationally designed by combining known microbial strains, such as the PGPM isolates of the present disclosure. Moreover, microbial consortia of the present disclosure may further include one or more rhizobial bacterial strain. Any suitable rhizobial strain known in the art may be used.

Accordingly, in certain embodiments, a plant of the present disclosure is grown in the presence of a microbial consortium containing from two or more to 99 or more PGPM isolates of the present disclosure. In some embodiments, a plant of the present disclosure is grown in the presence of a microbial consortium containing two or more, three or more, four or more, five or more, six or more, seven or more, eight or more, nine or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 91 or more, 92 or more, 93 or more, 94 or more, 95 or more, 96 or more, 97 or more, 98 or more, or 99 or more of the PGPM isolates of the present disclosure.

In some embodiments, a plant of the present disclosure is grown in the presence of a microbial consortium containing the disclosed PGPM isolates *Arthrobacter tumbae, Kocuria rosea, Micrococcus luteus, Planococcus maritimus, Paenibacillus tundra, Bacillus simplex, Pseudomonas stutzeri*, and *Pseudomonas brassicacearum*.

In other embodiments, a plant of the present disclosure is grown in the presence of a microbial consortium containing the disclosed PGPM isolates *Arthrobacter pascens, Arthrobacter ramosus, Arthrobacter oryzae, Arthrobacter humicola, Arthrobacter oxydans, Arthrobacter globiformis, Citricoccus alkalitolerans, Arthrobacter aurescens, Arthrobacter agilis, Arthrobacter tumbae, Arthrobacter arilaitensis, Arthrobacter crystallopoeietes, Kocuria rosea, Arthrobacter citreus, Georgenia ruanii, Microbacterium paludicola, Microbacterium aerolatum, Microbacterium testaceum, Microbacterium paraoxydans, Microbacterium phyllosphaerae, Microbacterium oxydans, Streptomyces griseus, Streptomyces olivoviridis, Streptomyces cirratus, Streptomyces candidus, Streptomyces chryseus, Streptomyces peucetius, Streptomyces flaveus, Streptomyces griseoruber, Streptomyces bottropensis, Streptomyces phaeochromogenes, Streptomyces fradeiae, Streptomyces durmitorensis, Streptomyces coeruleofuscus, Streptomyces marokkonensis, Streptomyces althioticus, Streptomyces pseudogriseolus, Streptomyces azureus, Williamensia muralis, Mycobacterium sacrum, Rhodococcus jostii, Nocardiopsis quinghaiensis, Terribacillus halophilus, Bacillus cibi, Bacillus idriensis, Bacillus licheniformis, Bacillus herbersteinensis, Bacillus simplex, Staphylococcus succinus, Bacillus benzoevorans, Bacillus niacini, Virgibacillus halodenitrificans, Oceanobacillus picturae, Bacillus psychordurans, Planomicrobium okeanokoites, Planococcus maritimus, Planococcus psychrotoleratus, Olivibacter soli, Bartonella elizabethae, Stenotrophomonas rhizophila, Halomonas aquamarina, Pseudomonas stutzeri, Pseudomonas fluorescens, Pseudomonas brassicacearum, Pseudomonas frederiksbergensis, Aspergillus fumigatiaffinis, Ochroconis sp., Micrococcus luteus, Citricoccus nitrophenolicus, Promicromonospora kroppenstedtii, Curtobacterium flaccumfaciens, Streptomyces halstedii, Paenibacillus tundrae, Exiguobacterium aurantiacum, Bacillus aquimaris, Planomicrobium koreense, Sinorhizobium medicae, Sinorhizobium meliloti, Mesorhizobium loti, Altererythrobacter luteolus, Massilia timonae, Stenotrophomonas maltophilia, Pseudomonas fulva, Pseudomonas syringae, Algoriphagus ratkowskyi, Phoma betae, Fusarium oxysporum, Cladosporium sphaerospermum, Alternaria thalictrigena, Fusarium equiseti, Penicillium chrysogenum, Penicillium commune, Pseudomonas putida, Pseudomonas plecoglossicida, Pseudomonas mosselii, Pseudomonas gessardii, Pseudomonas libanensis*, and *Pseudomonas geniculata*.

Plant Growth Promoting Compositions

Other aspects of the present disclosure relate to plant growth-promoting (PGP) compositions containing one or more PGPM isolates of the present disclosure for increasing one or more plant growth characteristics in plants.

In some embodiments, the PGP composition may include from one or more to 99 or more PGPM isolates of the present disclosure. In other embodiments, the PGP composition includes one or more, two or more, three or more, four or more, five or more, six or more, seven or more, eight or more, nine or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 91 or more, 92 or more, 93 or more, 94 or more, 95 or more, 96 or more, 97 or more, 98 or more, or 99 or more of the PGPM isolates of the present disclosure.

In certain embodiments, the PGP composition may also include one or more rhizobial bacterial strain. Any suitable rhizobial strain known in the art may be used.

In order to achieve an increase in one or more plant growth characteristics, the PGP compositions of the present disclosure may also include other components or mixture of components to facilitate the viability of the PGPM isolates; inoculation of the plant, plant parts thereof, or rhizospheres; or transportation or storage of the compositions. Any suitable components known in the art may be used.

In some embodiments, the PGP compositions of the present disclosure may further contain a carrier for delivering, inoculating, or otherwise growing a plant in the presence of the composition in order to promote plant growth and productivity, such as germination, yield, and the like, by increasing one or more plant growth characteristics. Any suitable carrier known in the art may be used, including without limitation, a liquid, a solid, and a combination of a liquid and a solid carrier. In some embodiments, the liquid carrier may include water.

PGP compositions of the present disclosure may further contain components for providing additional benefits to the PGPM isolates or plants, including without limitation, an herbicide, a pesticide, a fungicide, a plant growth regulator, and an encapsulation agent, a wetting agent, a dispersing agent, and the like for enhancing the effect of the PGP composition.

Plants

Other aspects of the present disclosure relate to growing plants in the presence of one or more PGPM isolates of the present disclosure in order to increase one or more plant growth characteristics in the plant.

Plants of the present disclosure may be of any kind or from any source known in the art. For example, suitable plants of the present disclosure include, without limitation, those intended to be grown in harsh environments, such as plants grown in soils that are dry, acidic, or both; plants that are prone to infection by pathogens, such as fungi; plants grown in a desert or arid environment; plant grown in nitrogen-poor environments; plants grown in nutrient-poor environments; plants grown in low pH conditions; plants grown in high pH conditions; plants grown in low temperature conditions; and plants grown in high temperature conditions. Suitable plants of the present disclosure may be native to such harsh environments, or may plants grown in harsh environments but that are not native to such harsh environments. Suitable plants used with the compositions and methods of the present disclosure may be grown in any environment or in any growth medium, such as solid medium or liquid medium.

Suitable plants of the present disclosure include, without limitation, crop plants, energy crop plants, plants that are used in agriculture, and plants used in industrial settings. Plants of the present disclosure may be either monocotyledons or dicotyledons. For example, suitable plants of the present disclosure include, without limitation, desert plants, desert perennials, legumes, such as *Medicago sativa*, (alfalfa), *Lotus japonicus, Melilotus alba* (sweet clover), *Pisum sativum* (pea), and *Vigna unguiculata* (cowpea), *Mimosa pudica, Lupinus succulentus* (lupine), *Macroptilium atropurpureum* (siratro), *Medicago truncatula*, and *Trifolium repens* (white clover), corn, sorghum, miscanthus, sugarcane, poplar, spruce, pine, wheat, rice, soy, cotton, barley, turf grass, tobacco, potato, bamboo, rape, sugar beet, sunflower, willow, eucalyptus, *Amorphophallus* spp., *Amorphophallus konjac*, giant reed (*Arundo donax*), reed canarygrass (*Phalaris arundinacea*), *Miscanthus giganteus, Miscanthus* sp., *sericea lespedeza* (*Lespedeza cuneata*), millet, ryegrass (*Lolium multiflorum, Lolium* sp.), timothy, *Kochia* (*Kochia scoparia*), forage soybeans, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, and Kentucky bluegrass.

In certain embodiments, the plants are dicotyledons. It will be apparent to one of skill in the art that the plants of the present disclosure may also include nodulating plants. In other embodiments, the plants are desert plants, desert perennials, crop plants, or legumes. In certain embodiments, the plant are legumes, including without limitation, *Medicago sativa*, (alfalfa), *Lotus japonicus, Melilotus alba* (sweet clover), *Pisum sativum* (pea), and *Vigna unguiculata* (cowpea), *Mimosa pudica, Lupinus succulentus* (lupine), *Macroptilium atropurpureum* (siratro), *Medicago truncatula* and *Trifolium repens* (white clover).

Plant Growth Characteristics

In some embodiments, PGPM isolates of the present disclosure increase one or more plant growth characteristics of plants of the present disclosure. Plant growth characteristics of the present disclosure include, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions. As will be apparent to one of skill in the art, certain characteristics, for example nodulation, include other forms of life that interact with the plant.

As used herein, "increasing one or more plant growth characteristic" refers to increasing, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions of a plant grown in the presence of one or more PGPM isolates of the present disclosure, as compared to a corresponding plant grown under the same conditions but in the absence of the one or more PGPM isolates of the present disclosure.

In certain embodiments, growing a plant in the presence of one or more PGPM isolates of the present disclosure increases, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and/or growth under high temperature soil conditions by about 5% to about 200%, as compared to a corresponding plant grown under the same conditions but in the absence of the one or more PGPM isolates of the present disclosure. In some embodiments, growing a plant in the presence of one or more PGPM isolates of the present disclosure increases, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and/or growth under high temperature soil conditions by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, or about 200%, as compared to a corresponding plant grown under the same conditions but in the absence of the one or more PGPM isolates of the present disclosure.

In other embodiments, growing a plant in the presence of one or more PGPM isolates of the present disclosure increases, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and/or growth under high temperature soil conditions by about 2-fold to about 100-fold, as compared to a corresponding plant grown under the same conditions but in the absence of the one or more PGPM isolates of the present disclosure. In some embodiments, growing a plant in the presence of one or more PGPM isolates of the present disclosure increases, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and/or growth under high temperature soil conditions by about 2-fold, about 2.5-fold, about 3-fold, about 3.5-fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, or about 100-fold, as compared to a corresponding plant grown under the same conditions but in the absence of the one or more PGPM isolates of the present disclosure.

As disclosed herein, plant biomass and yield refer to the accumulation of plant matter in any part or all of the plant, with yield including, without limitation, the crop production of crop plants.

As disclosed herein, nodulation includes any process or quality associated with root nodule formation, including but not limited to nodule size, color, clustering, development, branching of vascular bundles, and colonization by *rhizobia*.

As disclosed herein, nitrogen and nutrient utilization include, without limitation, how well nitrogen or nutrients are taken up by the plant, the amounts of nitrogen or nutrients present in the plant, tissues thereof, or surrounding soil environment, and/or how efficiently the nitrogen or nutrients are incorporated or utilized by the plant.

As disclosed herein, resistance to pathogens or fungal growth includes, without limitation, increased plant survival upon infection with pathogen or fungal growth, a decreased growth rate or size of pathogen or fungal growth on or near the plant, or a diminished frequency with which pathogen or fungal growth appears on or near the plant.

As disclosed herein, arid conditions and arid soil conditions refer to any environment in which the plant and its immediate surroundings receive less than 50 mm of water per month. Arid conditions and arid soil conditions may also refer to any environment characterized by irregular exposure of plants to water, regardless of the total amount received.

As disclosed herein, low pH conditions and low pH soil conditions refer to any environment for plant growth with a pH of between about 0.0 to about 6.0, for example about 0.0, about 0.5, about 1.0, about 1.5, about 2.0, about 2.5, about 3.0, about 3.5, about 4.0, about 4.5, about 5.0, about 5.1, about 5.2, about 5.3, about 5.4, about 5.5, about 5.6, about 5.7, about 5.8, about 5.9, or about 6.0. High pH conditions and high pH soil conditions refer to any environment for plant growth with a pH of about 6.1 to about 14, for example about 6.1, about 6.2, about 6.3, about 6.4, about 6.5, about 6.7, about 6.8, about 6.9, about 7.0, about 7.5, about 8.0, about 8.5, about 9.0, about 9.5, about 10, about 10.5, about 11, about 11.5, about 12, about 12.5, about 13, about 13.5, or about 14.

As disclosed herein, low temperature and low temperature soil conditions refer to an ambient or soil temperature less than or equal to 15° C., for example less than or equal to −30° C., less than or equal to −25° C., less than or equal to −20° C., less than or equal to −15° C., less than or equal to −10° C., less than or equal to −9° C., less than or equal to −8° C., less than or equal to −7° C., less than or equal to −6° C., less than or equal to −5° C., less than or equal to −4° C., less than or equal to −3° C., less than or equal to −2° C., less than or equal to −1° C., less than or equal to −0° C., less than or equal to 1° C., less than or equal to 2° C., less than or equal to 3° C., less than or equal to 4° C., less than or equal to 5° C., less than or equal to 6° C., less than or equal to 7° C., less than or equal to 8° C., less than or equal to 9° C., less than or equal to 10° C., less than or equal to 11° C., less than or equal to 12° C., less than or equal to 13° C., less than or equal to 14° C., or less than or equal to 15° C. High temperature and high temperature soil conditions refer to an ambient or soil temperature greater than or equal to 50° C., for example greater than or equal to 15° C., greater than or equal to 20° C., greater than or equal to 25° C., greater than or equal to 26° C., greater than or equal to 27° C., greater than or equal to 28° C., greater than or equal to 29° C., greater than or equal to 30° C., greater than or equal to 31° C., greater than or equal to 32° C., greater than or equal to 33° C., greater than or equal to 34° C., greater than or equal to 34° C., greater than or equal to 35° C., greater than or equal to 36° C., greater than or equal to 37° C., greater than or equal to 38° C., greater than or equal to 39° C., greater than or equal to 40° C., greater than or equal to 41° C., greater than or equal to 42° C., greater than or equal to 43° C., greater than or equal to 44° C., greater than or equal to 45° C., greater than or equal to 46° C., greater than or equal to 47° C., greater than or equal to 48° C., greater than or equal to 49° C., or greater than or equal to 50° C.

Contacting and Growing Plants with Plant Growth Promoting Microbial Isolates

In some embodiments, plants are grown in the presence of PGPM isolates of the present disclosure. Any suitable method known in the art for growing plants in the presence of microorganisms and disclosed herein may be used. Moreover, any suitable method known in the art for preparing microbial isolates may be used for preparing PGPM isolated of the present disclosure for growing with plants. As disclosed herein, the PGPM isolates may be used in any state or temperature that does not adversely affect the viability of the isolates. For example, the PGPM isolates may be prepared as liquid cultures, lyophilized powders, air-dried powders, freeze-dried powders, beads, spores, aqueous slurries, gums, or prepared within soil or peat preparations.

In certain embodiments, growing a plant in the presence of one or more PGPM isolates of the present disclosure includes contacting the plant, parts thereof, seeds thereof, and/or rhizosphere thereof with one or more PGPM isolates of the present disclosure. Methods of contacting plants, parts thereof, seeds thereof, or rhizosphere thereof with microorganisms are well known in the art, and disclosed herein. Suitable methods may include, without limitation, inoculating the one or more PGPM isolates of the present disclosure into the growth medium of the plant. Exemplary growth media for plants may include, for example, soil and peat.

In some embodiments, growing a plant in the presence of one or more PGPM isolates of the present disclosure includes contacting one or more PGPM isolates of the present disclosure with plant seed. For example, plant seeds may be coated with the one or more PGPM isolates of the present disclosure, in liquid or solid suspensions, directly or in combination with any type of suitable carrier known in the art, including without limitation, any medium, suspension, powder, clay, oil, peat, and the like. Alternatively, the one or more PGPM isolates of the present disclosure may be absorbed into a granular carrier (e.g., pelleted peat) that is planted with the seed.

In other embodiments, growing a plant in the presence of one or more PGPM isolates of the present disclosure includes contacting one or more PGPM isolates of the present disclosure with a plant or part thereof. For example, the one or more PGPM isolates of the present disclosure may be added to any part of the plant, including without limitation, stems, flowers, leaves, nodes, aerial roots, and underground roots, using any suitable method known in the art. The one or more PGPM isolates of the present disclosure may be added at any time during plant growth, or in combination with any other treatment, for example, with fertilizers, pesticides, fungicides, or any combination thereof.

In further embodiments, growing a plant in the presence of one or more PGPM isolates of the present disclosure includes contacting one or more PGPM isolates of the present disclosure with plant roots or the plant rhizosphere. For example, the one or more PGPM isolates of the present disclosure may be encapsulated in beads or in any other carrier and applied to the plant roots or rhizosphere. Alternatively, the one or more PGPM isolates of the present disclosure may be added to the soil or other suitable growth medium containing the rhizosphere using any suitable method known in the art. As used herein, the plant rhizosphere may include, without limitation, roots, root nodules, root caps, root secretions, rhizosphere-associated microorganisms, and rhizosphere-associated soil.

As disclosed herein, the one or more PGPM isolates of the present disclosure may be used at any concentration or dose sufficient to increase one or more plant growth characteristics of a plant that is grown in the presence of such PGPM isolates.

In some embodiments, the plant is also grown in the presences of one or more rhizobial strains. The one or more rhizobial strains may be used in any ratio with the one or more PGPM isolates of the present disclosure that is sufficient to increase one or more plant growth characteristics of a plant that is grown in the presence of the PGPM isolates and rhizobial strains.

Deposit of Microorganisms

Table 2 lists the deposit strain name of the isolated plant growth-promoting microbial strains of the present disclosure, and the NRRL Accession number associated with each strain.

TABLE 2

| Microbial isolate | NRRL Accession No. |
|---|---|
| Bacillus subtilis 30VD-1 | B-50966 |
| Bacillus simplex 30N-5 | B-50968 |
| Bacillus simplex 11 | B-50967 |
| Bacillus simplex 237 | B-50969 |
| Arthrobacter pascens | X2 |
| Arthrobacter ramosus | X3 |
| Arthrobacter oryzae | X4 |
| Arthrobacter humicola | X5 |
| Arthrobacter oxydans | X6 |
| Arthrobacter globiformis | X7 |
| Citricoccus alkalitolerans | X8 |
| Arthrobacter aurescens | X9 |
| Arthrobacter agilis | X10 |
| Arthrobacter tumbae | X11 |
| Arthrobacter arilaitensis | X12 |
| Arthrobacter crystallopoeietes | X13 |
| Kocuria rosea | X14 |
| Arthrobacter citreus | X15 |
| Georgenia ruanii | X16 |
| Microbacterium paludicola | X17 |
| Microbacterium aerolatum | X18 |
| Microbacterium testaceum | X19 |
| Microbacterium paraoxydans | X20 |
| Microbacterium phyllosphaerae | X21 |
| Microbacterium oxydans | X22 |
| Streptomyces griseus | X23 |
| Streptomyces olivoviridis | X24 |
| Streptomyces cirratus | X25 |
| Streptomyces candidus | X26 |
| Streptomyces chryseus | X27 |
| Streptomyces peucetius | X28 |
| Streptomyces flaveus | X29 |
| Streptomyces griseoruber | X30 |
| Streptomyces bottropensis | X31 |
| Streptomyces phaeochromogenes | X32 |
| Streptomyces fradeiae | X33 |
| Streptomyces durmitorensis | X34 |
| Streptomyces coeruleofuscus | X35 |
| Streptomyces marokkonensis | X36 |
| Streptomyces althioticus | X37 |
| Streptomyces pseudogriseolus | X38 |
| Streptomyces azureus | X39 |
| Williamensia muralis | X40 |
| Mycobacterium sacrum | X41 |
| Rhodococcus jostii | X42 |
| Nocardiopsis quinghaiensis | X43 |
| Terribacillus halophilus | X44 |
| Bacillus cibi | X45 |

TABLE 2-continued

| Microbial isolate | NRRL Accession No. |
|---|---|
| Bacillus idriensis | X46 |
| Bacillus licheniformis | X47 |
| Bacillus herbersteinensis | X48 |
| Bacillus simplex | X49 |
| Staphylococcus succinus | X50 |
| Bacillus benzoevorans | X51 |
| Bacillus niacin | X52 |
| Virgibacillus halodenitrificans | X53 |
| Oceanobacillus picturae | X54 |
| Bacillus psychordurans | X55 |
| Planomicrobium okeanokoites | X56 |
| Planococcus maritimus | X57 |
| Planococcus psychrotoleratus | X58 |
| Olivibacter soli | X59 |
| Bartonella elizabethae | X60 |
| Stenotrophomonas rhizophila | X61 |
| Halomonas aquamarina | X62 |
| Pseudomonas stutzeri | X63 |
| Pseudomonas fluorescens | X64 |
| Pseudomonas brassicacearum | X65 |
| Pseudomonas frederiksbergensis | X66 |
| Aspergillus fumigatiaffinis | X67 |
| Ochroconis sp. | X68 |
| Micrococcus luteus | X69 |
| Citricoccus nitrophenolicus | X70 |
| Promicromonospora kroppenstedtii | X71 |
| Curtobacterium flaccumfaciens | X72 |
| Streptomyces halstedii | X73 |
| Paenibacillus tundrae | X74 |
| Exiguobacterium aurantiacum | X75 |
| Bacillus aquimaris | X76 |
| Planomicrobium koreense | X77 |
| Sinorhizobium medicae | X78 |
| Sinorhizobium meliloti | X79 |
| Mesorhizobium loti | X80 |
| Altererythrobacter luteolus | X81 |
| Massilia timonae | X82 |
| Stenotrophomonas maltophilia | X83 |
| Pseudomonas fulva | X84 |
| Pseudomonas syringae | X85 |
| Algoriphagus ratkowskyi | X86 |
| Phoma betae | X87 |
| Fusarium oxysporum | X88 |
| Cladosporium sphaerospermum | X89 |
| Alternaria thalictrigena | X90 |
| Fusarium equiseti | X91 |
| Penicillium chrysogenum | X92 |
| Penicillium commune | X93 |
| Pseudomonas putida | X94 |
| Pseudomonas plecoglossicida | X95 |
| Pseudomonas mosselii | X96 |
| Pseudomonas gessardii | X97 |
| Pseudomonas libanensis | X98 |
| Pseudomonas geniculata | X99 |

A deposit of each of the isolated microbial strains listed in Table 2 is maintained by The University of California, Los Angeles, having an address at 405 Hilgard Avenue, Los Angeles, Calif. 90095, United States of America. Access to these deposits will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the isolated microbial strains listed in Table 2 will be irrevocably removed by affording access to the isolated microbial strains listed in Table 2 with the Agricultural Research Service Culture Collection, (NRRL), 1815 North University Street, Peoria, Ill., 61604, USA.

The isolated microbial strains listed in Table 2 were deposited on DATE in accordance with the Budapest Treaty in the Agricultural Research Service Culture Collection, (NRRL), 1815 North University Street, Peoria, Ill., 61604, USA. The NRRL Accession number assigned for each deposited strain is listed in Table 2. Access to each deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the isolated microbial strains listed in Table 2 will be irrevocably removed.

The isolated microbial strain Bacillus subtilis 30VD-1 was deposited on Jun. 9, 2014 in accordance with the Budapest Treaty in the Agricultural Research Service Culture Collection, (NRRL), 1815 North University Street, Peoria, Ill., 61604, USA. The NRRL Accession number assigned for Bacillus subtilis 30VD-1 is B-50966. Access to the deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the isolated microbial strain Bacillus subtilis 30VD-1 will be irrevocably removed.

The isolated microbial strain Bacillus simplex 30N-5 was deposited on Jun. 9, 2014 in accordance with the Budapest Treaty in the Agricultural Research Service Culture Collection, (NRRL), 1815 North University Street, Peoria, Ill., 61604, USA. The NRRL Accession number assigned for Bacillus simplex 30N-5 is B-50968. Access to the deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the isolated microbial strain Bacillus simplex 30N-5 will be irrevocably removed.

The isolated microbial strain Bacillus simplex 11 was deposited on Jun. 9, 2014 in accordance with the Budapest Treaty in the Agricultural Research Service Culture Collection, (NRRL), 1815 North University Street, Peoria, Ill., 61604, USA. The NRRL Accession number assigned for Bacillus simplex 11 is B-50967. Access to the deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the isolated microbial strain Bacillus simplex 11 will be irrevocably removed.

The isolated microbial strain Bacillus simplex 237 was deposited on Jun. 9, 2014 in accordance with the Budapest Treaty in the Agricultural Research Service Culture Collection, (NRRL), 1815 North University Street, Peoria, Ill., 61604, USA. The NRRL Accession number assigned for Bacillus simplex 237 is B-50969. Access to the deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the isolated microbial strain Bacillus simplex 237 will be irrevocably removed.

Each of the deposited strains have been deposited under conditions that assure that access to each culture will be available during pendency of the patent application and for a period of 30 years, or 5 years after the most recent request, or for the effective life of the patent, whichever is longer. A deposit will be replaced if any of the deposits becomes nonviable during that period. Each deposit is available as required by foreign patent laws in countries wherein counterparts of the subject application, or its progeny, are filed. However, it should be understood that the availability of each deposit does not constitute a license to practice the claimed subject matter in derogation of patent rights granted by governmental action.

The following Examples are merely illustrative and are not meant to limit any aspects of the present disclosure in any way.

EXAMPLES

The following Examples describe a survey of soil bacteria isolated from the Mildred E. Mathias Botanical Garden in Los Angeles, Calif., where two *Bacillus* strains were discovered, one identified as *B. simplex* and the other as *B. subtilis*. It has been previously shown that certain *B. simplex* strains promote growth of kiwifruit (Erturk et al., 2010), *Arabidopsis* (Gutiérrez-Luna et al., 2010), and tomato and wheat (Hassen & Labuschagne, 2010), but few accounts describe this species as a plant growth-promoting microorganism (PGPM) (Ash et al., 1991; Xu & Côté, 2003; Koeppel et al., 2008). On the other hand, *B. subtilis* strains are well known PGPMs. As disclosed herein, two legume species used as models for determinate and indeterminate nodule formation, *Lotus japonicus* and *Medicago truncatula* respectively, were found to show enhanced lateral root formation in response to *B. simplex* inoculation. These results demonstrate that surveys of soil bacteria can reveal novel PGPMs. Based on these results, additional surveys were carried out to isolate novel PGPM strains. Cultivation-dependent and -independent approaches were employed to obtain an inventory of the microorganisms isolated from the Negev Desert in Israel. Functional analyses were used to determine whether the microorganisms obtained by the cultivation-dependent methods possessed traits that could make them useful as PGPMs.

Example 1

The following Example describes the isolation, identification, and characterization of two *Bacillus* strains that exhibit plant growth-promoting activity.

Materials and Methods

Routine Bacterial Growth Conditions

The *B. simplex* 30N-5 and *B. subtilis* strains were grown on LB or TY media at either 30° C. or 37° C. The rhizobial strains were grown in *Rhizobium* Defined Medium (RDM; Vincent, 1970) and prepared for inoculation as described for *B. simplex*. Antibiotics were used at the following concentrations: 50 μg/mL streptomycin (str), 10 μg/mL tetracycline (tet), and 100 μg/mL ampicillin (amp).

ACC Utilization Assay

For testing whether *B. simplex* 30N-5 could utilize ACC as a sole nitrogen (N) source, the bacteria were grown on either solid or liquid Dworkin and Foster (DF-N) minimal medium without nitrogen (Penrose & Glick, 2003). To make DF medium N-limiting, $(NH_4)_2SO_4$ was omitted and 30 μmol of ACC (Calbiochem-Novobiochem Corp., La Jolla, Calif., USA) were added. The plates were incubated for 48 h at 30° C.

IAA Detection in *B. simplex* 30N-5 Growth Medium Supernatant

To determine whether *B. simplex* produces the phytohormone IAA, the procedure of Pattern & Glick (2000) was followed. Five mL of DF salts minimal medium (Penrose & Glick, 2003) were inoculated with *B. simplex* for overnight culture. Twenty μL of this culture were transferred into 5 mL DF medium supplemented with varying concentrations of L-tryptophan (from a sterile-filtered 2 mg/mL stock prepared in warm water) at 0, 50, 100, 200, 500, 800 μg/mL, and incubated for 42 h with shaking at 37° C. The density of each culture was measured at $OD_{600}$. The cells were removed from the culture medium by centrifugation (5,500×g for 10 min), and the supernatant retained. One mL of each supernatant was mixed vigorously with 4 mL Salkowski's reagent (150 mL of concentrated $H_2SO_4$, 250 mL distilled $H_2O$, 7.5 mL 0.5M $FeCl_3.6H_2O$). The reaction proceeded at room temperature for 20 min before the absorbance at 535 nm was measured. To quantify IAA production, absorbance at 535 nm was divided by the optical density at 600 nm to take into account the variability of culture growth.

Phosphate Solubilization Assay

Pikovskaya phosphate medium (PVK) was made according to Pikovskaya (1948). For inoculation onto plates, the bacterial strains were grown in liquid medium until stationary phase at which time the cells were harvested by centrifugation (8000×g, 10 min), and the pellets washed with sterile water three times to remove any traces of the medium. The cell pellets were diluted to $OD_{600}$=0.2 in sterile water. Five μl droplets were spotted onto the plates and allowed to dry right side up for 20 min. The plates were incubated upside down at 30° C. for 10 days and the size of the clearing zone around the colony was measured. The averages and standard deviations were calculated for ca. 20 colonies of Rlv, *B. simplex*, and *B. subtilis*. The experiment was repeated three times.

Siderophore Assay

CAS agar medium devoid of nutrients was used as an indicator of siderophore presence. The components needed for a liter of the overlay medium were: 0.5 M MOPS buffer, 10 g $MgSO_4.7H_2O$, 1 g $CaCl_2.2H_2O$, 50 mL of Solution I (Chrome Azurol S (CAS) 0.065 g in 50 mL $H_2O$), 10 mL of Solution II (0.135 g $FeCl_3.2H_2O$ in 500 mL $H_2O$), 40 mL of Solution III (0.0729 g CTAB in 40 mL $H_2O$) and 9 g Bacto-Agar (Pérez-Miranda et al., 2007). Ten mL of the gel was spread as an overlay on culture plates of *B. simplex* on grown for 4 days on several solid media, including LB, TY, and BAP+N (Tzean & Torrey, 1989) medium, or over *B. simplex* and *B. subtilis* spotted onto TY plates. After a maximum period of 15 min, a color change in the blue medium was observed around the colonies. The experiment was repeated three times.

16S rRNA Gene Amplification, Purification, and Sequencing

Bacteria were suspended from a single *B. simplex* colony grown on LB plates into 20 μL of sterile-filtered water. The same procedure was used for *S. meliloti*. For *B. subtilis* 30VD-1, genomic DNA was extracted from two independent colonies and then the 16S DNA was amplified.

The 16S rRNA gene was amplified by PCR using the forward primer fD1 and the reverse primer rD1 (Weisburg et al., 1991) (Table 3). Amplification was performed in a total volume of 20 μL containing 15 μL sterile-filtered water, 2 μL of bacterial sample, 2 μL of 10× Taq Buffer ($MgCl_2$), 0.2 μL fD1 and rD1 (3.2 pmole/μL dNTPs, and 0.2 μL Taq DNA polymerase. Amplified 16S rDNA products were visualized with ethidium bromide both in the gel and in the gel electrophoresis running buffer, and purified from a 0.8% low-melting point agarose gel (100 V, 400 mA, 1 h). The gel extraction was performed with the Invitrogen Quick Gel Extraction Kit according to the manufacturer's directions.

TABLE 3

PCR primers and conditions

| Gene | Sequence | PCR Conditions | Size (bp) |
|---|---|---|---|
| 16S rRNA | fD1:<br>5'-CCGAATTCGTCGACAACAGAGTTTGATCCTGGCTCAG-3'<br>rD1:<br>5'-CCCGGGATCCAAGCTTAAGGAGGTGATCCAGCC-3' | 5 min at 95 °C., 30 cycles 30 30 sec at 94 °C., 30 sec at 55 °C., 1.5 min at 68 °C., and 10 min at 68 °C. | 832 |

To sequence the DNA fragments, the dideoxynucleotide chain-termination method was used. The sequencing reaction was performed in a total volume of 10 µL, containing 5.8 µL purified DNA, 2 µL 5× Seq buffer, 2 µL BigDye®, and 0.2 µL fD1 or rD1. The conditions were: 2 min at 96° C., 40 cycles of 10 sec at 96° C., 5 sec at 57° C., and 4 min at 60° C. DyeEx2.0 Spin Columns were used to clean the sequencing reactions. The reaction mixture was sequenced at the UCLA GenoSeq Core sequencing facility, and analyzed using the BLAST program (Altschul et al., 1990).

*Pisum sativum* Growth Experiments and GUS Staining

DR5::GUSA pea plants were inoculated with bacteria or left uninoculated (sterile water only) two days after the seeds were planted in Magenta jars. The seeds were sterilized in 50% ethanol for 5 min, in 10% commercial bleach for 10 min, and rinsed 5-10 times with sterile water before planting. *B. simplex* was grown in liquid TY until stationary phase when the cells were harvested by centrifugation (8000×g, 10 min), and the pellets washed with sterile water three times to remove the growth medium. The cell pellets were diluted to $OD_{600}$=0.2 in ¼ strength Hoagland's N-free medium (Machlis & Torrey, 1956) or sterile water. For inoculation of pea, Rlv/pHC60 (Table 4) was used. This strain was constructed via a triparental mating using the plasmid pHC60, which carries GFP (Cheng & Walker, 1998). Two mL of either *B. simplex* 30N-5 or Rlv/pHC60 were added to the Magenta jars. Co-inoculated pea plants were inoculated with 1 mL *B. simplex* 30N-5 and 1 mL Rlv/pHC60. The uninoculated control peas were watered with 2 mL of sterile water or ¼ strength Hoagland's N-free medium. Ten or more pea plants per treatment were set up per experiment, and the plants were harvested 14 dpi or later.

For GUS staining, plant roots were removed from the Magenta jars and washed to remove all perlite and vermiculite particles. Tissues were prepared as described by Jefferson (1989).

A pot growth experiment was done at a plant growth center. After sterilization, *P. sativum* DR5::GUSA seeds were planted in pots containing a perlite/vermiculite mixture topped with sterile beads to minimize contamination. *B. simplex* 30N-5, Rlv, and *B. subtilis* 30VD-1 were grown in liquid culture to a final cell density of $OD_{600}$=0.3-0.4. At germination, the plants were inoculated with 1 mL of either *B. simplex* 30N-5, Rlv, or *B. subtilis* 30VD-1. Co-inoculated pea plants were inoculated with 0.5 mL *B. simplex* 30N-5 and 0.5 mL Rlv, or with 0.5 mL *B. subtilis* 30VD-1 and 0.5 mL Rlv. The uninoculated control peas were watered with 1 mL of sterile water or ¼ strength Hoagland's N-free medium. The plants were watered every 3-4 days with 150 mL of ¼ strength Hoagland's medium (with or without nitrogen) or with sterile water, and harvested 3 weeks post inoculation.

At varying times, plants were harvested and shoot length, root length, lateral root number, nodule number (where appropriate) and dry biomass were measured.

Nodules Squashes and Microscopy

Pea roots were co-inoculated as described. Fourteen dpi or later, root nodules were surface-sterilized in 10% bleach for 10 minutes, washed with sterile water 10 times, and then squashed in 20 µl of sterile water with a sterile glass rod. The nodule squashate was diluted 1:10, 1:100, and 1:1000. Twenty µl of each dilution was spread on TY agar. The plates were incubated at 30° C.

Roots and nodules were examined directly after staining with a Zeiss Axiophot Microscope. Nodules, either singly inoculated or co-inoculated, were fixed in 4% glutaraldehyde in 0.1 M phosphate buffer (pH 6.8) and embedded in methacrylate. Plastic-embedded material was sectioned for light microscopy at 3 or 4 µm, affixed to polylysine-coated slides, and stained with 1% aqueous acid fuchsin or as described in Schwartz et al. (1989). GUS-stained nodules were also embedded in methacrylate, sectioned as described, and counter-stained with Safranin O.

Biological Control Analysis

*B. simplex* 30N-5 and the two *B. subtilis* strains were grown in liquid TY or LB. One mL of bacteria was transferred separately to autoclaved Eppendorf tubes and centrifuged at 14,000 revolutions per min (rpm) for 10 min at 22° C. The supernatant was discarded and the pellet was resuspended in sufficient sterile water to dilute the bacteria to a final cell density of $OD_{600}$=0.3-0.4.

Fifty µl of the bacterial suspension or sterile water were inoculated onto PDA, V8, or ISP2 (Atlas, 1993) agar plates and incubated at 30° C. After 0 (*B. subtilis* 30VD-1) or 24 h (*B. simplex* 30N-5 and *B. subtilis* BAL218) of incubation at 30° C., fungal plugs were placed 2.5 cm away from the site of bacterial inoculation. Measurements of fungal radial growth with a ruler were taken every 24 hours using a dissecting microscope or a Quebec® Dark-Field Colony counter. The percentage of growth inhibition was calculated using the equation: % growth inhibition=$F_C$-$F_{BS}$/$F_C$ where $F_C$=Fungus control and $F_{BS}$=Fungus inoculated with *B. simplex* or *B. subtilis* (Schmidt et al., 2009). Photos were taken with Olympus digital camera FE-370. Graphs illustrating fungal radial growth were done in Excel and standard errors were calculated.

Results

Identification of *B. simplex* 30N-5 and *B. subtilis* 30VD-1

A soil sample was collected at the base of a *Podocarpus nagi* tree (GPS coordinates: latitude 34; longitude −118) in the UCLA MEMBG (Table 4). The soil was covered with leaf litter, which was removed so that a sample could be taken within the first 2-3 cm of the soil surface. The gravimetric moisture content was approximately 20% and the pH was 5.0. Serial dilutions of the soil were plated on an agar-solidified modified BAP medium without nitrogen (Tzean & Torrey, 1989) and incubated at 30° C. for several days. Repeated streak plating of individual colonies was conducted on the same medium until purified isolates were obtained. Wet mounts were prepared and examined by phase-contrast microscopy to confirm purity. The bacteria were rod-shaped and contained endospores. The isolate was named 30N-5.

TABLE 4

Strains used in Example 1

| Strain | Relevant Characteristics |
| --- | --- |
| Bacillus simplex 30N-5 | Isolated from the rhizosphere of a Podocarpus nagi tree growing in the MEMBG. |
| Bacillus subtilis 30VD-1 | Isolated from soil in the palm section of the MEMBG, adjacent to Brahea edulis (Aracaceae Family; Guadalupe Palm), a tree indigenous to Guadalupe Island in Mexico. |
| Bacillus subtilis BAL218 | JH642 trpC2, pheA1 |
| Rm1021 | Wild-type Sinorhizobium (Ensifer) meliloti, Str$^r$ |
| Rlv128C53 | Wild-type Rhizobium leguminosarum bv. viciae |
| Rlv128C53/pHC60 | Wild-type Rhizobium leguminosarum bv. viciae with GFP, Tet$^r$ |
| PHW 808 | Isolated from cabbage; Fusarium oxysporum forma specialis conglutinans race 2 |
| PHW 726 | Isolated from Mathiola incana; Fusarium oxysporum forma specialis matthioli race 2 |
| NRRL 13993 | Isolated from maize ear, Fusarium verticillioides |
| Nectria haematococca 77-13-4 | Pea pathogen, member of the Fusarium solani complex |

To determine the identity of strain 30N-5, the 16S rRNA gene was PCR-amplified using a colony PCR procedure (see Materials and Methods section above). Phylogenetic analysis of the nucleotide sequence for a partial 16S rDNA gene shows that *B. simplex* 30N-5 is nested within a well-supported clade (100% bootstrap) that includes six other *B. simplex* strains (FIG. 1). The results indicate that strain 30N-5 is 100% identical to *Bacillus simplex* strain NH25 and >99.4% identical to all other *B. simplex* strains.

Strain 30VD-1 was isolated from soil in the palm section of the MEMBG (Table 4) and originally propagated on VXylA medium (Davis et al., 2005) in the dark at 30° C. Two 16S PCR products of 1465 and 1458 bp were sequenced and found to be 100% identical to *B. subtilis* subsp. *subtilis* strain 168.

Mechanisms by which *B. simplex* 30N-5 and *B. subtilis* 30VD-1 Promote Plant Growth The *B. simplex* isolate and two *B. subtilis* strains, a laboratory strain, *B. subtilis* BAL218, and the 30VD-1 isolate (Table 4), were tested in an iron-binding assay used to demonstrate the presence of siderophores (Pérez-Miranda et al., 2007). A color change from blue to yellow/orange illustrated by the "halo" around the colonies was observed after the 10 mL overlay of CAS was applied to the plate (FIG. 2), indicating that *B. simplex* and both *B. subtilis* strains produce siderophores that could facilitate iron assimilation into plant roots.

Figure 2:
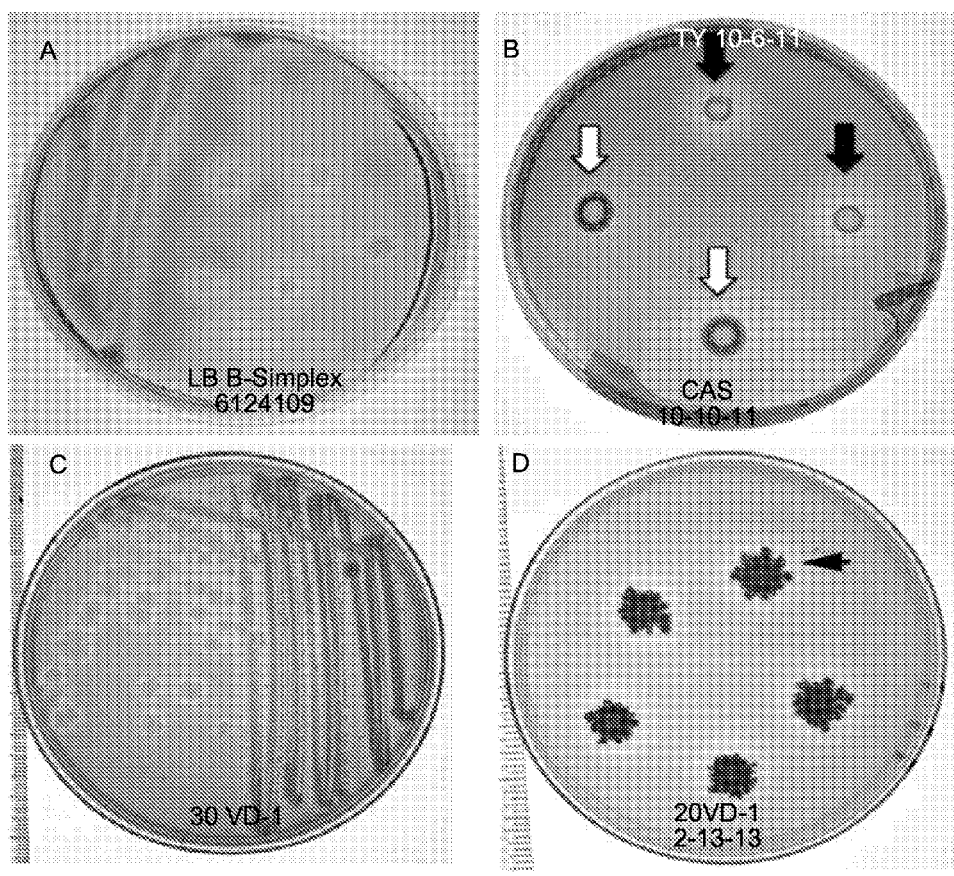
FIG. 2 depicts siderophore production and phosphate solubilization activities of *Bacillus simplex* 30N-5 and *Bacillus subtilis* 30VD-1.

Bacteria, which when grown on PVK agar containing insoluble phosphate salts, are considered phosphate solubilizers if zones of clearing form around the areas of bacterial growth. The ability of Rlv, *B. simplex* 30N-5, the laboratory strain BAL218, and *B. subtilis* 30VD-1 (FIG. 2) to solubilize phosphate was examined. If colony size is taken into account, no statistical difference was observed among the first three strains above in terms of phosphate solubilization at the experimental end point (Table 5). However, because *B. subtilis* 30VD-1 formed irregularly shaped colonies on PVK, this made it difficult to measure colony diameters accurately, and so phosphate solubilization activity was evaluated visually (FIG. 2).

TABLE 5

Diameter of Clearing Zone/Average Colony Area for Colonies Grown on PVK Medium

| Strain | Average Colony Area (mm$^2$) | Average Clearing Zone (mm$^2$) | Ratio CZ Area/ CA Area | Number of Colonies Measured |
| --- | --- | --- | --- | --- |
| Rhizobium leguminosarum bv. viciae | 11.4 ± 0.9 | 45.6 ± 2.7 | 4.2 ± 0.2 | 19 |
| B. simplex 30N-5 | 27.0 ± 0.1 | 124.4 ± 8.1 | 4.6 ± 0.3 | 17 |
| B. subtilis BAL218 | 15.9 ± 0.1 | 71.3 ± 3.7 | 4.7 ± 0.3 | 20 |

*CZ refers to average clearing zone area; CA refers to average colony area. Error bars represent standard errors.

Figure 3:
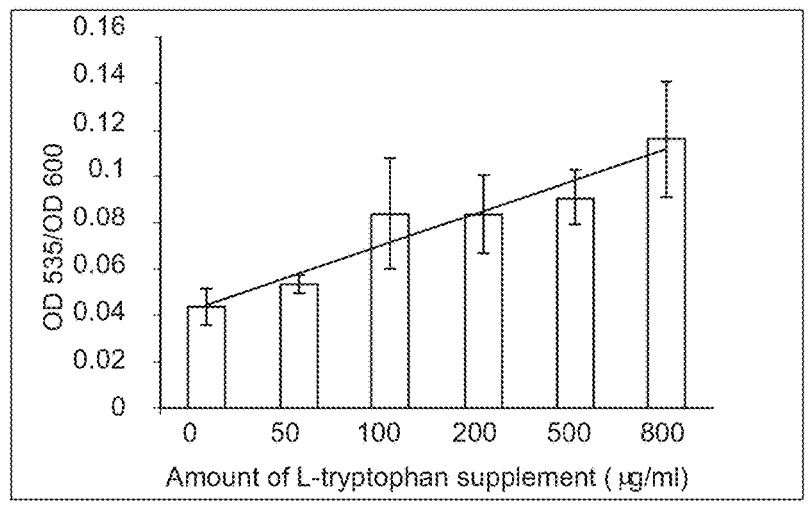
FIG. 3 depicts auxin production by *Bacillus simplex* 30N-5 following supplementation with differing amounts of L-tryptophan.

Many *B. subtilis* strains synthesize auxin (Paz et al., 2012), but few *B. simplex* strains are known to have this ability. IAA secreted into the growth medium of *B. simplex* cultures incubated with varying concentrations of L-tryptophan (an IAA precursor) was measured following published procedures (see Materials and Methods). A positive linear relationship between the concentration of L-tryptophan and the Optical Density ratio ($OD_{535/600}$) was seen indicating the presence of auxin in the supernatant (FIG. 3). No positive correlation was observed between the absorbance ratios and the varying L-tryptophan concentrations in uninoculated control experiments or in the medium alone.

Inoculation with *B. simplex* 30N-5 Alters Root Architecture

Figure 4:
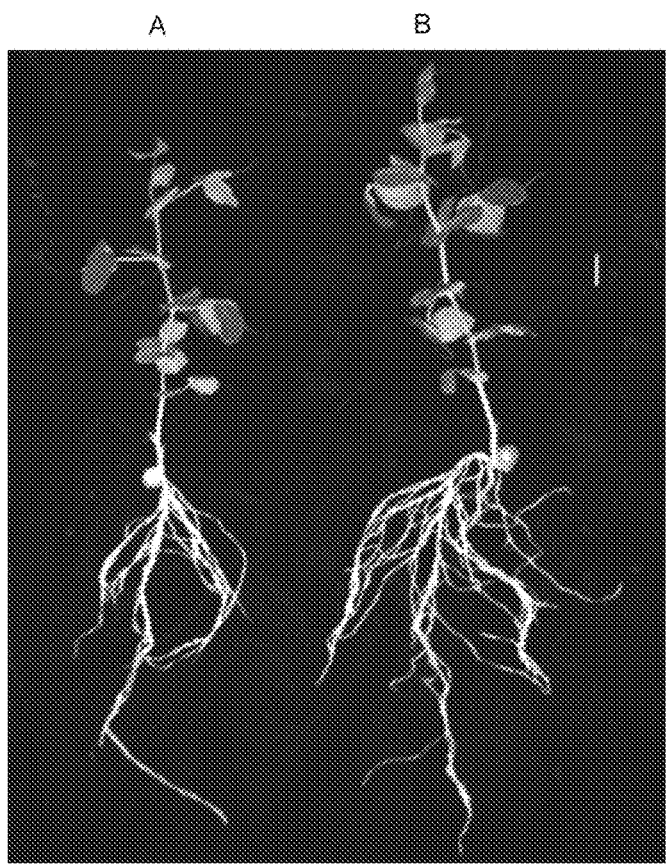
FIG. 4 depicts changes in pea root architecture for a pea plant inoculated with *Bacillus simplex* 30N-5.
Figure 5A:
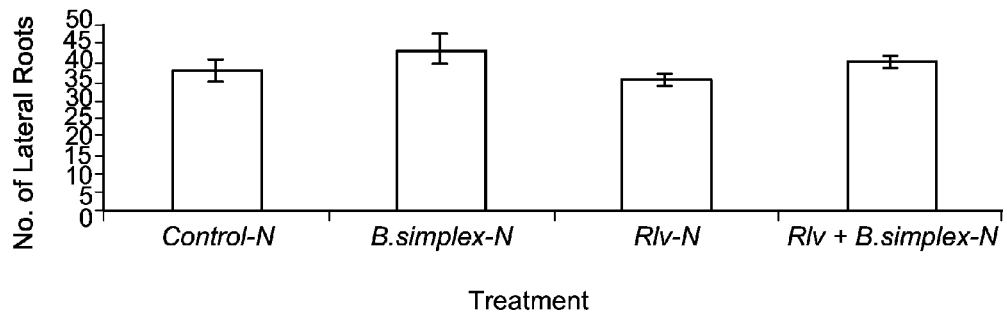
FIG. 5A depicts average number of lateral roots 14 days after inoculation.
Figure 5B:
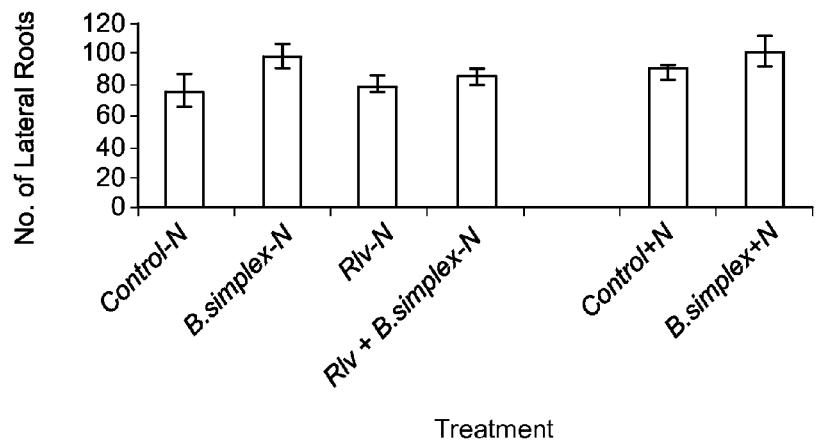
FIG. 5B depicts average number of lateral roots 18 days after inoculation.
Figure 5C:
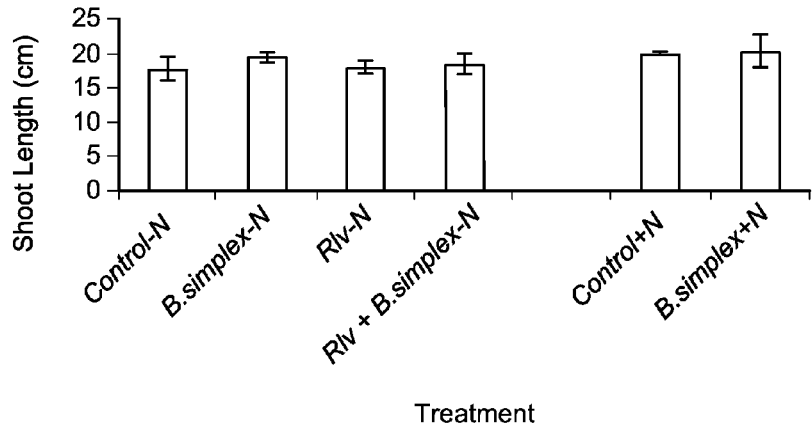
FIG. 5C depicts average shoot length 18 days after inoculation. Plants were inoculated with strains in medium lacking in nitrogen (−N) or the same medium supplemented with nitrogen (+N).

*P. sativum* plants were left uninoculated (control), inoculated with *B. simplex* or *B. subtilis* or Rlv singly, or co-inoculated with either *Bacillus* species and Rlv in a 1:1 ratio in −N medium. What was striking 14 dpi was the alteration in root architecture with *B. simplex* inoculation, typified by a statistically significant increased number of lateral roots compared to the uninoculated control or Rlv (FIGS. 4 and 5A). The increase in lateral root number in response to *B. simplex* inoculation was even more obvious 18 dpi (FIG. 5B). Plants grown in +N medium and inoculated with *B. simplex* showed a trend towards increased lateral root number, but the values were not statistically different among the treatments. With respect to shoot length, no statistical difference was observed 18 dpi (FIG. 5C).

Figure 6:
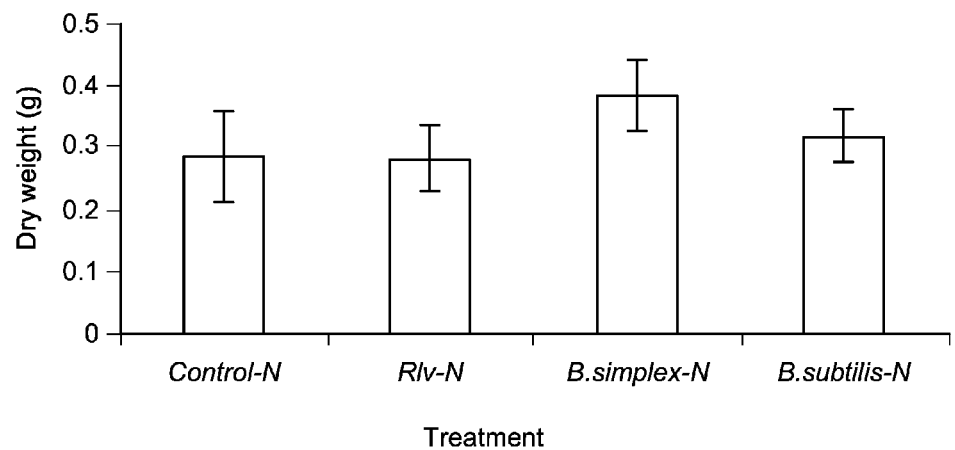
FIG. 6 depicts changes in average dry pea root biomass for plants inoculated with *Bacillus simplex* 30N-5, *Bacillus subtilis* 30VD-1, or *R. leguminosarum* bv. *viciae*, compared to uninoculated plants (Control). Inoculated peas plants were grown in pots in a greenhouse (22.3° C.) under nitrogen-deficient conditions (N−). At 18 days after inoculation, roots were isolated and dried at 55° C. for 48 h. The dried root biomass is presented as an average of multiple plants in several pots, with standard error.

Plants were grown in pots for the dry weight measurements because root volume was likely to be less constrained than in Magenta jars. The largest increase in root dry weight occurred following *B. simplex* inoculation. By contrast, *B. subtilis* and Rlv-inoculated root dry weight increases did not statistically differ from that of the uninoculated control (FIG. 6). No difference was observed among the treatments with respect to shoot dry weight.

Effects on Nodulation

Nodulation of DR5::GUS Pea in Response to *Rhizobium leguminosarum* bv. *viciae*.

Because auxin has been implicated in both nodulation and lateral root formation and because *B. simplex* secretes IAA, pea plants that contained an auxin-responsive promoter were utilized. DR5::GUS transgenic peas were originally developed by DeMason & Polowich (2009) to monitor auxin activity and response in vegetative and reproductive tissues. In these stable transgenic lines, GUS expression was detected in embryos, root tips, developing flowers, procambial cells, and pollen—sites known to correlate with high auxin concentrations.

Figure 7:
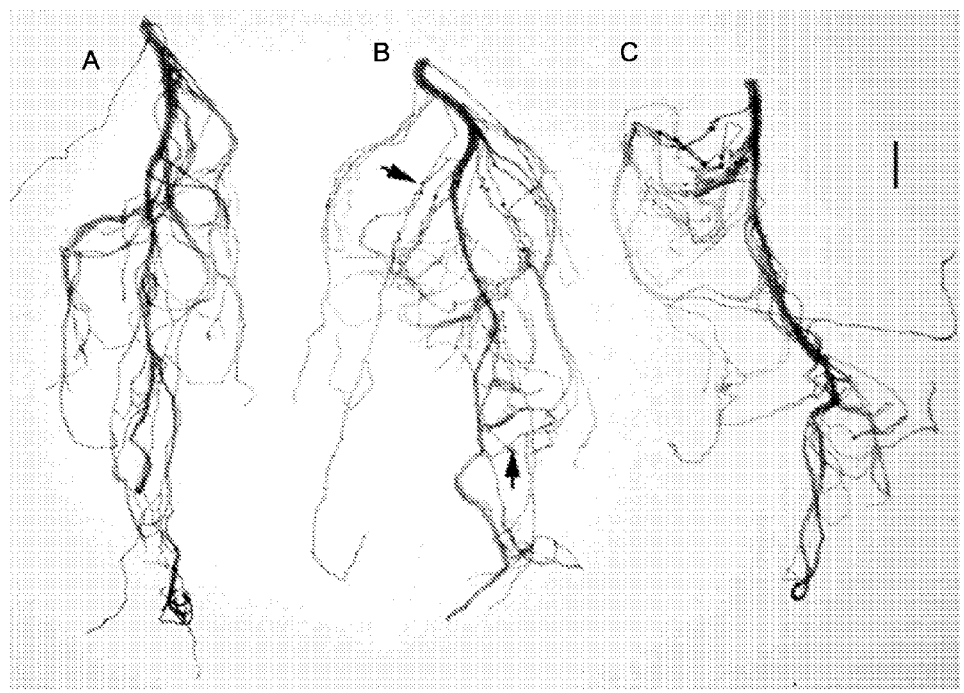
FIG. 7 depicts GUS staining in pea roots.
Figure 8:
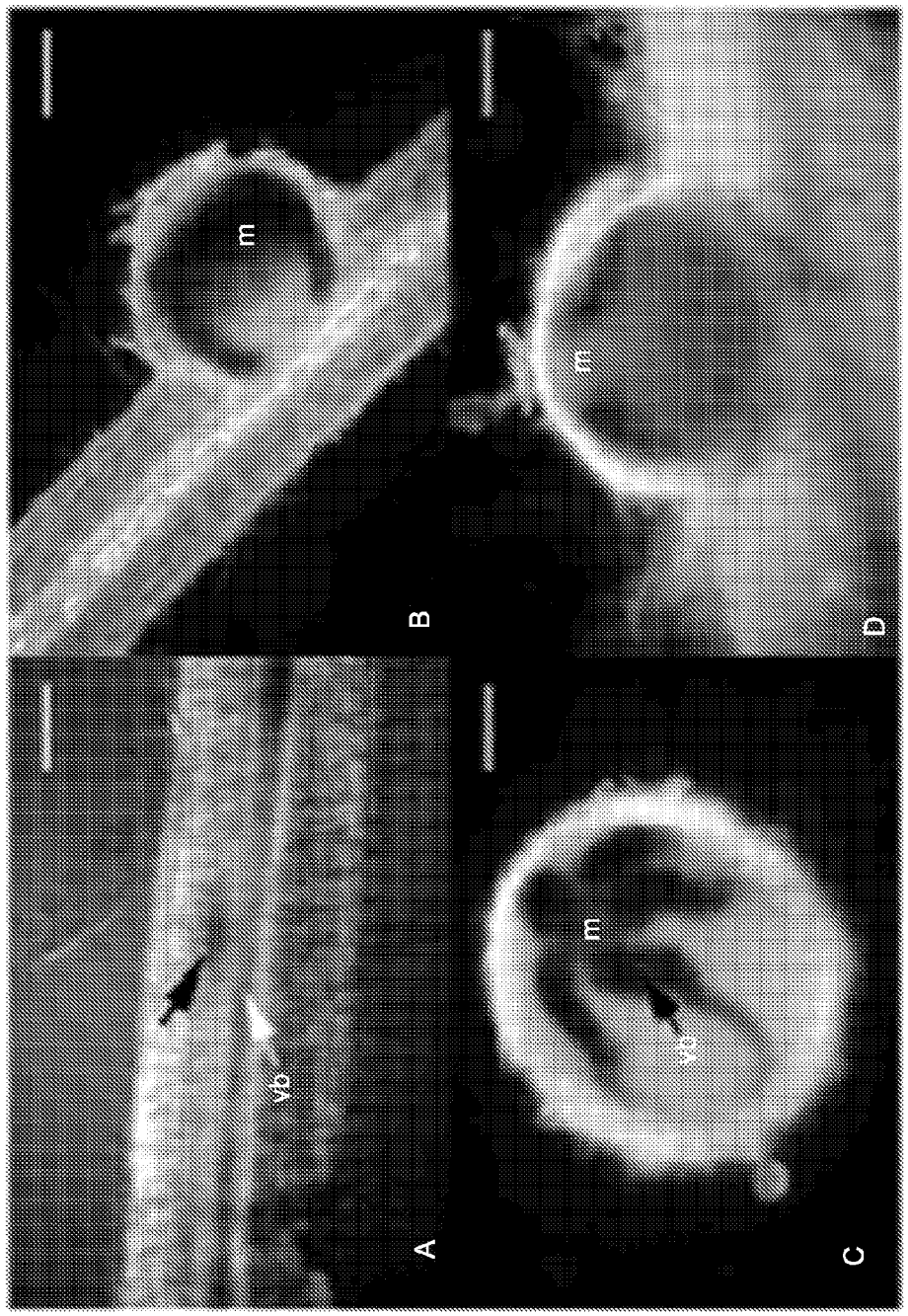
FIG. 8 depicts GUS staining in *Pisum sativum* during nodule development. Scale bar indicates 200 µm.

Because so few studies have examined *B. simplex*, strain 30N-5's influence on pea root growth and nodulation was examined. Upon inoculation with either *B. simplex* 30N-5 or Rlv individually or with Rlv and *B. simplex* together (FIG. 7), an increase in GUS expression in pea root tips over the uninoculated controls was observed. Because nodules developed after Rlv inoculation, the blue color first became associated in the inner cortex in close association to the root vascular bundle where nodules originate (FIG. 8A). Nodules of varying developmental stages that stain positively for GUS activity are illustrated in FIGS. 8B-8D. Immature but emergent nodules exhibited terminal GUS staining (FIG. 8B), which decreased as the nodules expanded (FIGS. 8C and 8D). With maturity, the staining of the nodule meristem lessened, but the GUS stain remained closely associated with the immature vascular bundles of the developing nodule.

Nodulation in Response to Co-Inoculation.

Figure 9:
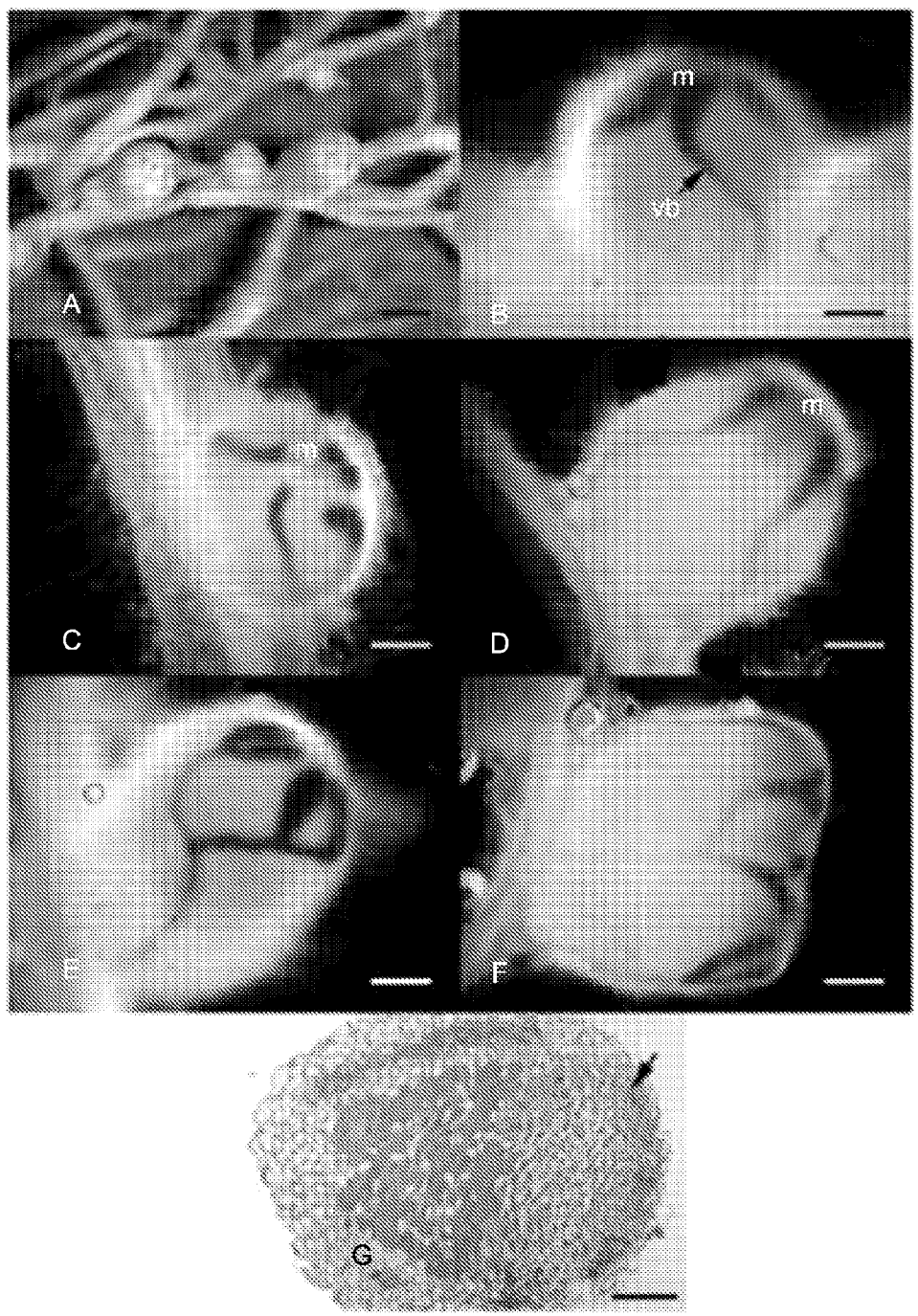
FIG. 9 depicts the effect of co-inoculation.

The most striking phenotype resulting from the co-inoculation experiments was the increase in nodule size (FIGS. 9B-9F), as well as their clustering on the lateral roots (FIG. 9A). As described above, the earliest stages of nodule development took place in the inner cortex and the young, emergent nodules exhibited GUS staining in the nodule meristem and in the vascular bundles (FIG. 9B). In some young nodules, the nodule meristem lost the blue color early in development (FIG. 9C) whereas in others, the color was evident even in the later stages (FIG. 9D). More mature nodules exhibited additional branching of the vascular bundles with the distal areas losing GUS staining as the vascular bundles matured (FIGS. 9E and 9F).

FIG. 9G illustrates a near-median, sagittal (Guinel, 2009) section of a coinoculated nodule stained for GUS (arrow). The interior cells of the nodule are occupied by bacteroids. Examination at a higher magnification did not reveal any obvious *B. simplex* in the host cells. Attempts to determine whether bacilli were present using an antibody against *Bacillus* spore walls or a specific staining reaction to identify Gram-positive organisms in sectioned material (Schwartz et al., 1989) were unsuccessful.

To determine whether both bacterial species were found in the coinoculated nodules, surface-sterilized nodules were squashed to look for Rlv/pHC60, or bacteria of a different morphology or lacking GFP. Table 6 shows the numbers of bacteria recovered from suspensions obtained from one Rlv/pHC60- and three co-inoculated, sterilized nodules. Three colonies were chosen for PCR analysis; one from an Rlv/pHC60-inoculated nodule and two from coinoculated nodules. The colony derived from the Rlv/pHC60 nodule was identified as Rlv (99% identity over 329 bp). The co-inoculated nodule colonies were identified as *Bacillus* sp. (97%; 329 bp) and *B. simplex* (99%, 890 bp). Thus, both bacterial species are housed within nodules although *B. simplex* is found in significantly fewer numbers.

Co-inoculation experiments with *B. subtilis* 30VD-1 and Rlv were performed in pots in a greenhouse. Similar to the results above, the nodules were clustered and also redder than the nodules initiated by Rlv alone.

TABLE 6

Recovery of bacteria from *R. leguminosarum* bv. viciae-inoculated and co-inoculated nodules

| Dilution | *Rhizobium*-inoculated | | Co-inoculated 1 | | Co-inoculated 2 | | Co-inoculated 3 | |
| --- | --- | --- | --- | --- | --- | --- | --- | --- |
| | Total # colonies | Non-GFP colonies | Total # colonies | Non-GFP colonies | Total # colonies | Non-GFP colonies | Total # colonies | Non-GFP colonies |
| 1:100 | 247 | 0 | n.d.* | n.d. | 435 | 1 | n.d. | n.d. |
| 1:1000 | n.d. | n.d. | 88 | 3 | 126 | 2 | 136 | 1 |

*n.d. refers to conditions with too few or too many colonies to count.

*Fusarium* Spp. Growth Inhibited by *B. subtilis* 30VD-1 and *B. simplex* 30N-5

*B. simplex* 30N-5 and the two *Bacillus* strains were tested for their ability to inhibit fungal growth. In a preliminary experiment, 10 different fungal strains were co-cultivated for 14 days on Potato Dextrose Agar (PDA) with either *B. simplex* or *B. subtilis* BAL218. The average growth of the fungus in the presence or absence of the bacterial species was measured at 24-hour intervals. *B. subtilis* BAL218 did not grow well on PDA, so Czapek Dox agar and Malt Extract agar (MEA) were also tried, but neither *B. simplex* nor *B. subtilis* BAL218 grew robustly on these media. However, *B. subtilis* 30VD-1 grew well on PDA. Hence, strain 30VD-1 was used for a second round of preliminary experiments.

Figure 10:
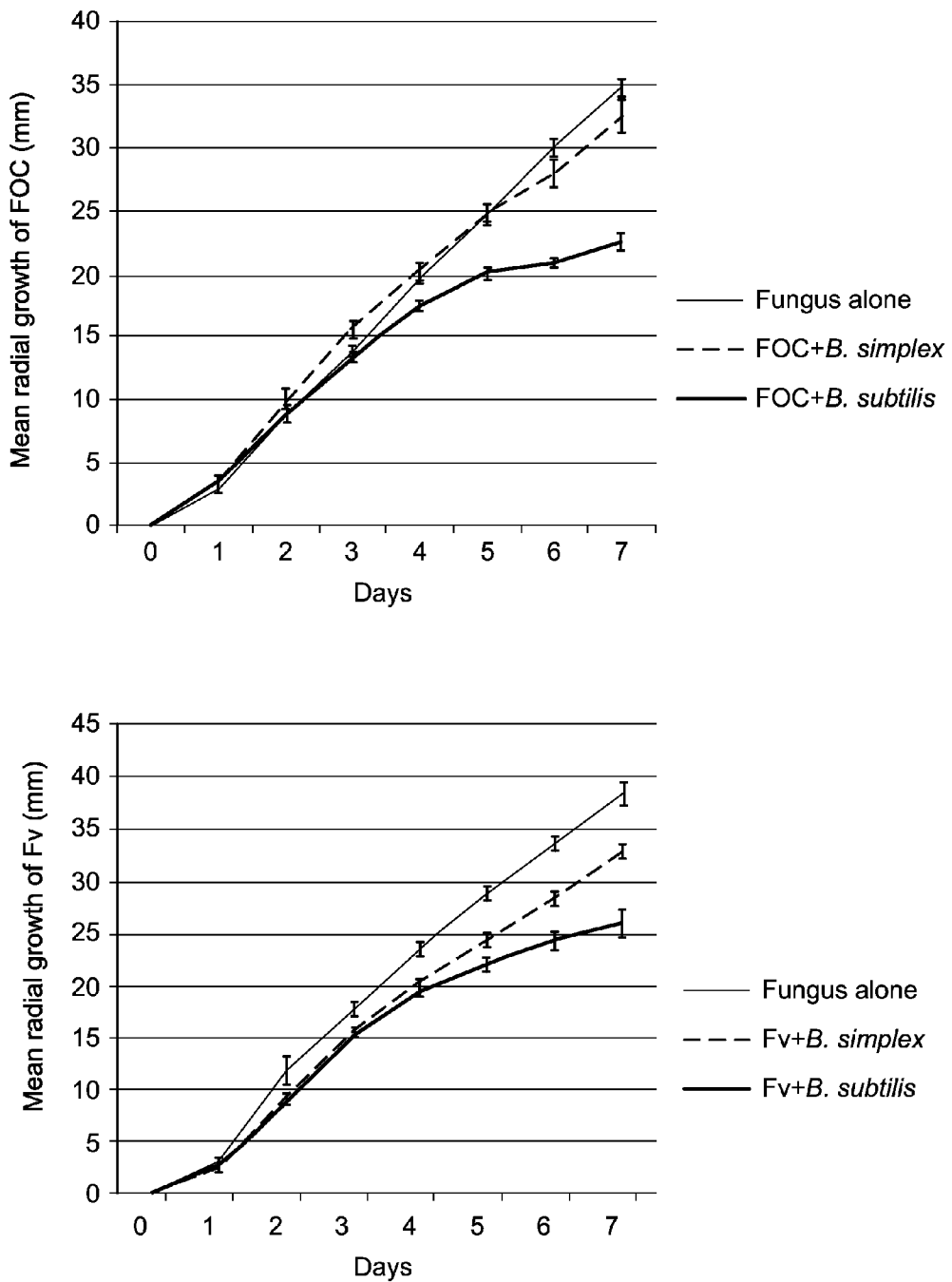
FIG. 10 depicts the effect of *Bacillus simplex* 30N-5 (red) and *Bacillus subtilis* 30VD-1 (green) on growth of *Fusarium oxysporum* f. sp. *conglutinans* 808 (FOC), top graph; and on growth of *F. verticillioides* FV3 X0042 (Fv), bottom graph, after 7 days. The blue line indicates the radial growth of each of the fungi in the absence of bacterial co-culture. The standard error for each graph is indicated.

Both *F. oxysporum f. conglutinans* 808 (FOC) and *F. verticillioides* FV3 X0042 (Fv) were studied and measurements taken every 24 hours up to 7 days after inoculation (FIG. 10). *B. subtilis* 30VD-1 significantly inhibited Fv radial growth compared to the uninoculated control whereas *B. simplex* reduced Fv growth, but not as effectively as *B. subtilis*. These data suggested that under these conditions, *B. simplex* 30N-5 is not as effective a biological control agent against *F. verticillioides* FV3 X0042 as is *B. subtilis* 30VD-1.

Figure 11A:
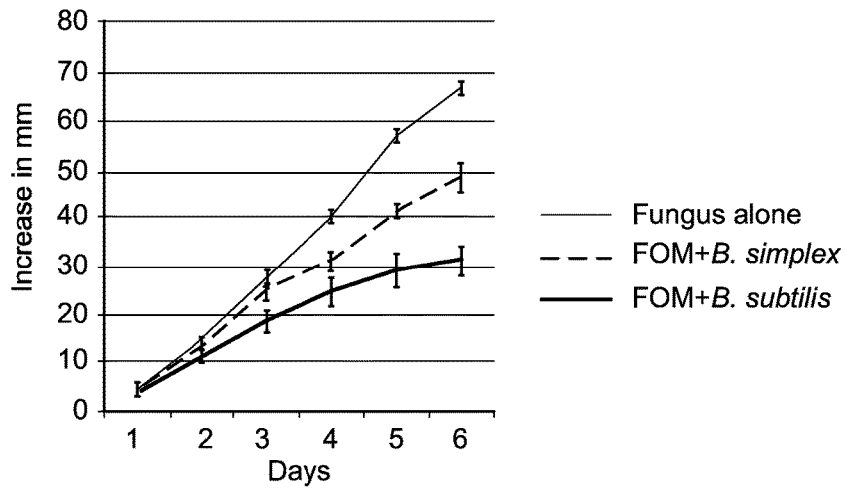
FIG. 11A depicts the effect on growth of *Fusarium oxysporum* f. sp. *matthioli* 726 (FOM).
Figure 11B:
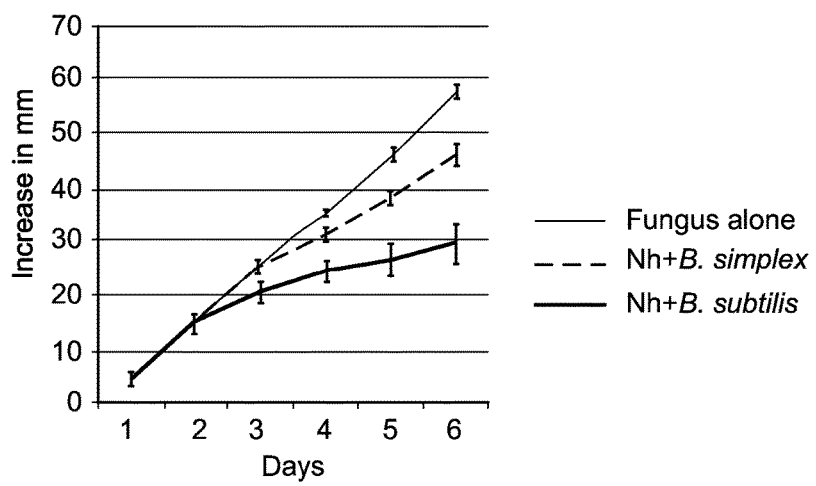
FIG. 11B depicts the effect on growth of *Nectria haematococca* 77-13-4 (Nh).

However, PDA may not support *B. simplex* growth as well as that of *B. subtilis* 30VD-1. V8 agar and solidified ISP2, both of which support bacterial and fungal growth (Miller, 1955; Taechowisan et al., 2003), were used next. In addition to FOC, *F. oxysporum f* sp. *matthioli* PHW 726 (FOM) and the pea pathogen *Nectria haematococca* 77-13-4 (Nh) were tested. *B. simplex* 30N-5 grew better on V8 medium, filtered or unfiltered, and exhibited its most active biocontrol activity on this substrate. An inhibitory effect of *B. simplex* on FOM radial expansion was apparent 72 hours after the start of the experiment and was obvious by day 4 (FIG. 11A). Nevertheless, *B. subtilis* 30VD-1 remained a more potent biological control agent, restricting fungal growth (FIG. 11B) by more than 31% compared to 9% inhibition for *B. simplex* after 3 days. By 6 days, *B. simplex* had reduced FOM radial expansion by ca. 28% whereas *B. subtilis* 30VD-1 inhibited growth by 53% (FIGS. 11A and 11B).

Figure 11C:
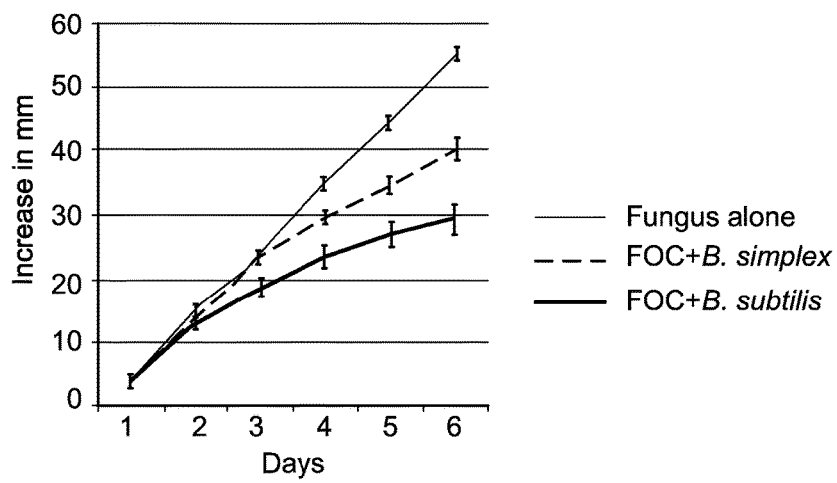
FIG. 11C depicts the effect on growth of *Fusarium oxysporum* f. sp. *conglutinans* 808 (FOC). The blue line indicates the radial growth of each of the three fungi in the absence of bacterial co-culture over a 6-day period. The standard error for each graph is indicated.
Figure 12:
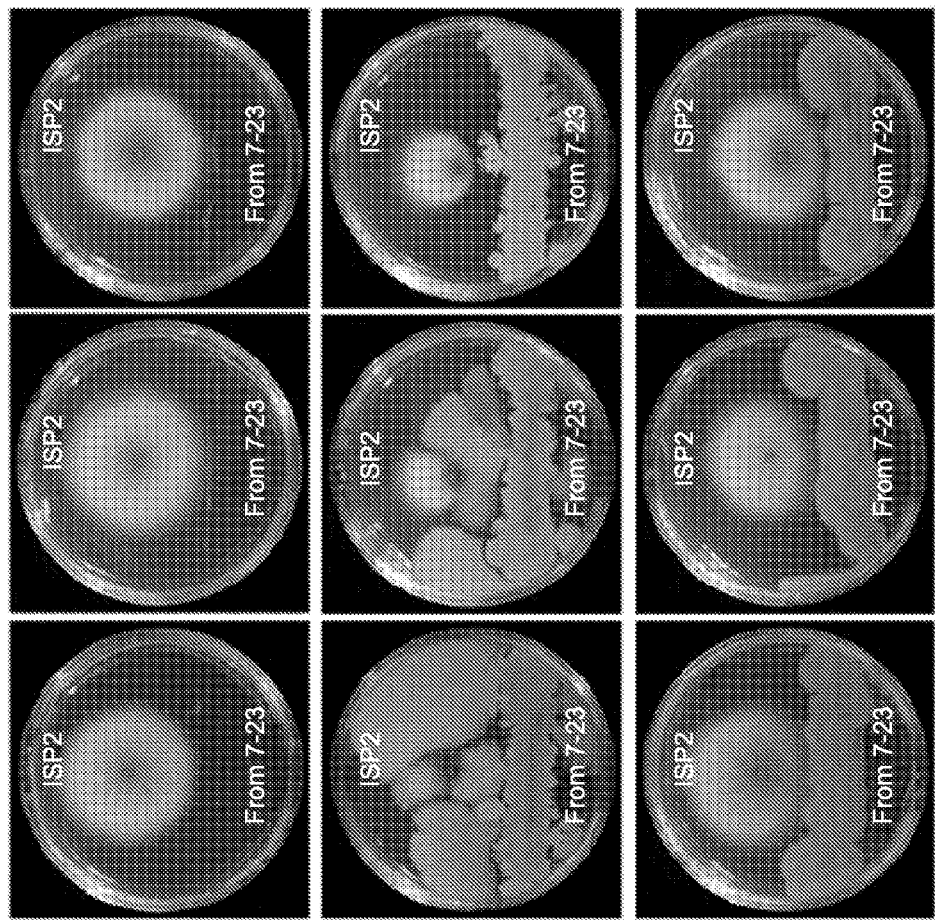
FIG. 12 depicts the response of *Fusarium oxysporum* f. sp. *matthioli* 726 (FOM) to *Bacillus simplex* 30N-5 and *Bacillus subtilis* 30VD-1 after 4 days of co-culture on IPS2 solidified medium. Three replicates of each treatment are shown.

Although FOC growth was restricted by *B. simplex* on V8 agar 4 dpi (FIG. 11C), it was not when PDA or ISP2 media (FIG. 12) were employed.

Figure 13:
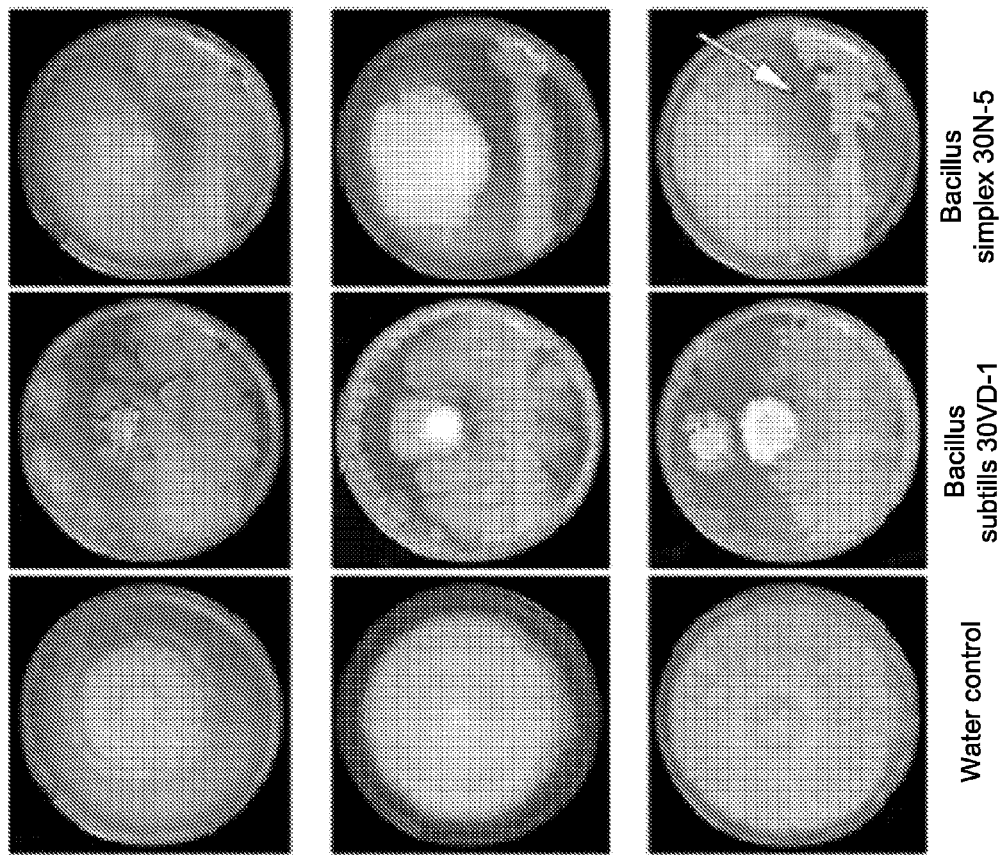
FIG. 13 depicts the effects of *Bacillus subtilis* 30VD-1 and *Bacillus simplex* 30N-5 on fungal growth.

On all media, fungal growth was curtailed by *B. subtilis* 30VD-1 cells that grew towards the fungus and eventually enveloped it. This behavior was especially obvious on ISP2 medium. However, the percentage of inhibition of FOM, Nh, and FOC growth by *B. simplex* 30N-5 on ISP2 medium (FIG. 12) was more similar to the results observed on PDA. On V8 agar, 13 days post co-cultivation (FIG. 13C), the Nh colony became almost transparent on the side adjacent to the *B. simplex* strain. This transparency was not obvious for FOM and FOC cultures even after 13 days of co-culture, although radial growth of both fungi was inhibited (FIGS. 13A and 13B). By contrast, *B. subtilis* 30VD-1 completely inhibited FOC and FOM growth after 13 days (FIGS. 13A-13C).

Discussion

As disclosed herein, two *Bacillus* strains were discovered, one described in detail herein, *Bacillus simplex* 30N-5, and a novel strain of *B. subtilis* designated 30VD-1. Because direct mechanisms of plant growth promotion are difficult to differentiate from disease suppression (Berg, 2009), it was investigated whether the *B. simplex* strain promoted plant growth by producing siderophores or solubilizing phosphate, which are two basic mechanisms of plant growth promotion. It was found that strain 30N-5 did both in contrast to *B. simplex* KBSIF-3, a strain that lacked these activities, but which nevertheless promoted wheat and tomato growth (Hassen and Labuschagne, 2010). Similarly, *B. simplex* XAS35-3 did not produce siderophores (Rashid et al. 2012). Bacterial siderophore production promotes growth by supplying iron directly to the plant or by depriving other microbes, potentially deleterious ones, of iron (Kloepper et al. 1980). Because the pea plants were grown gnotobiotically, the former explanation for growth promotion seems more likely. In addition, for *Bacillus* spp., siderophore production is believed to be the underlying mechanism for the enhancement of pigeon pea growth and nodulation in co-inoculation experiments (Rajendran et al., 2008). With increased available iron, plants undergo photosynthesis more efficiently, which positively affects plant growth and health.

In pea, co-inoculation with *Rhizobium* and *Bacillus* spp. resulted in the formation of larger, redder, and more clustered nodules. Nodule clustering following co-inoculation with Rlv and either *Bacillus* strain might be a consequence of increased root hair development as reported by Srinivasan et al. (1997) for bean, or alternatively, caused by the branching of the nodule primordium. It is well known that lateral root development is positively influenced by auxin treatment. The changes observed in pea lateral root architecture were stimulated by inoculating roots with *B. simplex* 30N-5 and *B. simplex*-secreted auxin. Auxin, when applied exogenously, increases root mass both by (1) stimulating the elongation of the primary root, and by (2) increasing the number of lateral roots (López-Bucio et al., 2007). Increased root mass is beneficial to plants because it (1) enhances their ability to anchor themselves in the soil; (2) enables the plant to obtain increased amounts of water and mineral nutrients through the increased root surface area; and (3) promotes the extension of the primary roots into deeper soil levels sooner after seed germination (Patten and Glick, 2002). The clustering of nodules and their increase in size is believed to be correlated with the increase in the number of vascular bundles observed in the co-inoculated pea nodules.

*M. truncatula* plants inoculated with *S. meliloti* 1021 either engineered to overproduce IAA (strain RD64) by introducing a plasmid encoding the indole-3-acetamide pathway or supplemented with 0.5 mM IAA exhibited increased nitrogen fixation (Bianco and Defez, 2010). This increase was linked to the improved phosphate solubilization activity of *S. meliloti* strain RD64 and IAA-supplemented strain 1021. Also, the RD64 and IAA-treated 1021 strains induced the formation of *M. truncatula* nodules that had a significantly larger nodule meristem, resulting in increased nodule size, nitrogen fixation, and stem dry weight (Imperlini et al., 2009). These nodules resemble the phenotypes observed for pea co-inoculated with Rlv and *B. simplex*, although Imperlini et al. (2009) did not report whether the nodule vasculature was more elaborated or whether the nodules were clustered together.

Biocontrol activity was also investigated for *B. simplex* 30N-5 and *B. subtilis* BAL218 and 30VD-1. Many *B. subtilis* strains are effective BCAs (Zhang J. et al., 1996), but it was found that the laboratory strain BAL218 was not. Conversely, *B. subtilis* 30VD-1 was a robust BCA, reducing fungal growth by 50% or more after 6 days of co-cultivation. However, *B. simplex* 30N-5 was not as effective a BCA as strain 30VD-1, in part because of its slower growth on many of the co-cultivation media. Nevertheless, 30N-5 limited fungal radial expansion to about one-half the level of *B. subtilis* 30VD-1, and on V8 agar, Nh fungal hyphae became transparent, most likely due to altered hyphal growth on the side adjacent to the bacteria. SEM studies observed that *Colletotrichum acutatum* hyphae appeared lysed and spores degraded in response to *B. subtilis* inoculation (Lamsal et al., 2012). In summary, both *B. simplex* 30N-5 and *B. subtilis* 30VD-1 exhibited biocontrol activity, and thus have the potential for use as BCA.

Taken together, these data strongly suggest that *B. simplex* 30N-5 is an effective PGPB on legumes and operates via a mechanism that involves biocontrol, auxin secretion, phosphate solubilization, and siderophore production.

Example 2

The following Example describes the isolation from the Negev desert in Israel, identification, and characterization of several microorganisms and microbial communities that exhibit plant growth-promoting activity.

Materials and Methods

Description of Study Sites, Sampling, and Handling Procedures

Figure 14:
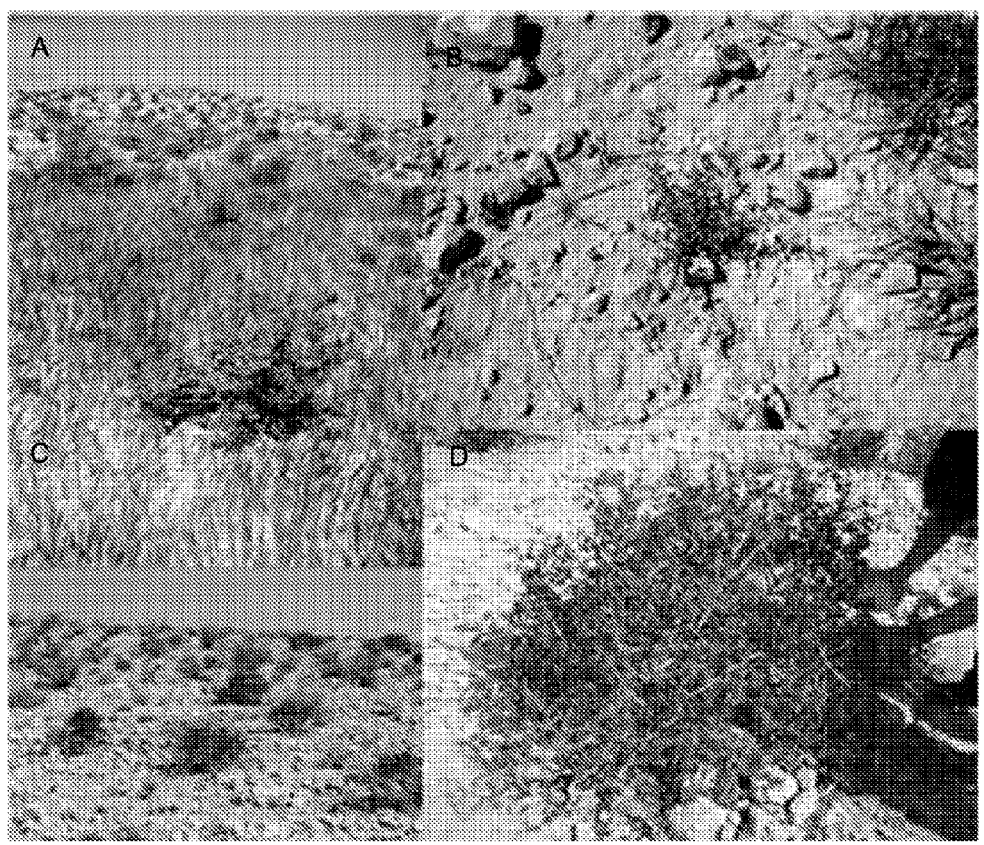
FIG. 14 depicts *Zygophyllum dumosum* Boiss. plants in the Negev desert of Israel.
Figure 15:
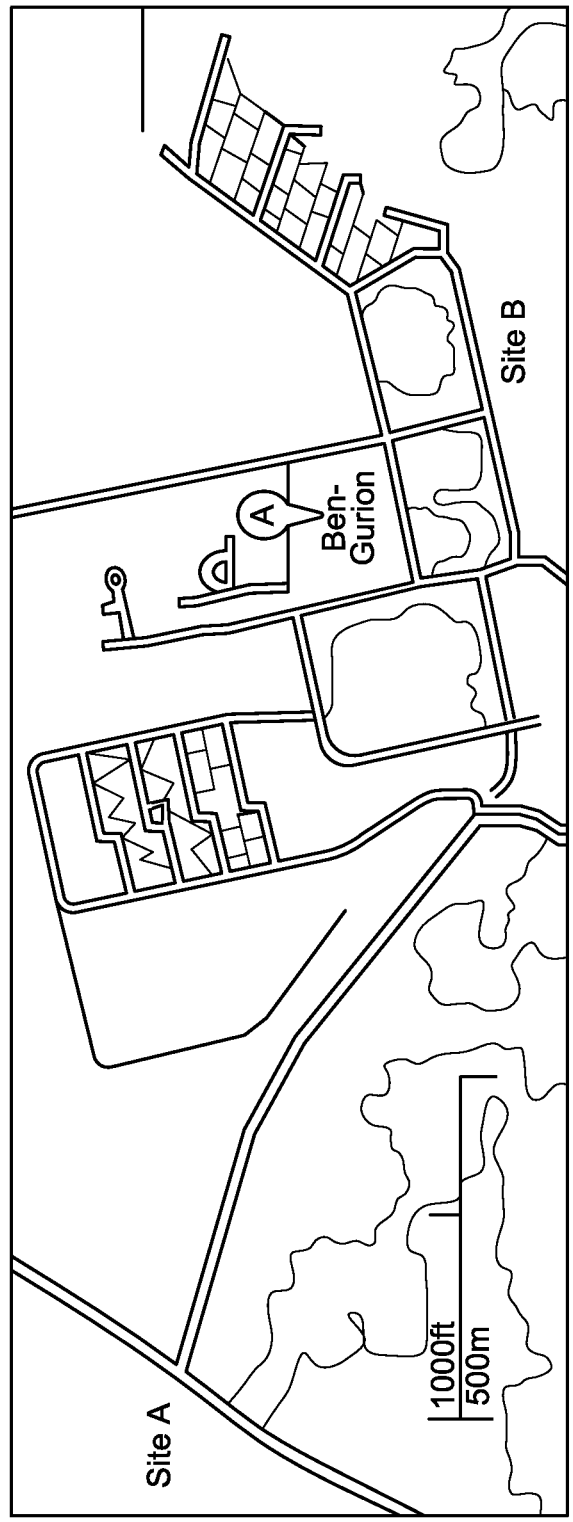
FIG. 15 depicts a map of two collection sites relative to the area of Midreshet Ben-Gurion (red shield). The first site, Site A, is a rocky slope removed from agriculture and residential communities. The second site, Site B, is a flat area having alluvial loess soil that is adjacent to a residential community and is colonized by both *Z. dumosum* and *A. halimus*.

Site A is a southeast-facing rocky slope (30°51'N 34°46'E; elevation 498 m) in the Negev desert, west of the Sede-Boqer campus of Ben Gurion University, Israel. Although the aerial distance from campus is about 2 km, because of the topography of the area, site A is disconnected from any agricultural or residential activity. The slope is dominated by the endemic perennial shrub *Z. dumosum* Boiss. (FIG. 14). Site B (Zin) is a flat area of alluvial loess soil (30°50'N 34°47'E; elevation 477 m), facing the Zin valley on the south and southeast, and is very close to the residential area of Midreshet Ben-Gurion (FIG. 15). *Z. dumosum* Boiss. and *A. halimus* are the dominant shrubs in this site. Although the two sites differ in topography, soil type, and their dominant perennial plants, the soils are poor in both environments, containing low levels of carbon and nitrogen, and have a neutral pH (for details, see Bachar et al., 2012).

Figure 16B:
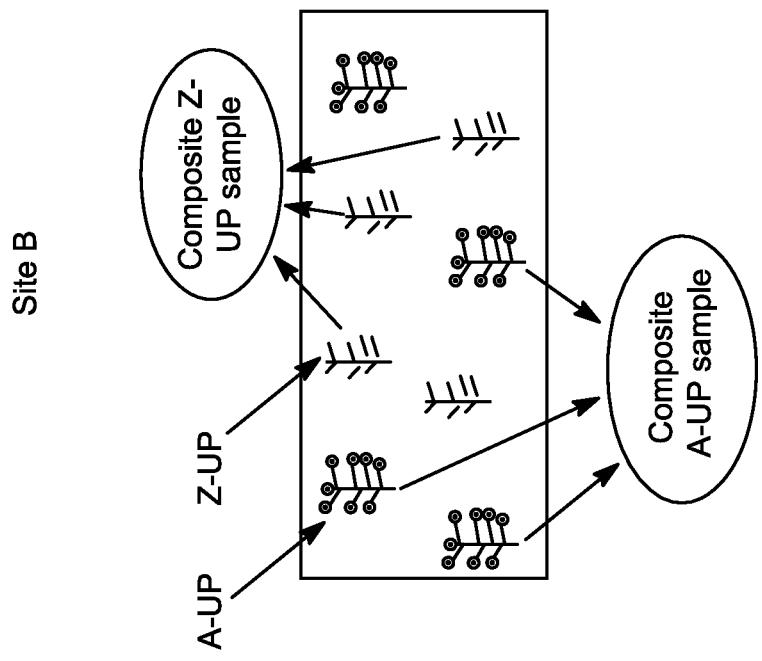
FIG. 16B depicts site B, where soil samples from under the canopy of three randomly chosen *Z. dumosum* plants (Z-UP) and three soil samples under the canopy of *A. halimus* (A-UP) were collected. The three samples from *Z. dumosum* were combined to yield a composite sample of Z-UP and those from *A. halimus* were combined to yield an A-UP composite sample.
Figure 16A:
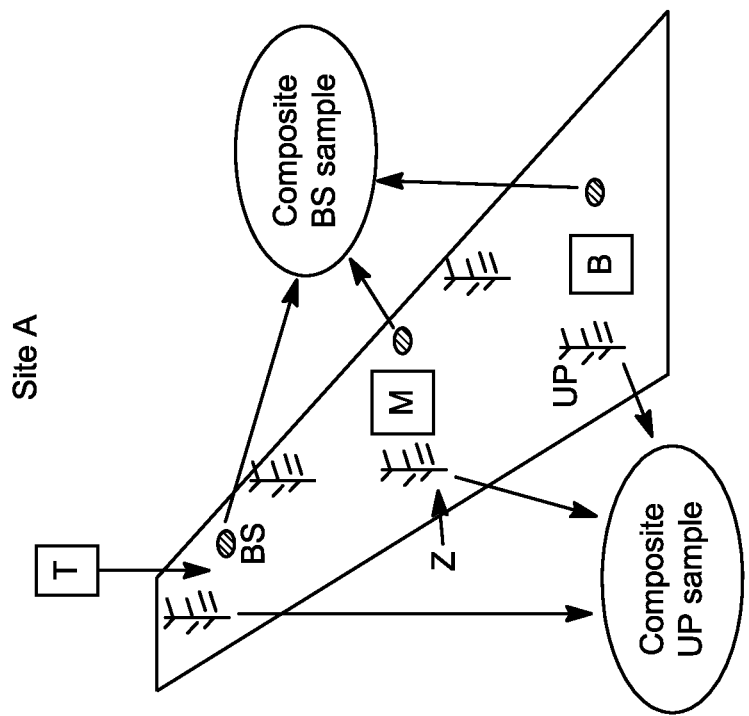
FIG. 16A depicts Site A, where three soil samples of bulk soil (BS) were collected from the top (T), middle (M), bottom (B) of the slope and combined to form a composite sample of BS. Soil samples from under the canopy of three *Z. dumosum* plants (UP) from top, middle, and bottom locations on the slope were collected and combined to form an UP composite sample.

For site A, samples under the canopy of *Z. dumosum* plants and from the open area between the shrubs (bulk soil, BS) at the bottom, middle, and top of the hill were collected from a depth of 1-10 cm under 3 different plants or areas and combined to form a composite sample (FIG. 16). The samples were collected during both the wet (November-March) and dry (April-October) seasons of the years 2009-2011. Rainfall and soil temperature data are depicted in FIG. 17. Meteorological data were obtained from the Ben Gurion University meteorology website. The samples were placed in plastic bags on ice and brought immediately to the lab for analysis. Each sample was then divided into two parts. One-half of the soil samples collected from site A was frozen and kept for eDNA (environmental DNA) extraction and identification of non-cultivatable bacteria. These samples were tripled-bagged and the root material was not removed. The second half was sieved (2 mm mesh size) to separate the root segments from the soil.

For site B, soil samples under the canopy of *Z. dumosum* and *A. halimus* plants were collected during the wet and dry seasons of 2010-2011. Soil samples collected under the canopy of 3 plants of each species were combined to form a composite soil sample, and immediately transported to the laboratory for isolation and identification of cultivatable rhizosphere bacteria (FIG. 16).

Soil Extract Preparation, Cultivation, Enumeration, and Identification of Viable Microorganisms Five grams of sieved soil sample were placed into a 250 ml Erlenmeyer flask containing 50 ml of sterile 0.02 M PBS and ten 3-4 mm glass beads. After shaking the samples vigorously by hand, they were put onto a rotary shaker for 30 min at 150 rpm. Samples removed from shaker were allowed to stand for few seconds prior to removing 1 ml from the middle of the suspension into a tube containing 9 ml of 0.02 M PBS ($10^{-2}$ dilution). The suspension was mixed thoroughly and further diluted until a $10^{-8}$ dilution end point.

Three replicates of an aliquot of 0.1 ml from dilutions $10^{-3}$ to $10^{-7}$ were plated onto a rich, non-selective medium (LB) and two selective media RDM (Vincent, 1970), a minimal medium containing sucrose, and JMV (Reis et al., 2004), which can be diagnostic for nitrogen fixation, and then incubated in the dark at 25° C. Colonies grown on each medium were counted and the number of bacteria per gram of soil was calculated. Single colonies presumed to be nitrogen fixers based on growth on JMV medium were streaked on fresh agar plates onto RDM and JMV media for 3 consecutive transfers to verify that the isolates still grew on the N-free JMV medium.

Ribotyping of the soil bacteria used for the culture-based analysis was performed by Hy Laboratories Ltd., (Rehovot, Israel), who extracted genomic DNA from a bacterial culture originating from a single colony, amplified the rRNA genes using specific primers, and then sequenced the PCR products. The sequences were then compared to several databases and the results represent the highest DNA sequence identity found for the tested samples. Ribosomal sequences of closest matching species were found in the NCBI 16S ribosomal RNA database or the NCBI non-redundant nucleotide sequence database for the cases where the closest species match was unavailable in the 16S database. The sequences were then aligned with ClustalW, and neighbor-joining phylogenetic trees (Saitou and Nei, 1987) were generated in MEGA5.1 using the p-distance model.

Isolation and Identification of Epiphytic and Endophytic Microorganisms

Root segments were washed in running tap water to remove soil particles. The roots were then placed in 10 ml sterile tubes, immersed in 3 ml sterile ddH$_2$O (double-distilled water) and vortexed. The supernatant was used to prepare 10-fold dilutions for plating in triplicate onto LB medium. Bacterial colonies detected on these plates were designated as epiphytic bacterial isolates.

Surface sterilization of root segments was done by transferring the roots to clean sterile tubes containing 95% ethanol for 30 sec, followed by soaking them in full-strength commercial bleach (5% sodium hypochlorite) for 5 min, and thoroughly rinsing 5-6 times in sterile ddH$_2$O. The surface-sterilized roots were blotted onto sterile filter paper and ground on ice with sterile ddH$_2$O (1:5, w/v). The extract was used for preparing 10-fold dilutions for plating on LB medium in triplicate. Bacterial colonies detected on these plates were designated as endophytic bacteria. To validate surface sterilization, samples of the sequential water rinses were put onto LB plates and tested for bacterial growth. All plates were kept in the dark at 25° C.

Analysis of Microbial Physiological Activities

Cellulase activity was determined according to a protocol adapted from Teather and Wood (1982). Single colonies of the selected bacterial isolates were suspended in sterile ddH$_2$O and 5 µl aliquots were spotted onto LB plates containing 0.1% carboxy methyl cellulose (CMC). Plates were incubated for 72 h at 30° C. in the dark. Cellulase activity was indicated by formation of a cleared zone after staining with Congo red (1 mg/ml) for 15 min and incubation in 1 M NaCl for 15 min followed by rinsing with 1 M HCl to make the haloes more visible.

For the phosphate solubilization assays, Pikovskaya phosphate medium (PVK: Pikovskaya, 1948) was solidified with 1.5% agar. The bacterial strains were grown in liquid Tryptone-Yeast Extract (TY) medium until stationary phase at which time the cells were harvested by centrifugation (8000×g, 10 min). After the cell pellets were washed with sterile water three times, they were diluted to an Optical Density at 600 nm (OD$_{600}$)=0.2 in sterile water. Five µl droplets were spotted onto the plates and allowed to dry right-side up for 20 min. The plates were then incubated upside down at 30° C. for 10 days and the size of the clearing zone around the colony was measured. The experiment was repeated three times and the halo diameters measured.

Siderophore producers were detected using the method described by Pérez-Miranda et al. (2007). Plates of LB or TY media were inoculated with five evenly dispersed spots containing 5 µl of bacterial suspension. After incubation for 48-72 h, the plates were overlaid with CAS medium and a change of color was observed following incubation of the plates for an additional 24-48 h.

A modification of a method for detecting cellulase activity in fungi (Smith, 1977) was used for the detection of chitinase action by the isolates. Screw cap-tubes filled with 10 ml basal medium [per L: 1.0 g (NH$_4$)$_2$SO$_4$; 0.2 g KH$_2$PO$_4$; 1.6 g K$_2$HPO$_4$; 0.2 g MgSO$_4$.7H$_2$O; 0.01 g FeSO$_4$.7H$_2$O; 0.02 g CaCO$_3$.2H$_2$O (pH 7.0+/−0.5) and 15 g agar] were sterilized and solidified. An autoclaved top agar composed of a basal medium containing chitin azure (Sigma C3020) in a final concentration of 0.08% in 10% agar was added to each tube. After the top agar solidified, each tube was inoculated with 10 µl of bacterial suspension. The tubes were incubated at 30° C. Migration of the blue dye from the top agar to the bottom agar layer indicated chitinase activity.

Isolation of Native Nodule Microorganisms

Nodules were collected from the indigenous legume *Trigonella stellata* at site A and stored over silica gel. After surface-sterilization in 95% ethanol for 1 min and 5 min in 20% commercial bleach solution, followed by 5 washes in sterile water, the individual nodules were crushed with a sterile glass rod, and the diluted suspensions were plated onto TY or Minimal Salts (MS) agar plates. After 3-7 days of incubation at 30° C., several colonies appeared. These were prepared for ribotyping.

Trap Analysis

Commonly used legume models were employed as "trap" plants to detect nitrogen-fixing bacteria (see Angus et al., 2013). Seeds were surface-sterilized in either full-strength commercial bleach for 1 h (alfalfa, lotus, sweet clover, white clover, siratro, *Mi. pudica, Me. truncatula*) or in 10% commercial bleach for 15 min (pea, cowpea) and after copious sterile water rinses were planted, depending on the seed size, in test tubes containing Jensen's agar with Hoagland's micronutrients minus N or in Magenta jars with Hoagland's minus N added to autoclaved 1:1 perlite:vermiculte. The plants were inoculated with the soil from under the *Z. dumosum* canopy from site A. After 17 or 29 days post-inoculation (dpi), nodules were isolated from alfalfa roots (the only plant to nodulate), and sterilized as described. Colonies that appeared on plates were ribotyped using 16S universal primers. To fulfill Koch's postulates, a new set of alfalfa plants was inoculated with the colonies isolated from alfalfa nodules. The nodules were surface-sterilized, squashed, plated, and ribotyped to confirm their identity.

ECO MicroPlate™ Analysis for Community-Wide Carbon Source Utilization

Soil samples from site A under the *Z. dumosum* canopy were sieved and mixed with sterile Milli-Q® water (3 g of soil with 7 ml of water) and vortexed for 2 min. The mixture was allowed to settle for 40 min and the supernatant was collected. ECO MicroPlates™ (Biolog®) were inoculated with 100 μl of the supernatant per well (using an autoclaved soil and water mixture as a negative control). The plates were incubated for 5 days at either 30° C. or room temperature and optical density readings were taken every 24 h using a microplate reader with a 595 nm filter (Bio-Rad model 680), providing an indirect measure of specific carbon source utilization by a colorimetric change due to accumulation of violet formazan. Heat maps of normalized, relative optical density in each condition were generated in R. version 2.15.2.

Cultivation-Dependent Isolation from ECO MicroPlates

Sieved desert soil samples from site A under the *Z. dumosum* canopy were incubated at 30° C. overnight, mixed with sterile water, vortexed, and allowed to settle. An aliquot of 110 μl of the supernatant was inoculated into each well on the plate and incubated for 4 days at 30° C. Cultures from selected wells were collected and processed using the same method as for 16S rRNA ribotyping (i.e., eDNA isolation, 16S PCR amplification, cloning, transformation, clone verification and sequencing). Culture selection included wells that showed a significant, intermediate, or slight colorimetric change. The cultures from the wells of three identical carbon sources from the same plate were pooled and used for eDNA isolation.

Cultivation-Independent Analysis

Negev Desert soil samples from the bottom, middle, and top of the hill (from under the plant canopy and bulk soil) from site A were sieved and stored at 4° C. Prior to isolation of eDNA, samples were incubated for 24 h at 30° C. The PowerSoil® DNA isolation kit (MoBio Laboratories) was used for the isolation of eDNA, using 0.25 g of sieved soil, according to the manufacturer's instructions with additional modifications to maximize the elimination of humic acids and other PCR inhibitors; the modifications include bead-beating, heating of samples and repeated eDNA dilutions prior to PCR. The quality of eDNA was assessed by visualization on 1% agarose gel using High DNA Mass™ Ladder (Invitrogen) as a reference. The 16S rRNA primers fD1 and rD1 (Weisburg et al., 1991) were used for amplification, and the PCR products were then verified for size on a 1% agarose gel, excised at minimal UV light exposure, and extracted from the gel using PureLink™ Quick Gel Extraction Kit (Invitrogen). Isolated PCR fragments were cloned using the pCR® 4-TOPO cloning vector and the TOPO® TA cloning kit. Transformation was done using One Shot® TOP10 chemically competent *E. coli* (Invitrogen) and the products were plated on LB/Amp/X-gal plates and incubated overnight at 37° C. White colonies were inoculated into LB/Amp broth and incubated overnight in a shaker at 37° C. Minipreps were performed using PureLink® Quick Plasmid Miniprep Kit (Invitrogen) and restriction fragment analysis confirmed the presence of the 16S fragment within the cloning vector. Verified clones were sequenced using a Biosystems 3730 Capillary DNA Analyzer.

Sequenced clones were then identified using NCBI Standard Nucleotide Basic Local Alignment Search Tool (BLAST; Altschul et al., 1990) against the NCBI 16S ribosomal RNA sequence database. Sequences of the eDNA isolates and the 16S reference sequences were aligned with ClustalW and a neighbor-joining phylogenetic tree was constructed in MEGA5.1 using the p-distance model and 1000 bootstrap replicates.

Results

Cultivation-Dependent Results

The study took place from September 2009 until August 2011 in two different sites. Site A is dominated by *Z. dumosum*, which is endemic to the Saharo-Arabian phytogeographical territories. During the wet season, the plants are green and succulent and the leaflets are actively undergoing photosynthesis (FIG. 14A). Numerous young plants, as well as ephemeral annuals, including a number of legume species, are visible in the rocky soil at this time (FIG. 14B). In the dry summer months, no other plants are visible except *Z. dumosum* plants, which after losing their leaflets utilize the evergreen petioles to photosynthesize (Terwilliger and Zeroni, 1994) (FIGS. 14C and 14D). However, for most of the dry season, the plants are not actively growing and photosynthesis is negligible. Then, as soil moisture increases, *Z. dumosum* leaflets rapidly grow out and photosynthesis is re-established (Terwilliger and Zeroni, 1994).

Figure 17A:
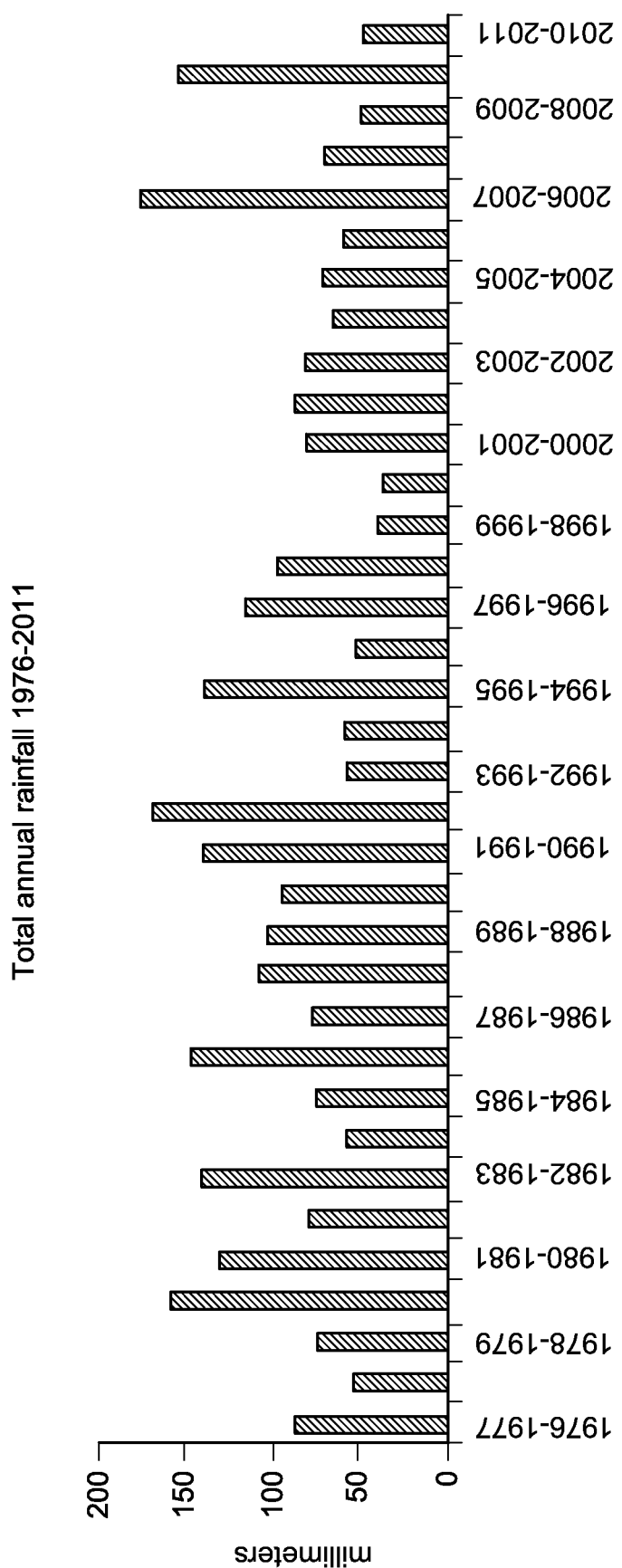
FIG. 17A depicts the total annual rainfall for a period of 35 years.
Figure 17B:
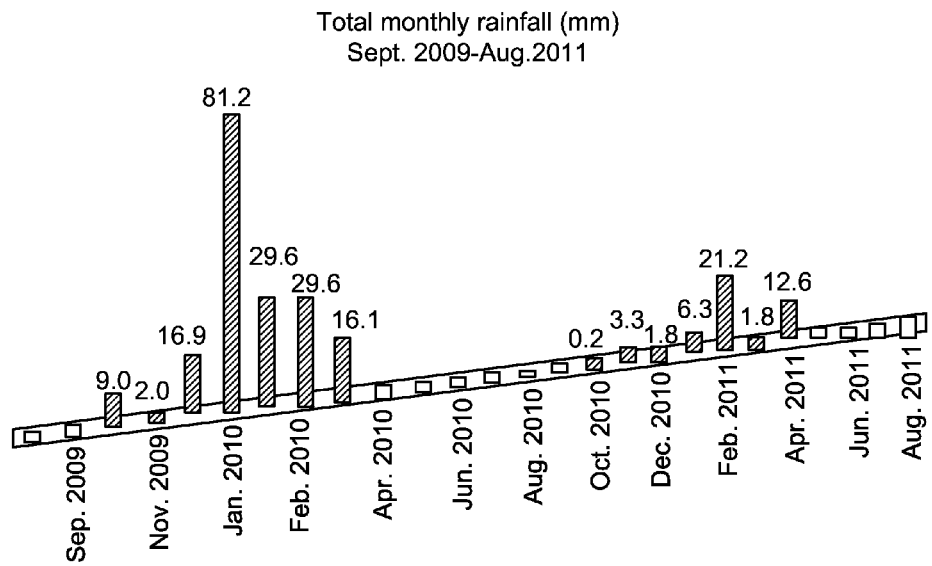
FIG. 17B depicts the total monthly rainfall (in mm) during the years of soil collection.
Figure 17C:
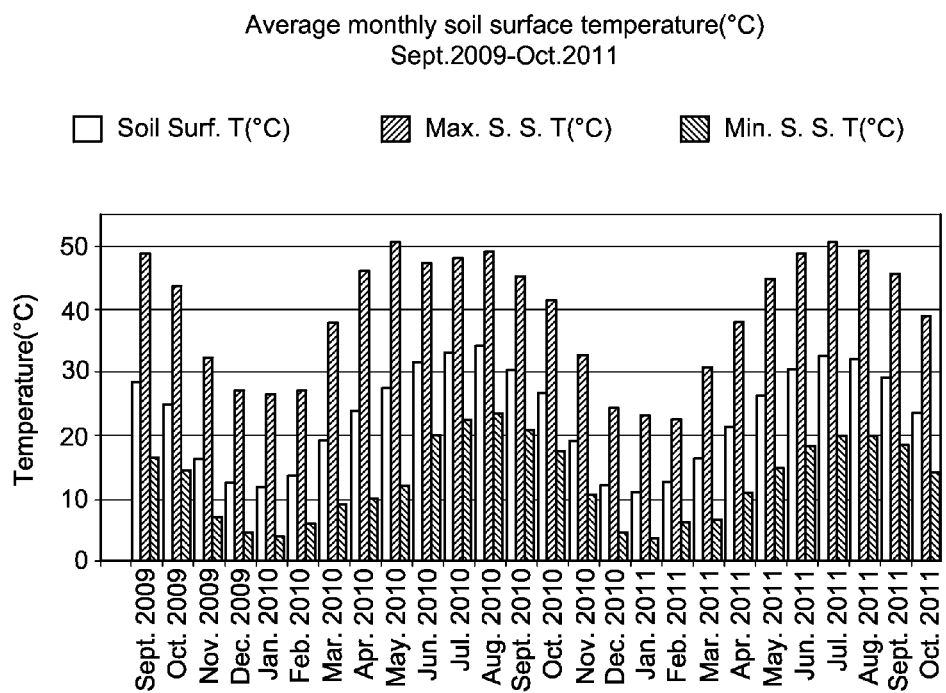
FIG. 17C depicts the average monthly soil surface temperature (° C.), as well as minimum and maximum values during the collection.

Although the average yearly rainfall in the study area is ca. 90 mm, the total rainfall spanning the first year of the collection period was 155 mm, but often significantly less rain has been measured over the years and moreover, rain does not fall evenly (FIG. 17A). For example, in 2010, ca. 50% of the annual rainfall occurred within one day in January (FIG. 17B). In the following year, rainfall dropped precipitously (total of <50 mm), during the spring season with the highest amount of rain measured at 21.2 mm in February 2011 compared to 81.2 mm in January 2010 (FIG. 17B). The January 2010 rainfall resulted in a proliferation of annual plants in the study sites.

Figure 18:
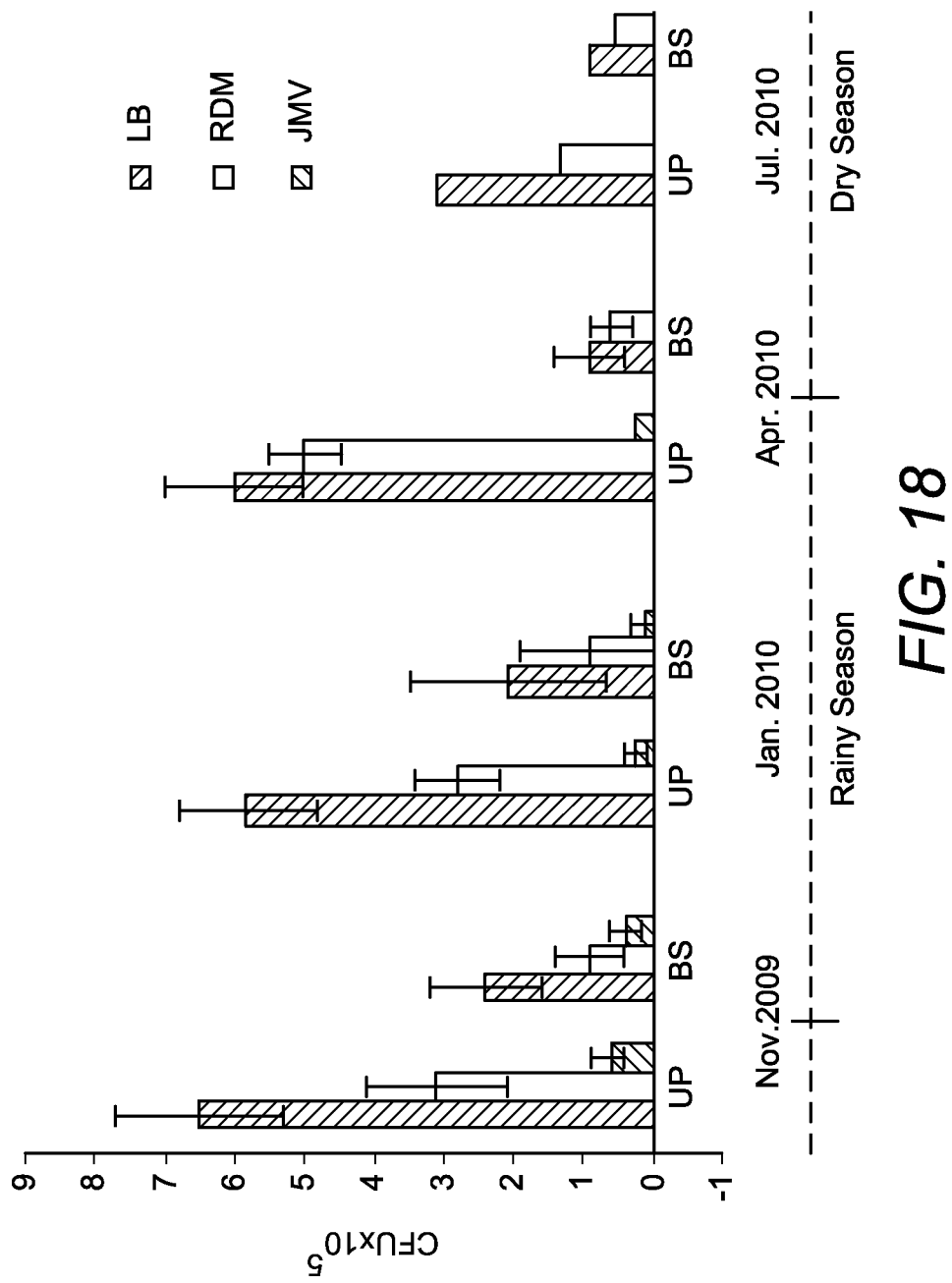
FIG. 18 depicts the number of cultivatable bacteria recovered from site A, under the *Zygophyllum dumosum* canopy (UP) or in bulk soil (BS), and grown in LB, RDM, or JMV culture media. Samples were collected from under the *Z. dumosum* canopy (UP) and from bulk soil (BS) of site A during the first year of study. The soil samples were collected five days after the first rain event. The second sampling occurred one week after a major rain event of 74 mm. The third soil sample was collected approximately two weeks after the last rain event. Soil samples were also collected at the middle of the dry season. The number of colonies obtained on non-selective medium from UP was consistently higher than the number detected in BS. An overall decrease in number of colonies obtained from summer samples was observed both in UP and BS samples.
Figure 19A:
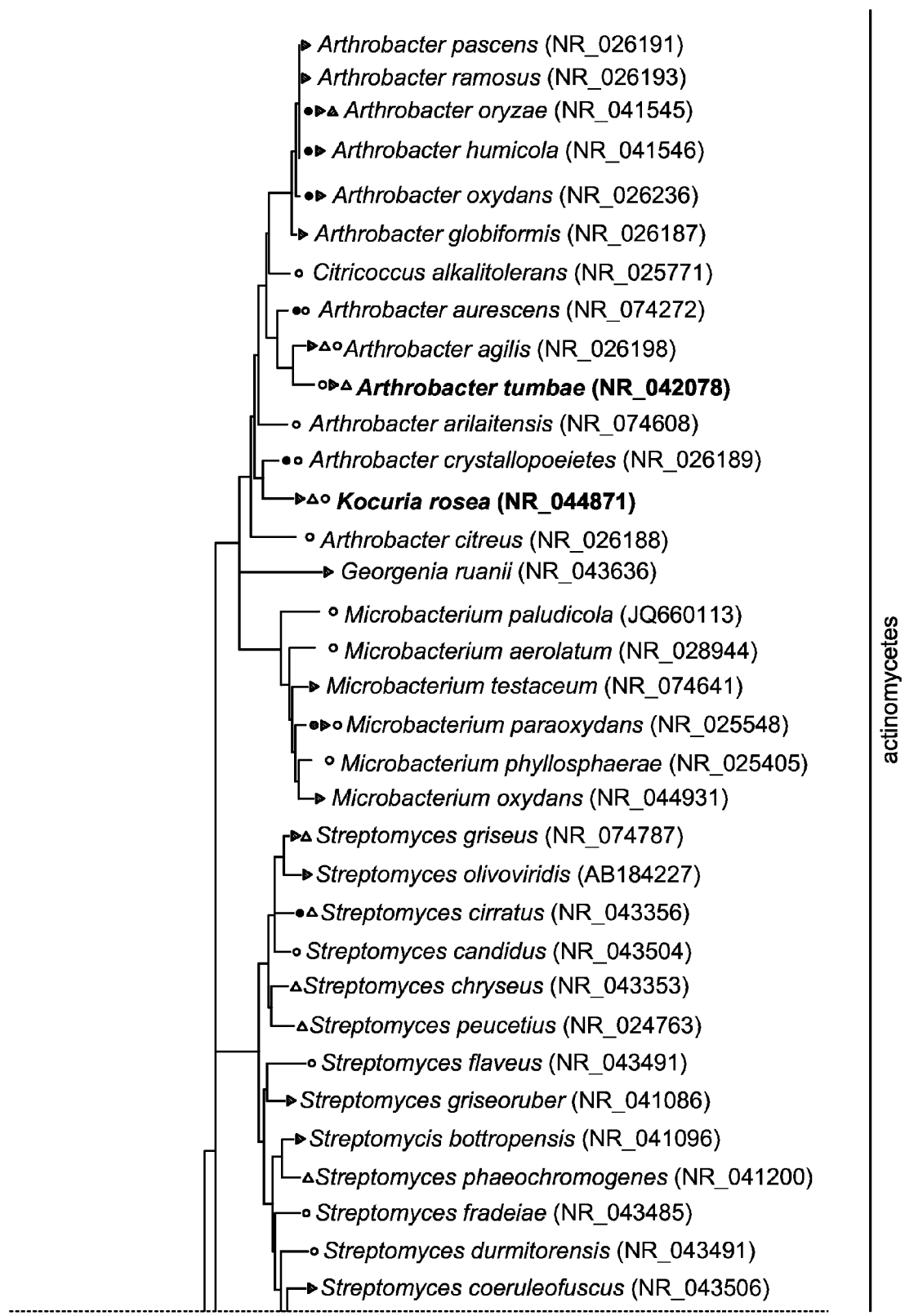
FIG. 19A depicts the phylogenetic relationship of closest sequence match for cultivatable isolates, presumably epiphytes, found in the *Z. dumosum* rhizosphere from under the canopy of site A (▶) or site B (△), from under the *A. halimus* canopy in site B (○), or from bulk soil in site A (●).
Figure 19A:
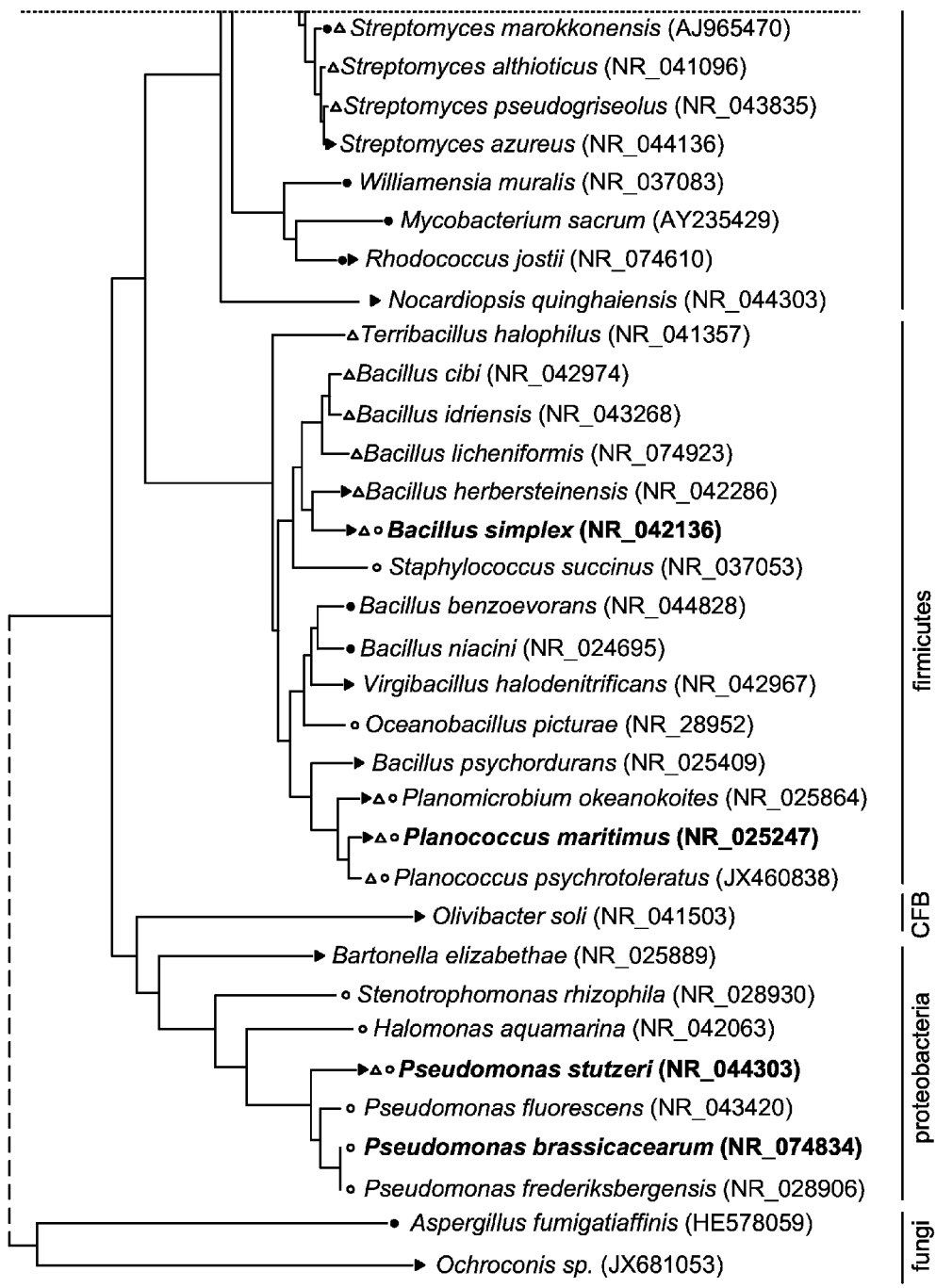
Figure 20:
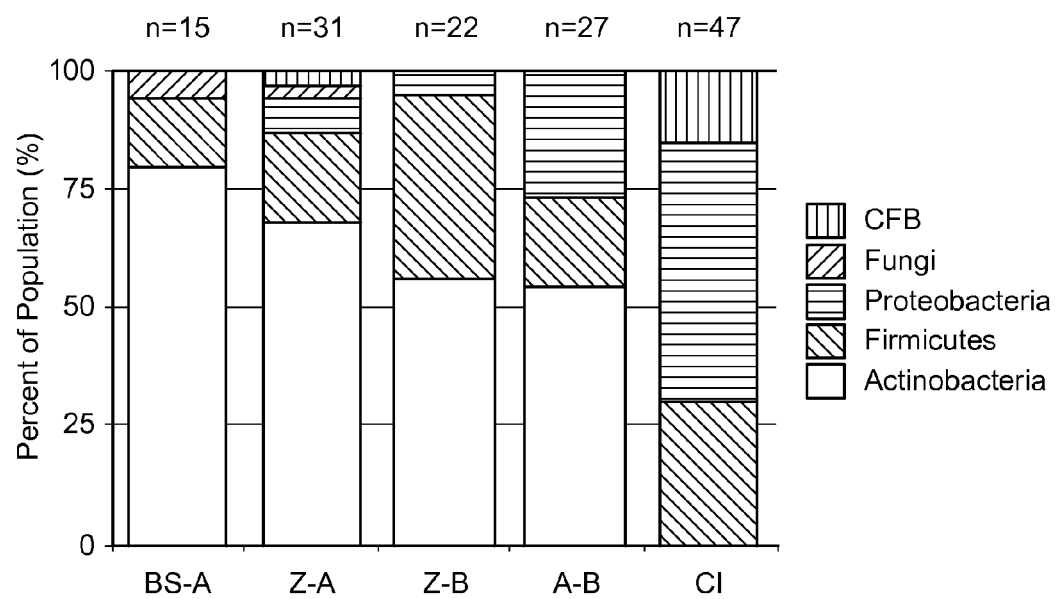
FIG. 20 depicts a microbial community structure of cultivation-dependent and culture-independent isolates. The different colors refer to the percent of the total number of strains identified at each location and with each method. BS-A indicates bulk soil at site A, n=15. Z-A indicates *Zygophyllum dumosum* canopy at site A, n=31. Z-B indicates *Zygophyllum dumosum* canopy at site B; A-B indicates *Atriplex halimus* canopy at site B, n=22; A-B indicates *Atriplex halimus* canopy at site B, n=27; CI indicates cultivation-independent survey of *Zygophyllum dumosum* canopy at site A, n=47.

From the cultivation-dependent analyses, the number of colonies obtained on non-selective plates from under the plant canopy was always higher than the number detected in bulk soil (FIG. 18) as reported previously (Aguirre-Garrido et al., 2012; Bachar et al., 2012). Thirty-one different bacteria species were identified in the *Z. dumosum* site A rhizosphere soil cultivated on the non-selective LB medium, whereas only 15 were identified in the bulk soil (FIGS. 19A and 20). Significantly fewer bacteria appeared on the selective plates. The number of colonies detected on one of the selective media, JMV, was highest when the plants resumed growth at the beginning of the rainy season (in November 2009), but colony number declined during flowering, fruit development, and seed ripening stages (January and April 2010). The number of colonies detected on RDM, a minimal medium, was more than 80% of the number detected on non-selective LB medium growing at the end of the wet season (April 2010) and decreased to 30% by the dry season (July 2010) (FIG. 18). In the rhizosphere samples, the number of cultivatable bacteria growing on LB medium remained unchanged throughout the wet season, but declined in the dry season. In samples of bulk soil, a decrease in the numbers of cultivatable bacteria recovered on either LB or RDM was already observed by April 2010, which was the end of the wet season (FIG. 18).

Of the 15 different bacterial species isolated from bulk soil at site A, the vast majority (ca. 80%) were actinobacterial species (FIG. 19A; FIG. 20, BS-A). The rest were firmicutes, Proteobacteria, and fungi. From under the *Z. dumosum* canopy soils collected at site A, 69% of the 31 total different isolates were Actinobacteria, 20% firmicutes, 6% proteobacteria, and 3% fungi. Only one member of the *Cytophaga-Flavobacteria-Bacteroides* (CFB) group was found at site A under the plant canopy (3% of total, FIG. 19A; FIG. 20, Z-A) and none in bulk soil (BS-A). In site B under the *Z. dumosum* canopy (FIG. 20, Z-B), 41% out of 22 total different species were firmicutes, with the percentages of all the other three groups relatively lower than at the other sites. Actinobacteria account for 55% of the microbial species detected in the UP canopies of *Z. dumosum* and *A. halimus*, growing side by side in Site B, but the proportions of firmicutes and Proteobacteria differ in the two communities (FIG. 20; compare Z-B and A-B). The bacteria isolated from sites A and B under plant (UP) canopy soil and bulk soil (BS) from site A show some overlap, but many fewer Proteobacteria were recovered from the *Z. dumosum* UP canopy samples at site A compared to the UP *A. halimus* samples at site B (FIGS. 19C and 20). Of the Proteobacteria, bacteria closely related to *Pseudomonas stutzeri* were common to both sites as were relatives of the actinomycetes *Kocuria rosea* and *Microbacterium paraoxydans*, and the firmicute *Bacillus simplex*.

Figure 19B:
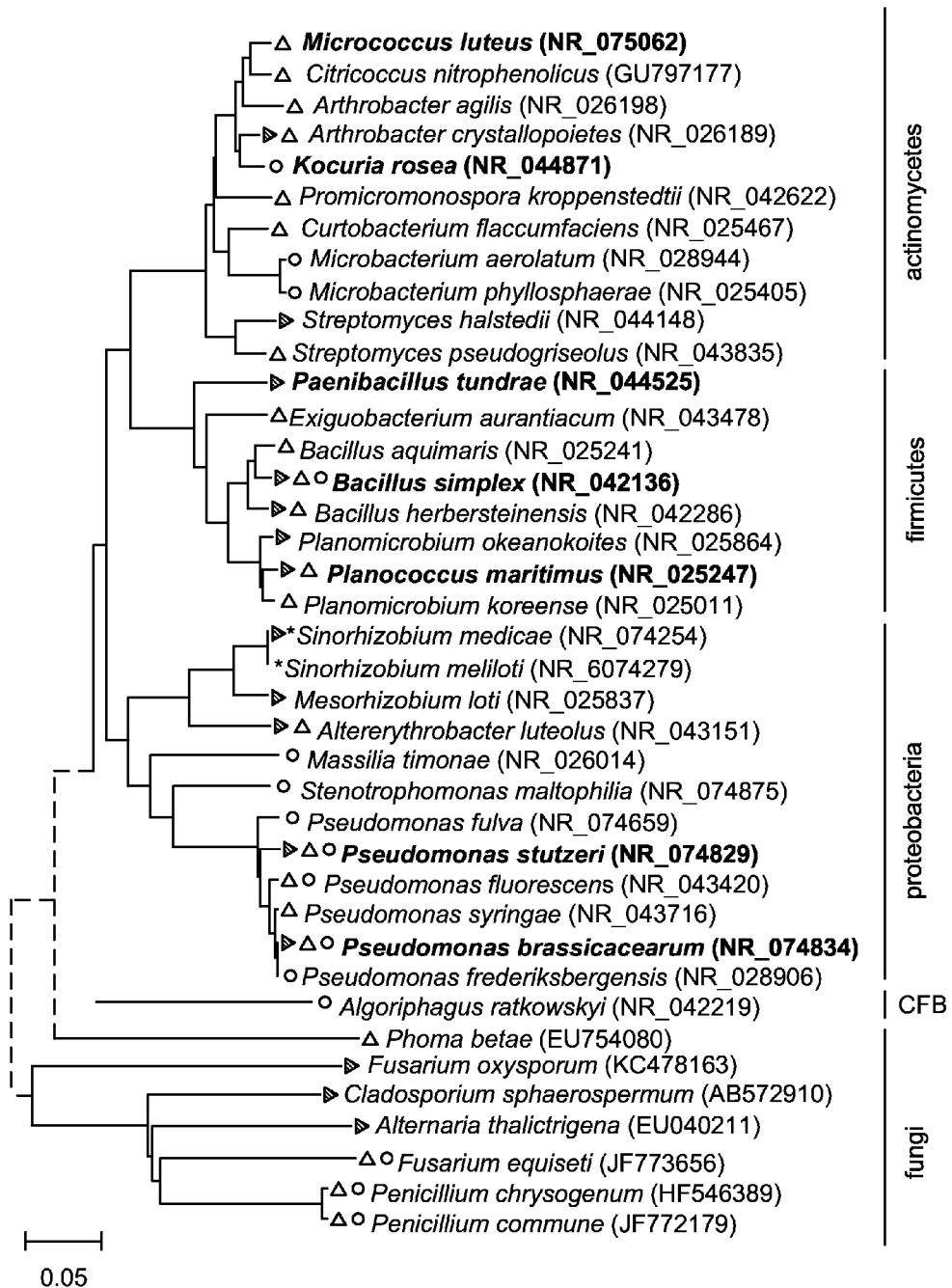
FIG. 19B depicts putative endophytes isolated by cultivation-dependent methods from the roots of *Z. dumosum* from site A (▶), site B (△), *A. halimus* from site B (○), or legume nodule trap experiments (*). For phylogenetic trees, branch distances between fungi and bacteria are truncated for space, indicated with dashed line.
Figure 19D:
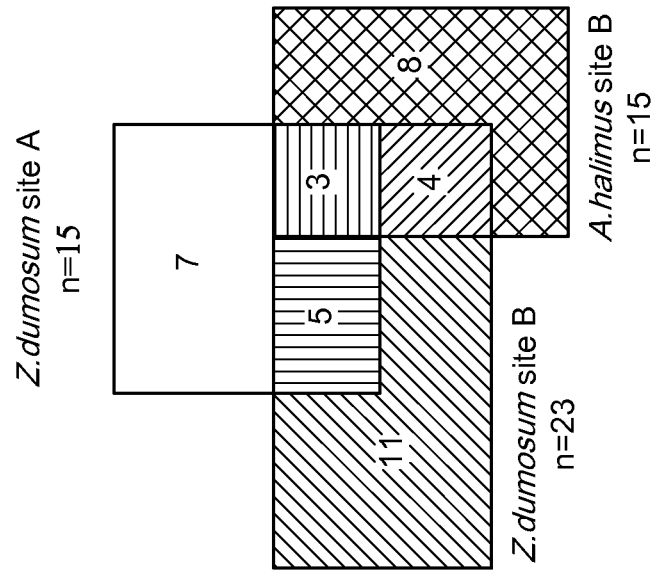
FIG. 19D depicts the overlap of endophytic species found on the roots of *Z. dumosum* from sites A and B, or *A. halimus* from site B.
Figure 19C:
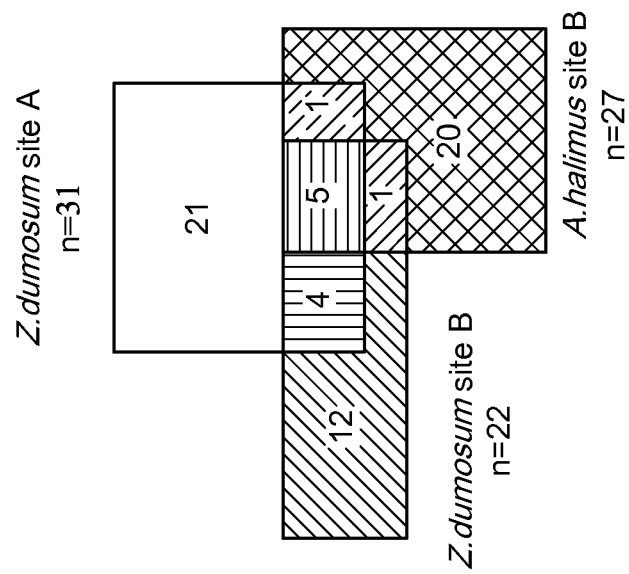
FIG. 19C depicts the overlap between cultivatable species identified under the canopy of *Z. dumosum* from sites A and B, or *A. halimus* from site B.

A number of bacteria and fungi were isolated from surface-sterilized root tissue of *Z. dumosum* in sites A and B, as well as from roots of *A. halimus* in site B, suggesting that they were endophytes (FIG. 19B). Some of the same genera of Actinobacteria were detected, but were related to different species based on percent DNA sequence similarity than in the canopy soils. Also, a greater number of Proteobacteria was detected, particularly members of the genus *Pseudomonas*. Two members of the Rhizobiaceae, which were closely related to *Mesorhizobium loti* and *Sinorhizobium medicae*, were also found as endophytes. Overall, the endophyte population contained a much broader representation with regards to species diversity, especially fungal diversity, than either the bulk soil or UP samples from sites A and B (FIG. 19B), with different populations in the different regions and from different plants, although the overlap was relatively higher than in the canopy soil (FIG. 19D).

Functional Studies

Because such a large number of diverse bacteria were recovered from under the plant canopy at site A and also as putative endophytes, we focused on only a few species for a preliminary functional analysis. Eight isolates (bold in FIG. 19) representing a range of phyla and sampling sites were examined for their ability to secrete hydrolytic enzymes, produce siderophores, and solubilize phosphate. The species analyzed included three actinomycetes, identified by 16S ribotyping to be closely related to *Arthrobacter tumbae*, a putative PGPB, *Kocuria rosea*, and *Micrococcus luteus*; three firmicutes, *Paenibacillus tundrae, Planococcus maritimus*, and *Bacillus simplex*; as well as two proteobacteria, *Pseudomonas stutzeri* and *P. brassicacearum*. *Burkholderia unamae* was used as a positive control for the siderophore and phosphate solubilization assays (Angus et al., 2013).

All eight isolates produced siderophores, but a species closely related to *A. tumbae* developed the greatest halo/ culture diameter ratio for siderophore production. Of the eight, only the bacterium closely related to *P. stutzeri* exhibited chitinase activity whereas 7 of 8 isolates exhibited cellulase activity, as might be expected based on the fact several were found as endophytes. Surprisingly, of the eight isolates, only one strain, a species closely related to *Paenibacillus tundrae*, solubilized inorganic phosphate when grown on PVK plates, but the amount solubilized was considerably less than the control *Burkholderia unamae*. The results for all tests are summarized in Table 7.

TABLE 7

Functional activities of a small sample of diverse bacteria from the Negev Desert Highlands assigned to certain taxonomic groups based on >98% 16S sequence identity

| Taxonomic Group | Isolated as an Endophyte | Cellulase Activity | Chitinase Activity | Siderophore Release | Phosphate Solubilization |
|---|---|---|---|---|---|
| Actinomycetes | | | | | |
| *Arthrobacter tumbae* | No | ++ | − | +++ | − |
| *Kocuria rosea* | Yes | +/− | − | ++ | − |
| *Micrococcus luteus* | Yes | ++ | − | ++ | − |
| Firmicutes | | | | | |
| *Planococcus maritimus* | No | ++ | − | ++ | − |
| *Paenibacillus tundrae* | Yes | − | − | ++ | + |
| *Bacillus simplex* | Yes | ++ | − | + | +/− |
| Proteobacteria | | | | | |
| *Pseudomonas stutzeri* | Yes | ++ | + | ++ | − |
| *Pseudomonas brassicacearum* | Yes | ++ | − | ++ | − |
| *Burkholderia unamae* | Yes | ND | ND | +++ | ++ |

Trap Experiments and Legume Nodulation

Several commonly grown legume species including *Medicago sativa*, (alfalfa), *Lotus japonicus, Melilotus alba* (sweet clover), *Pisum sativum* (pea), and *Vigna unguiculata* (cowpea), *Mimosa pudica, Lupinus succulentus* (lupine), *Macroptilium atropurpureum* (siratro), *Medicago truncatula* and *Trifolium repens* (white clover), were inoculated with soil from the Negev Desert, but of these, only *Medicago sativa* (alfalfa) nodulated. Five different bacterial strains were isolated from the surface-sterilized nodules and re-inoculated onto alfalfa to fulfill Koch's postulates. *Sinorhizobium meliloti* Rm1021 was used as a positive control. Of the five unknowns, only two strains re-nodulated alfalfa. These bacteria were re-isolated from alfalfa nodules, ribotyped, and identified as being closely related to *S. medicae* strains T10 and SWF67501 (Rome et al., 1996).

Additionally, native nodulating bacteria from Negev Desert legumes were also identified. Although plant cover is sparse in deserts, when rainfall is sufficient, many annual plants, particularly annual legumes, germinate, flower, and set seed before the dry season sets in. A number of legumes growing at site A were collected, identified, and prepared as voucher specimens for the UCLA herbarium. These include *Trigonella stellata, Hippocrepis unisiliquosa* L., *Astragalus sinicus* L., *Medicago laciniata* (L.) Miller, and *Retama raetam* (Forck.) Webb. Nodules were found only on the roots of the indigenous legume identified as *T. stellata*. These were squashed after surface-sterilization and the bacteria isolated from the nodules were identified as having 99% sequence identity to *Sinorhizobium (Ensifer) meliloti* strain RBD1 (FIG. 19B).

Community-Level Physiological Profiling

Figure 21A:
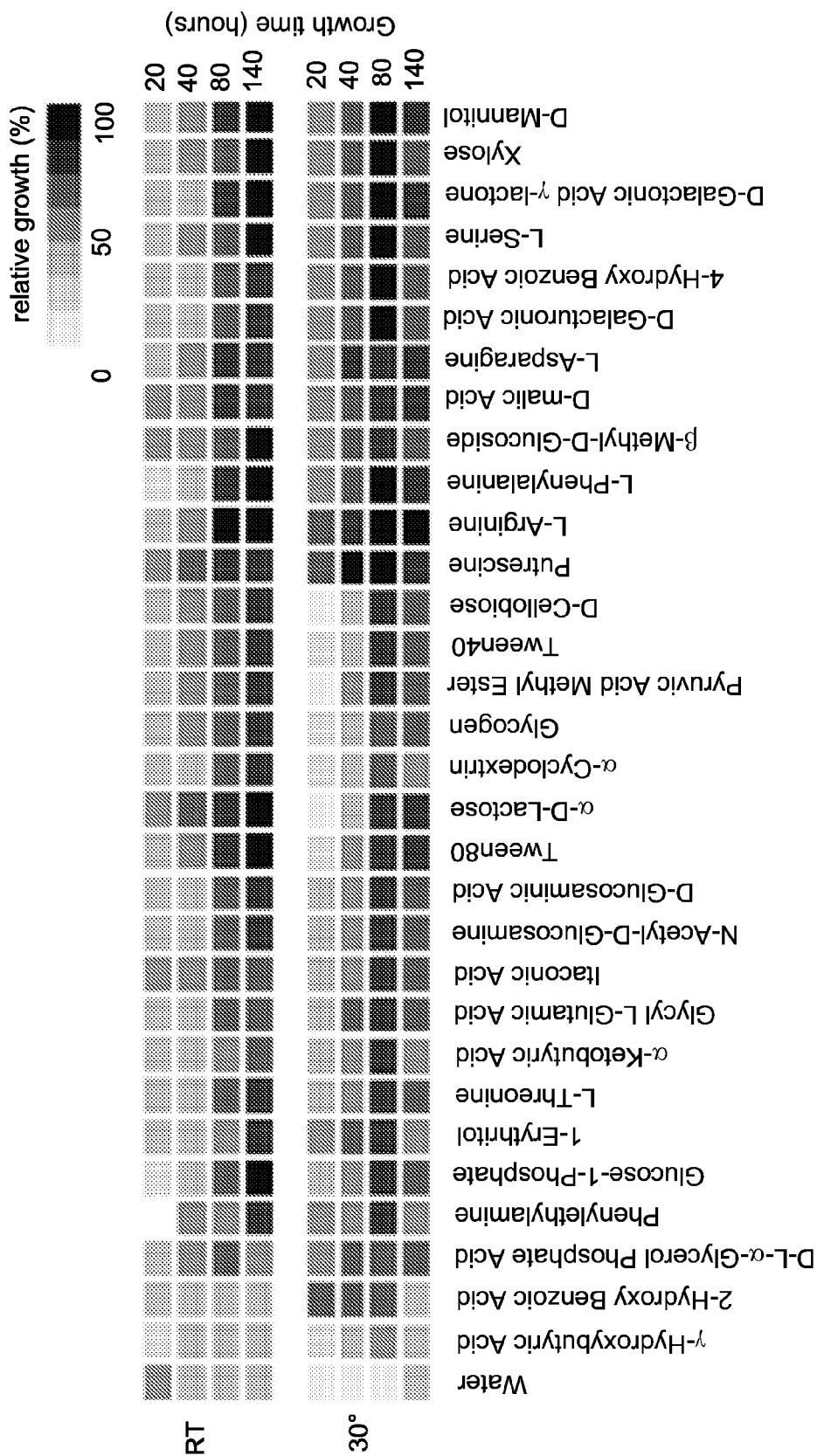
FIG. 21A depicts a CLPP pattern heat map showing the rate of utilization of 31 different carbon sources on an EcoPlate, which was inoculated with under the canopy soil samples from site A and incubated either at 30° C. or at room temperature (approx. 25° C.) for a total of 5 days. Readings were taken daily. A more rapid utilization of a wide variety of carbon sources and achievement of maximal optical density were observed for plates incubated at 30° C.

The microbial community-level physiological profile (CLPP) was examined over a period of 5 days by inoculating Site A UP soil samples into EcoPlate wells and following the rate of utilization of 31 different carbon sources by the community over time. The metabolic patterns presented in a heat map form (FIG. 21) show a more rapid utilization of a wide variety of carbon sources when the inoculated plates were incubated at 30° C. in comparison to plates containing bacteria that were incubated at room temperature (approx. 25° C.). The maximal growth was observed for the 30° C.-incubated plate by day 3, whereas comparable values were recorded for the room temperature-incubated plate by day 5. These observations are consistent with the origin, composition, and dynamics of this Negev Desert microorganism community, which repeatedly showed enhanced activity upon exposure to increased temperature and the ability to adapt and utilize a variety of substrates.

Cultivating Soil Bacteria Using EcoPlates

Figure 21B:
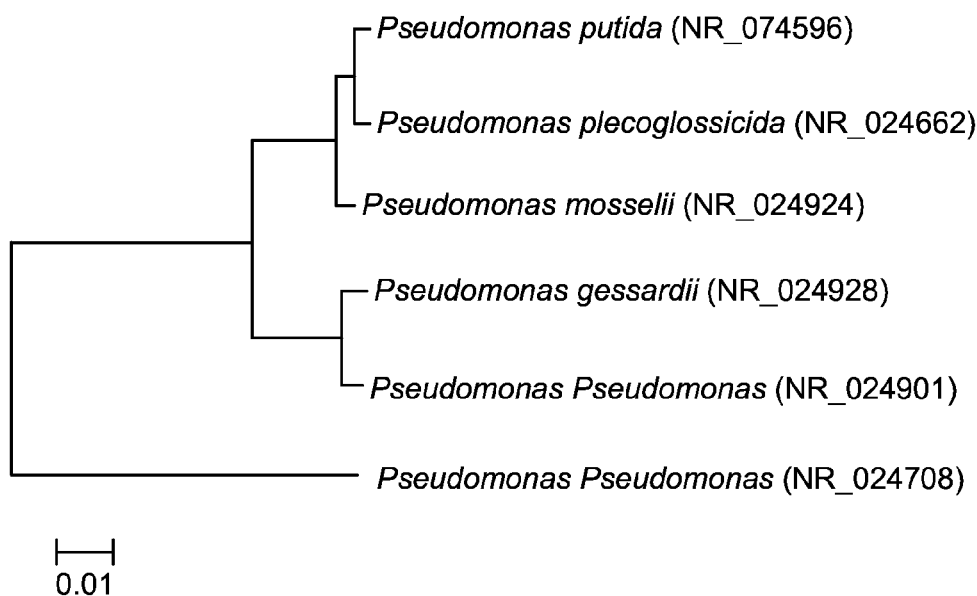
FIG. 21B depicts strains identified from pooled EcoPlate wells. Six *Pseudomonas* strains were identified using 16S ribotyping of DNA isolated after four days of growth at 30° C.

Three replicate wells of each of the 31 carbon sources on the EcoPlate were used as a microenvironment for substrate-based selection. Soil was added to the wells and the pooled samples were analyzed after 4 days of incubation at 30° C. using 16S ribotyping. The samples chosen for analysis represented growth at low, medium, or high optical density readings at day 4 on a variety of carbon sources. Despite the diversity of the original soil sample and the range of EcoPlate conditions, six strains were identified, all closely related to species of *Pseudomonas* (FIG. 21B).

16S rDNA Library

Figure 22:
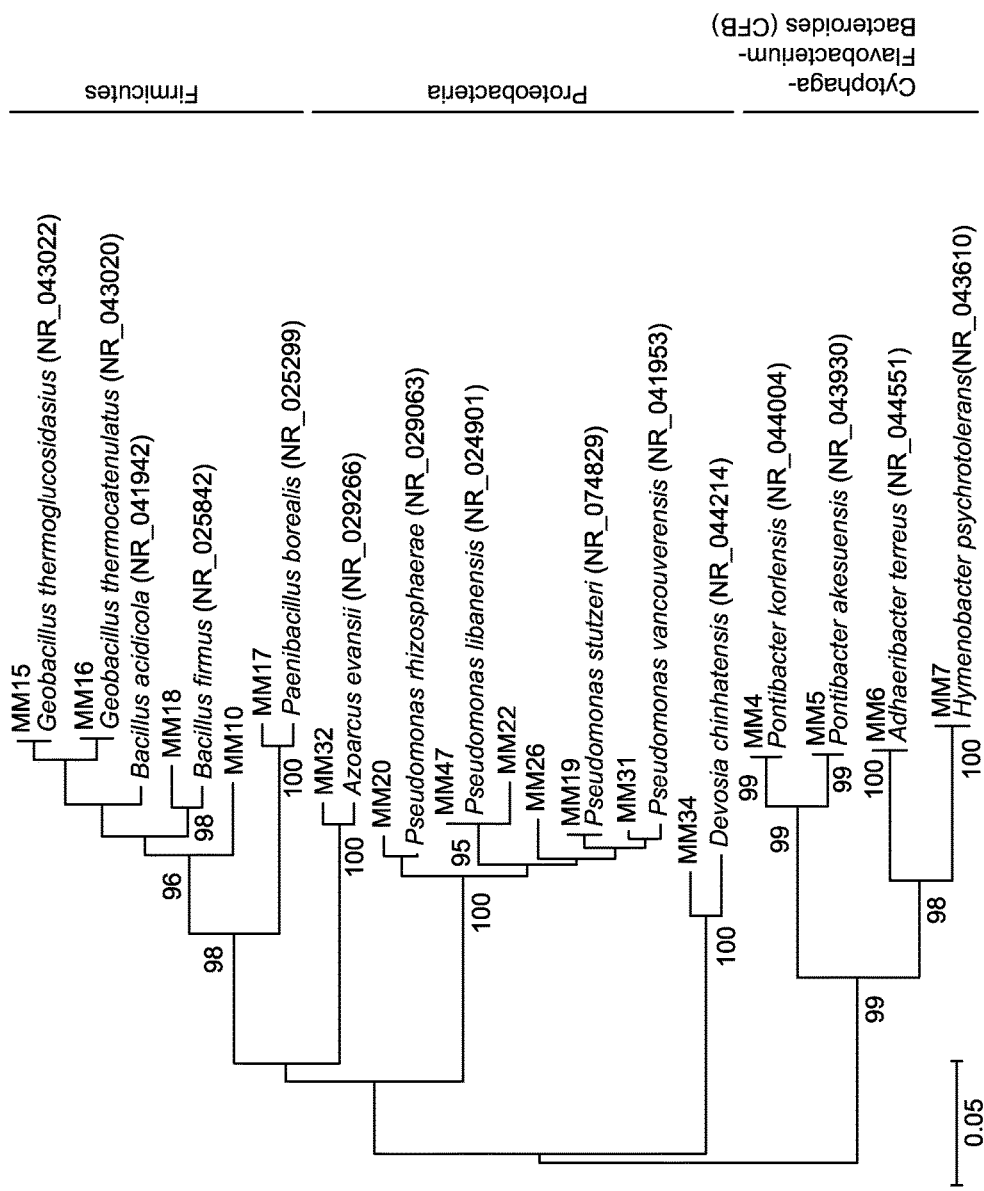
FIG. 22 depicts the diversity of culture-independent isolates. The phylogenetic tree shows the relationship of 16S sequences cloned from soil (MM clones) under the canopy of *Z. dumosum* from site A with closest matches to species from the NCBI 16S ribosomal RNA database. The Neighbor-Joining tree was generated using the p-distance model in MEGA5.1 with bootstrap values ≥96 displayed.

Several OTUs (operational taxonomic units), based on >97% sequence similarity, were detected (FIG. 22). The main groups of bacteria identified were members of the CFB group, the firmicutes, especially Bacillaceae, with the largest percentage being members of Proteobacteriaceae, especially pseudomonads (FIG. 20, CI; and FIG. 22). Several clones, many of which were similar to *Pseudomonas* spp., were very closely related to one another, and were removed from the tree for clarity. Some overlap exists between the species found in the cultivation-dependent and -independent methods; for example, for those isolates closely related to *P. fluorescens* and *P. stutzeri*.

A number of the non-cultivatable isolates were difficult to classify because of either low sequence similarity to known bacteria, below that to be of value for meaningful comparisons, or because few closely related members have been cultured. For example, only one isolate was classified as an *Acidobacterium*, based on >98% sequence similar to the uncultured clone REF-081.

Discussion

The Negev Desert, which occupies more than 60% of the landmass of Israel, is thought to be one of the oldest deserts in the world. In spite of low rainfall, this region is a species-rich plant community dominated by the perennial plant *Z. dumosum*. *Z. dumosum* grows on the rocky slopes in this region whereas in the plateau areas that consist of alluvial loess soil, *Z. dumosum* and *A. halimus* grow side by side.

The microbial communities of the Negev Desert have been recently described. Yu et al. (2012) investigated the microfungal community in the *Z. dumosum* and *Hammada scoparia* root zones in the northern Negev Desert using a cultivation-dependent approach and identified a number of fungal species, mainly Ascomycota although some Zygomycota were detected. However, few fungi were detected in the bulk soil areas between the plants. In another study, the microbiomes of *Z. dumosum* and *H. scoparia* from an arid locale, and of *Noaea muchronata* and *Thymelaea hirsuta* from a semi-arid site, were studied using PFLA (phospholipid fatty acid) and DGGE (denaturing gradient gel electrophoresis) analyses (Ben-David et al., 2011). Differences in the microbial communities were observed not only between the two different sites, but also between the plant rhizosphere and intershrub space soil, or bulk soil, locations. A third study based on PFLA analysis corroborated the finding that bacterial abundance was significantly higher under plant canopies compared to bulk soil in the arid and semi-arid sites of the Negev Desert, but found no difference regarding microbial biomass measured in a Mediterranean site (Bachar et al., 2012).

Rhizosphere microbes promote the growth of plants, particularly in harsh environments, through a number of mechanisms. A goal of the experiments described above was to identify bacterial species and characterize plant growth-promoting behavior that can contribute to the tolerance of desert plants to a wide range of stresses. Microorganisms associated with *Z. dumosum* and *A. halimus* were isolated from soils sampled from two distinct locations in the Negev Desert and subjected to a multi-modal approach for obtaining a broad diversity of microorganisms rather than maximizing the number of OTUs. To this end, soils at different times of the year and from two distinct sites were analyzed. Close relatives of the isolated microbes were identified and several physiological activities were analyzed for a small sample of these. Part of this multipronged approach included a trap experiment to identify legume-nodulating bacteria, which usually do not persist in inhospitable soils because they do not form spores.

Overall, the number of cultivatable microorganisms in the BS was lower than under the canopy of the plants, regardless of the sampling season or the cultivation medium. The total number of cultivatable microorganisms grown on LB (rich medium) in the rhizosphere soil samples collected during the winter and spring (November-April) was twice that found during the summer (July) (FIG. 18). Yet, the increase in the number of microorganisms grown on the selective medium RDM (clearly seen in the April sample) indicated that the community structure was changing. It is believed that this may correlate with the transition from vegetative growth to flowering and fruit/seed production, which could be related to changes in the composition of exudates released from the roots into the soil. For example, Houlden et al. (2008) observed shifts in rhizosphere microbial communities in three crop plants at different stages of their life cycles. Also noticeable is the fact that the number of microorganisms in the BS decreased early (April) whereas those from UP remain high and decreased only in the dry summer. Although some seasonal effects on the microbial communities of UP and BS samples were observed, it is difficult to find any specific pattern during the two years of the study because of wide fluctuations in rainfall from year to year.

Of the cultivatable microbial isolates, minimal overlap was observed between the list of strains found in different sites under the same plant and different plants from the same site, both in the canopy region (FIG. 19C) and in endophytes (FIG. 19D). These findings suggest that both biotic (plant-related) factors as well as abiotic (edaphic) factors are involved in the shaping of the microbial communities associated with the plant root system as has been reported in other studies. It was also found that a large number of microbial species, including several members of the Rhizobiaceae, live as putative endophytes within desert plants. In addition, most of the fungi detected by cultivation-based methods were isolated from surface-sterilized root tissues, suggesting that the endophytic life style may protect these microbes from the harsh desert conditions. However, at this time, we do not know whether any of the endophytic bacteria have plant-growth promoting activities or whether the endophytic fungi function as mycorrhizae.

Many of the microorganisms isolated by the cultivation-dependent method were actinomycetes (FIG. 19), and of these, some were closely related to *Streptomyces phaeochromogenes*, *Planomicrobium okeanokoites*, *Planococcus psychrotoleratus*, and *Bacillus psychrodurans*, which have been reported as being cold tolerant. On the other hand, no putative cold-tolerant actinomycetes were identified through the cultivation-independent approach, but several were found to be related to members of the CFB group, e.g., *Pontibacter* spp. and *Adhaeribacter terreus*, both of which are reported as surviving in temperatures ranging from 6-7° C. to 33-45° C. (Zhang et al., 2008, 2009). Firmicutes that are closely related to *Geobacillus thermoglucosidasius* and *G. thermocatenulatus*, which are known thermophiles and capable of growing at temperatures as high as 68° C. (Nazina et al., 2001), were also found. Without wishing to be bound by theory, it is believed that the Negev Desert isolates disclosed herein exhibit the same traits, a based on the conditions that the microorganisms tolerate in the Negev Desert highlands. The air temperatures span from a low of 6-7° C. in winter months (January-February) to highs of 33-35° C. in the summer (Appendix S2). Soil temperatures may change even more, e.g., reaching almost 50° C. in the summer. Thus, many of the microorganisms found in the Negev Desert are believed to be tolerant of very severe temperature fluctuations.

In addition, many of the microorganisms isolated at the two sites are believed to be salt-tolerant and/or alkaliphilic based on the fact that some isolates share sequence identity with *Nocardiopsis quinghaiensis* (Chen et al., 2008), *Oceanobacillus picturae*, *Bacillus pichinotyi* (Chowdhury et al., 2009), and *Halomonas* spp. (Antonimata et al., 2002), which are reported as being salt-tolerant. Although some isolates were found with high sequence identity to *Citrococcus alkalitolerans* (Li et al., 2005) and *Exiguobacterium aurantiacum* (Mohanty and Mukherji, 2008), they may not necessarily be alkaliphilic because the pH in the Negev Desert has been measured as neutral (Bachar et al., 2012).

Five species of Rhizobiaceae were found in the Negev desert, and then only by analyzing surface-sterilized root tissues for endophytes or by using trap experiments. More had been expected, because at least six different legumes are found in the Negev Desert (Grünzweig and Körner, 2001). However, because the soil was compacted, digging very deep was not possible and thus nodules were recovered only from *Trigonella stellata*. Microorganisms isolated from the nodules as well as soil samples from under *Z. dumosum* were re-inoculated onto a diversity of non-native legumes, but only alfalfa nodulated. It is believed that the two species isolated from these nodules, which were closely related to *S. meliloti* and *S. medicae*, may serve as inoculants for providing fixed nitrogen to alfalfa varieties living in arid environments. In addition to nitrogen-fixing microorganisms, several of the isolates exhibited activities typical of PGPB, such as cellulose and chitin degradation and release of siderophores. However, few of the isolates solubilized rock phosphate. Overall, the results described herein support the hypothesis that the microbial community associated with *Z. dumosum* and *A. halimus* contribute to the plants' tolerance of the environmental conditions prevailing in the Negev Desert.

Only one isolate with close similarity to a plant pathogen, *Pseudomonas syringae* (FIG. 19B), was detected as an endophyte. Several microorganisms isolated by the cultivation-dependent method were reported as clinical isolates based on sequence similarity, but many were isolated as endophytes. For example, isolates showing high sequence identity to *Microbacterum paraoxydans*, *Bacillus idriensis*, and *Massilia timonae* were found in the surface-sterilized root samples (FIG. 19B). A single isolate from site A under the *Z. dumosum* canopy exhibited similarity to *Bartonella elizabethae*, a potential canine pathogen. Overall, very few potential pathogens were detected.

Using a cultivation-dependent methodology, a large number of actinobacteria, firmicutes and proteobacteria, but few CFB members were identified. only one acidobacterial species was detected, which was identified by cultivation-independent methods, perhaps because culturing of this group of bacteria is still limited (Nunes de la Rocha et al., 2008). However, *Acidobacteria* are found in environments ranging in temperature, soil type, and pH (Barns et al., 1999), and thus it is believed that some species will be present in the Negev Desert. Their lack of detection may be due either to a defect in our analysis or because the Negev Desert is inhospitable to *Acidobacteria* for as yet unknown reasons. On the other hand, CFB members are usually not found in desert soils (Yamada and Sekiguchi, 2009). Nonetheless, the cultivation-independent analysis of the Negev Desert soils yielded more representatives from this group than did the cultivation-dependent methodology. This result may have occurred in part because CFB species are slow-growing and require longer culturing times, and thus were missed.

The isolates in the CLPP analysis are heavily dominated by *Pseudomonas* spp., which were not as prevalent as expected in the culture-dependent and independent studies, although more pseudomonads were found using the latter analysis. These results emphasize and reinforce the great complexity of the soil microbiome and the need to examine this heterogeneous community using different approaches and methodologies. The predominance of *Pseudomonas* among the isolates analyzed by the community-level profiling method is believed to be due to their selection during growth in the wells of the EcoPlate, a method known to detect changes in community structure (Smalla et al., 1998). Although Classen et al. (2003) indicated that incubation temperatures do not influence CLPPs performed in Eco-Plates, a 2-day difference was found between incubation at 30° C. and room temperature in reaching an optimal color change. Also, it is possible that the 4-day time period used for the cultivation-dependent analysis was not long enough for a fully completed CLPP.

Several reports have addressed the obstacles, pitfalls, and variations that occur in microbial community analysis (Weaver, 2012; Pan et al., 2010; Berg and Smalla, 2009). The numerical dominance, relative abundance and colonization patterns of a species within a microbial community may have a strong influence on selection and isolation in both cultivation-dependent and -independent methods, yielding an incomplete representation of a community. Sample collection time, conditions at the site of origin, and methodology are critical factors in experimental design and variability within those factors would yield multiple profiles of an apparently identical microbial community. Environmental DNA extraction and amplification methods may also present a biased selection towards species that are easily lysed because of less susceptibility to the effect of inhibitors such as humic acids. The overall effect of the various factors mentioned above could result in a gross under-representation of a diverse rhizospheric environment, a prevalent problem in microbial ecology termed 'the tragedy of the uncommon' (Bent and Forney, 2008).

In this study, a snapshot of the microbial communities in the Negev Desert during the years 2009-2010 has been generated. This was accomplished by obtaining both rhizosphere microbe sequence information and preliminary data on the phenotypes of some of the bacteria within that community. The goal was to have an insight into the natural state of the Negev Desert. Investigations of environments such as deserts are especially critical because more and more of them are being repurposed for other uses. The exploitation of deserts for agricultural land (Köberl et al., 2011) or solar collection fields severely impacts both macro- and microorganism communities. Not only is it essential to take note of the current status of these desert microbial communities, but also it is also important to learn how they influence the growth and survival of their host plants and maintain biological diversity before irreversible changes are established. For one, knowledge of desert plant microbiomes will help in the management of plant rhizospheres to restore degraded desert land (de-Bashan et al., 2012). For another, it is believed that mining for plant-growth promoting microorganisms from arid environments can provide inoculants for stimulating crop growth in environments that are undergoing climate change. Arid and semi-arid regions in particular are much more sensitive to climate change than other parts of the globe (Yair et al., 2008), and will need the input of dry land-evolved inoculants for soil restoration in areas of severe climate change. This study has led to the isolation of *S. meliloti* and *S. medicae* strains that are believed to be useful for growing alfalfa in arid environments.

What is claimed is:

1. A method of increasing one or more plant growth characteristics in a plant, comprising: providing to the plant an effective amount of one or more plant growth-promoting microbial isolates selected from the group consisting of *Bacillus simplex* 30N-5 and *Bacillus subtilis* 30VD-1.

2. The method of claim 1, wherein the plant is provided both of the plant growth-promoting microbial isolates.

3. The method of claim 1, wherein the one or more plant growth characteristics are selected from the group consisting of plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions.

4. The method of claim 1, wherein the one or more plant growth characteristics are growth under arid conditions, growth under low pH conditions, or both.

5. The method of claim 1, wherein the one or more plant growth characteristics are resistance to one or more pathogens, resistance to fungal growth, or both.

6. The method of claim 1, further comprising providing to the plant an effective amount of one or more rhizobial bacterial strains.

7. The method of claim 1, wherein providing to the plant an effective amount of one or more plant growth-promoting microbial isolates comprises contacting seed of the plant with the one or more plant growth-promoting microbial isolates.

8. The method of claim 1, wherein providing to the plant an effective amount of one or more plant growth-promoting microbial isolates comprises contacting the plant or part thereof with the one or more plant growth-promoting microbial isolates.

9. The method of claim 1, wherein providing to the plant an effective amount of one or more plant growth-promoting microbial isolates comprises contacting the plant roots with the one or more plant growth-promoting microbial isolates.

10. The method of claim 1, wherein providing to the plant an effective amount of one or more plant growth-promoting microbial isolates comprises contacting the plant rhizosphere with the one or more plant growth-promoting microbial isolates.

11. The method of claim 10, wherein the rhizosphere comprises one or more of roots, root nodules, root caps, root exudate, rhizosphere-associated microorganisms, and rhizosphere-associated soil.

12. The method of claim 1, wherein the plant is a dicotyledon.

13. The method of claim 1, wherein the plant is selected from the group consisting of a desert plant, a desert perennial, a crop plant, and a legume.

14. The method of claim 1, wherein the isolate comprises a *Bacillus subtilis* 30VD-1 strain having all the identifying characteristics of a *Bacillus subtilis* 30VD-1 strain deposited with the Agricultural Research Service Culture Collection under Accession No. B-50966.

15. The method of claim 1, wherein the isolate comprises a *Bacillus simplex* 30N-5 strain having all the identifying characteristics of a *Bacillus simplex* 30N-5 strain deposited with the Agricultural Research Service Culture Collection under Accession No. B-50968.

* * * * *

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgaattcgt cgacaacaga gtttgatcct ggctcag                               37

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cccgggatcc aagcttaagg aggtgatcca gcc                                   33
```